(12) United States Patent
Luna et al.

(10) Patent No.: US 11,590,001 B2
(45) Date of Patent: Feb. 28, 2023

(54) ANTERIOR ANKLE APPROACH SYSTEM AND METHOD

(71) Applicant: Wright Medical Technology, Inc., Memphis, TN (US)

(72) Inventors: Ramon Luna, Arlington, TN (US); Meghan Kubacki, Memphis, TN (US); Terrance W. Strohkirch, Memphis, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 413 days.

(21) Appl. No.: 16/605,849

(22) PCT Filed: Jul. 5, 2017

(86) PCT No.: PCT/US2017/040730
§ 371 (c)(1),
(2) Date: Oct. 17, 2019

(87) PCT Pub. No.: WO2019/009891
PCT Pub. Date: Jan. 10, 2019

(65) Prior Publication Data
US 2020/0113712 A1    Apr. 16, 2020

(51) Int. Cl.
*A61F 2/46* (2006.01)
*A61B 17/17* (2006.01)
(Continued)

(52) U.S. Cl.
CPC ........ *A61F 2/4606* (2013.01); *A61B 17/1682* (2013.01); *A61B 17/1775* (2016.11);
(Continued)

(58) Field of Classification Search
CPC ... A61F 2/4202; A61F 2/4606; A61B 17/1775
See application file for complete search history.

(56) References Cited

U.S. PATENT DOCUMENTS

| 2,638,092 A | 5/1953 | Dorr |
| 4,622,723 A | 11/1986 | Krauss |

(Continued)

FOREIGN PATENT DOCUMENTS

| AU | 2015202080 A1 | 5/2015 |
| JP | 2016043114 A | 4/2016 |

(Continued)

OTHER PUBLICATIONS

International Search Report and Written Opinion issued in connection with corresponding International Patent Application No. PCT/US2017,040730, dated Apr. 5, 2018, 15 pages.

(Continued)

*Primary Examiner* — Zade Coley
(74) *Attorney, Agent, or Firm* — Duane Morris LLP

(57) ABSTRACT

A method of ankle replacement includes forming an anterior cut in a bone and forming a stem hole in a distal end of the bone. The stem hole is formed using a plurality of broaches positioned against the distal end of the bone through the anterior cut. A first portion and a second portion of a stem implant are inserted into the stem hole through the anterior cut in the bone. The first portion is coupled to the second portion using a coupling device inserted through the anterior cut in the bone. The stem implant is impacted into the stem hole using an offset impactor.

34 Claims, 60 Drawing Sheets

(51) Int. Cl.
*A61B 17/16* (2006.01)
*A61F 2/42* (2006.01)
*A61B 17/00* (2006.01)
*A61B 17/92* (2006.01)

(52) U.S. Cl.
CPC .. *A61F 2/4202* (2013.01); *A61B 2017/00738* (2013.01); *A61B 2017/922* (2013.01); *A61F 2002/4681* (2013.01)

(56) References Cited

U.S. PATENT DOCUMENTS

| | | | |
|---|---|---|---|
| 5,676,668 A | 10/1997 | McCue et al. | |
| 7,591,821 B2 | 9/2009 | Kelman | |
| 7,621,921 B2 | 11/2009 | Parker | |
| 7,857,816 B2 | 12/2010 | Burgi | |
| 7,963,996 B2 | 6/2011 | Saltzman et al. | |
| 8,715,362 B2* | 5/2014 | Reiley | A61F 2/4202 623/23.44 |
| 9,402,640 B2* | 8/2016 | Reynolds | A61B 17/1703 |
| 9,480,571 B2 | 11/2016 | McGinley et al. | |
| 2005/0125070 A1* | 6/2005 | Reiley | A61F 2/4202 623/21.18 |
| 2005/0203535 A1 | 9/2005 | Parry et al. | |
| 2006/0184176 A1* | 8/2006 | Straszheim-Morley | A61F 2/4684 606/88 |
| 2006/0229730 A1* | 10/2006 | Railey | A61B 17/1775 623/23.44 |
| 2008/0109006 A1 | 5/2008 | Waltersdorff et al. | |
| 2009/0182433 A1* | 7/2009 | Reiley | A61B 17/15 623/18.11 |
| 2010/0305711 A1 | 12/2010 | McKinnon et al. | |
| 2011/0218542 A1* | 9/2011 | Lian | A61B 17/1775 606/88 |
| 2013/0006370 A1 | 1/2013 | Wogoman et al. | |
| 2013/0046313 A1* | 2/2013 | Lian | A61F 2/46 606/99 |
| 2014/0188236 A1 | 7/2014 | McGinley et al. | |
| 2014/0324053 A1 | 10/2014 | Stemniski et al. | |
| 2015/0134071 A1* | 5/2015 | Luna | A61B 17/1739 606/62 |
| 2016/0051267 A1 | 2/2016 | Sander | |
| 2016/0135963 A1 | 5/2016 | Kerboul et al. | |
| 2018/0055648 A1 | 3/2018 | Dhillon et al. | |

FOREIGN PATENT DOCUMENTS

| | | |
|---|---|---|
| WO | 2016028270 A1 | 2/2016 |
| WO | 2016055851 A1 | 4/2016 |
| WO | 2016141274 A1 | 9/2016 |
| WO | 2017223059 A1 | 12/2017 |

OTHER PUBLICATIONS

Extended Search Report issued in connection with corresponding European Patent Application No. 17916909.9, dated Feb. 15, 2021, 22 pages.
Surgic A1: "Infinity Total Ankle System", Dec. 10, 2014, http://www.totalankleinstitute.com/wp-content/uploads/2016/01/010395b_infinity-total-ankle-surgical-technique.pdf [retrieved on Mar. 24, 2020.
Zimmer: "Intramedullary Nail Extraction Surgical Techniques Universal Nail Extraction System", Jan. 1, 2004, retrieved from the Internet on Oct. 30, 2020, https://www.zimmerbiomet.com/content/dam/zimmer-biomet/medical-professionals/000-surgical-techniques/trauma/intramedullary-nail-extraction-surgical-technique.pdf,16 pages.
Wright Medical: "INFINITY(TM) Total Ankle System Animation", Jul. 29, 2015 (Jul. 29, 2015), p. 1, XP054981047, Retrieved from the Internet: URL:https://www.youtube.com/watch?V= TjquNnCPj21&ab_channel=WrightMedical [retrieved on Oct. 30, 2020].
James Gilroy: "Shukla Winquist Training Video", Dec. 17, 2013 (Dec. 17, 2013), p. 1, XP054981048, Retrieved from the Internet: URL:https://www.youtube.com/watch? V=TGzPvU4czoo&ab_channel=JamesGilroy [retrieved on Oct. 30, 2020).
James Gilroy: "Shukla Xtract All Hip/Modular Training Video", Dec. 17, 2013 (Dec. 17, 2013), p. 1, XP054981049, Retrieved from the Internet: URL:https://www.youtube.com/watch?v=kWVdmBOMRiQ&ab_channel=JamesGilroy (retrieved on Oct. 30, 2020).
Innomed:"Innovations in Orthopedic Instruments Rivero Anti-Rotation Corkscrew Femoral Head Remover Hip: Primary & Revision", Mar. 1, 2016 (Mar. 1, 2016), pp. 1-56, XP055745418, Retrieved from the Internet: URL:http://fischermedica.ldk/wp-content/uploads/ Innomed_HipInstruments_March2016.pdf [retrieved on Oct. 30, 2020).
Office Action issued in connection with corresponding Canadian Patent Application No. 3,059,721, dated Dec. 9, 2020, 4 pages.
First Examination Report issued in connection with corresponding Australian Patent Application No. 2017422380, dated Oct. 10, 2020.
Anderson, et al., "Infinity Total Ankle System Surgical Technique", URL:http://www.totalankleinstitute.com/wp-content/uploads/2016/01/010395b_infinity-total-ankle-surgical-technique.pdf, Dec. 10, 2014.
Office Action issued in connection with corresponding Canadian Patent Application No. 3,059,721, dated Aug. 17, 2021, 5 pages.
Office Action issued in connection with Canadian Patent Application No. 3,116,744, dated Jul. 19, 2022, 6 pages.

\* cited by examiner

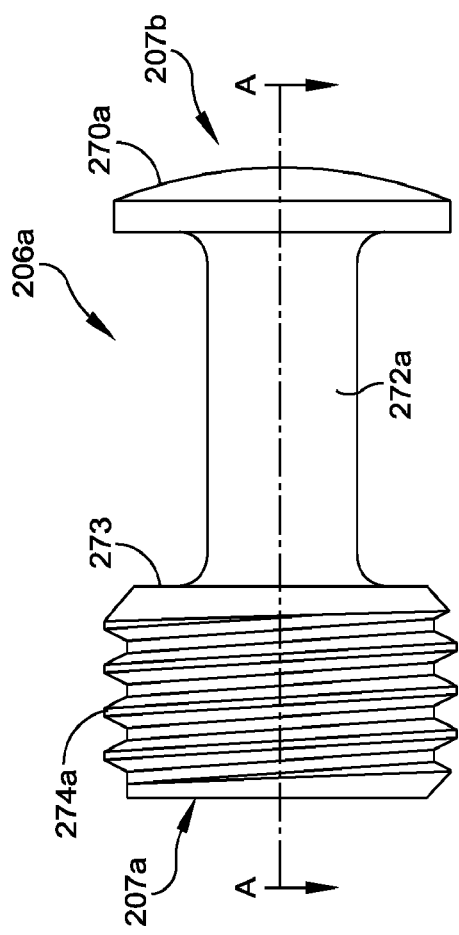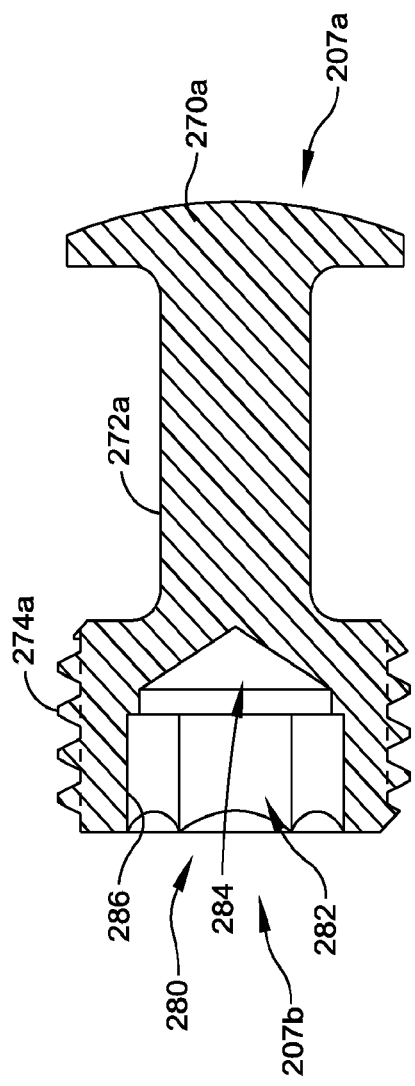
FIG. 21
FIG. 22

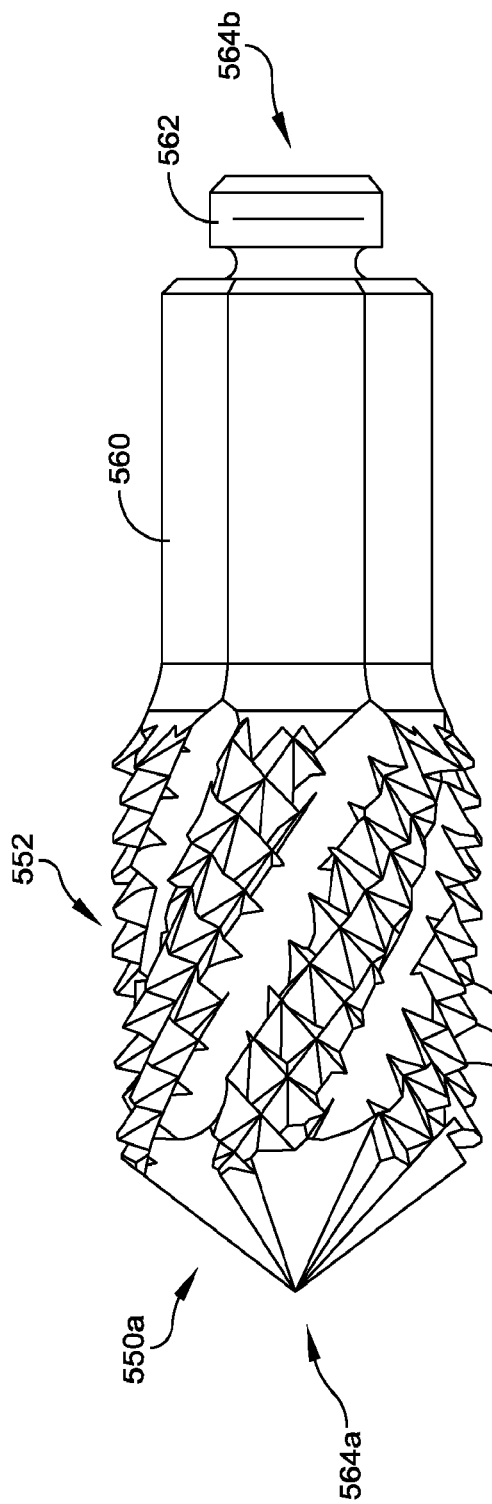
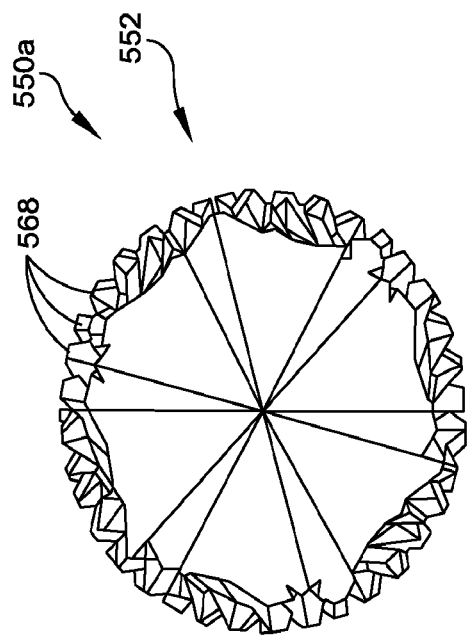
FIG. 46
FIG. 47

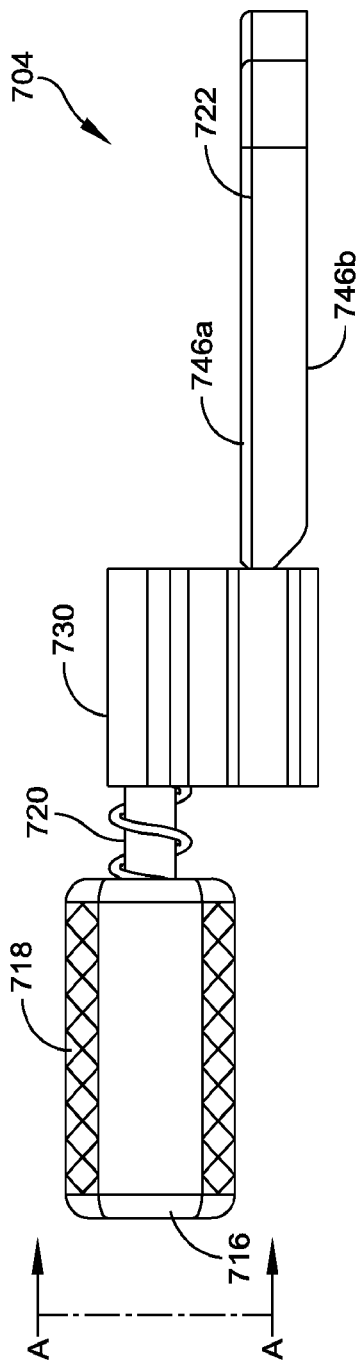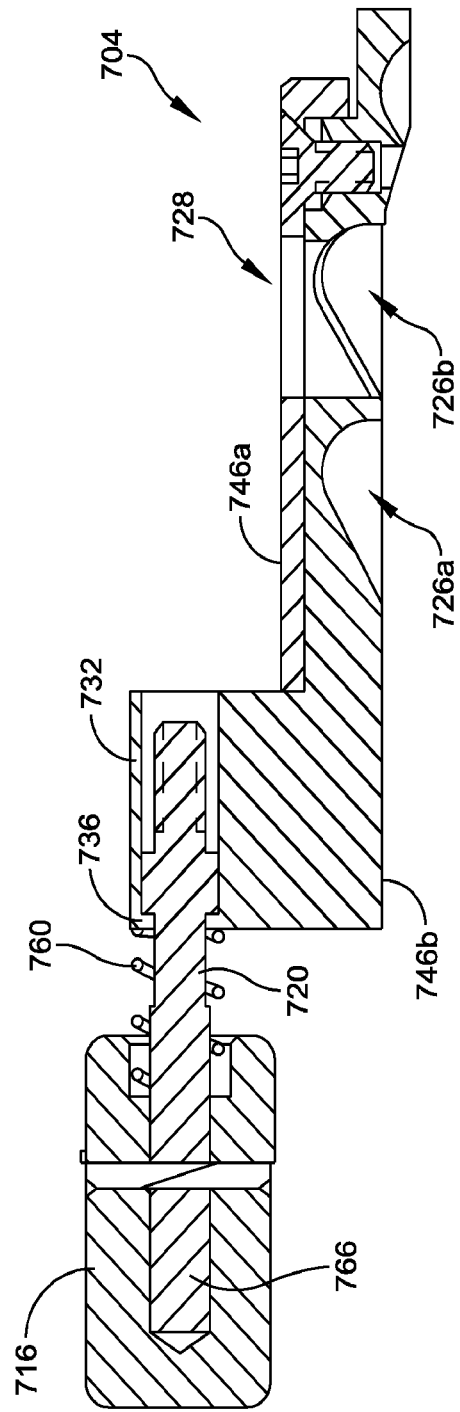

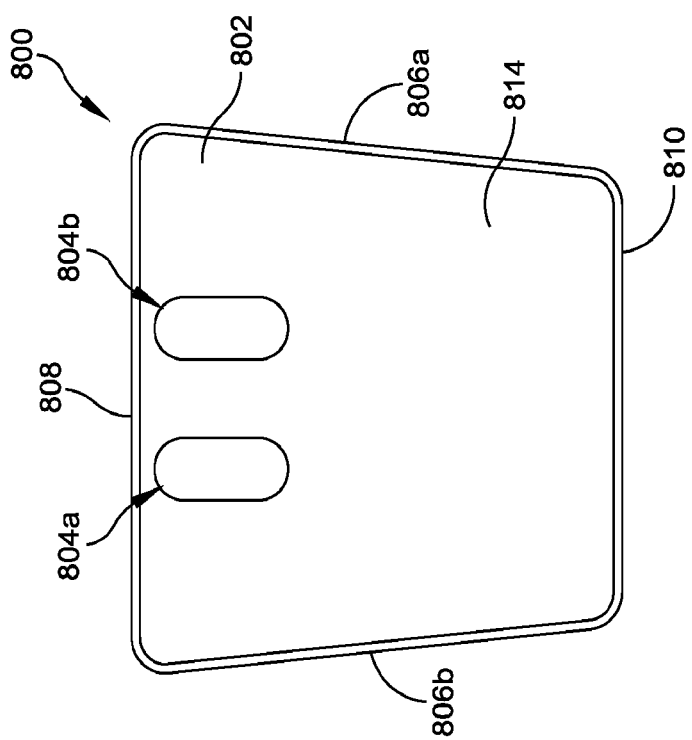

ANTERIOR ANKLE APPROACH SYSTEM AND METHOD

CROSS REFERENCE TO RELATED APPLICATION

This is a National Stage Application, filed under 35 U.S.C. 371, of International Patent Application No. PCT/US2017/040730, filed on Jul. 5, 2017, contents of which are incorporated herein by reference in its entirety.

BACKGROUND

An ankle joint may become severely damaged and painful due to arthritis from prior ankle surgery, bone fracture, infection, osteoarthritis, posttraumatic osteoarthritis or rheumatoid arthritis, for example. Options for treating the injured ankle have included anti-inflammatory and pain medications, braces, physical therapy, amputation, joint arthrodesis, and total ankle replacement.

Current ankle joint treatment options include accessing an ankle and inserting one or more implants into a tibia by drilling a hole starting in the bottom of the talus (e.g., the bottom of the foot), extending through the talus and into the tibia. Such approaches require excessive bone removal from the talus, increases recovery time, and can create complications during surgery.

SUMMARY

In various embodiments, a method of ankle replacement is disclosed. The method includes forming an anterior cut in a bone and forming a stem hole in a distal end of the bone. The stem hole is formed using a plurality of broaches positioned against the distal end of the bone through the anterior cut. A first portion and a second portion of a stem implant are inserted into the stem hole through the anterior cut in the bone. The first portion is coupled to the second portion using a coupling device inserted through the anterior cut in the bone. The stem implant is impacted into the stem hole using an offset impactor.

In various embodiments, an offset impactor is disclosed. The offset impactor includes a body including a longitudinal section having a first transverse arm coupled to a first end and a second transverse arm coupled to a second end. The first transverse arm and the second transverse arm define a spacing therebetween. An impactor surface is coupled to the first transverse arm and is configured to receive an impaction force. An impactor head is coupled to the second transverse arm. The impaction force is transferred from the first transverse arm to the second transverse arm by the longitudinal section. The impactor head is configured to convert the impaction force to a linear impaction force.

In various embodiments, a kit is disclosed. The kit includes an offset impactor and a plurality of broaches. The offset impactor includes a body including a longitudinal section having a first transverse arm coupled to a first end and a second transverse arm configured to be coupled to a second end, an impactor surface coupled to the first transverse arm, and an impactor head configured to be coupled to the second transverse arm. The impactor surface is configured to receive an impaction force that is transferred from the first transverse arm to the second transverse arm by the longitudinal section. The impactor head is configured to convert the impaction force to a linear impaction force. Each of the plurality of broaches is configured to be coupled to the impactor head such that the linear impaction force is applied along a longitudinal axis of a selected one of the plurality of broaches.

BRIEF DESCRIPTION OF THE FIGURES

The features and advantages of the present invention will be more fully disclosed in, or rendered obvious by the following detailed description of the preferred embodiments, which are to be considered together with the accompanying drawings wherein like numbers refer to like parts and further wherein:

FIG. 21 illustrates an alignment screw configured to be interfaced with the broach guide of FIG. 12, in accordance with some embodiments.

FIG. 22 illustrates a cross-sectional view of the alignment screw taken along line A-A of FIG. 21, in accordance with some embodiments.

FIG. 46 illustrates a side view of a second broach, in accordance with some embodiments.

FIG. 47 illustrates a front view of the second broach of FIG. 46, in accordance with some embodiments.

FIG. 63 illustrates a side view of the impaction insert of FIG. 62, in accordance with some embodiments.

FIG. 64 illustrates a cross-sectional view of the impaction insert of FIG. 64 taken along line A-A in FIG. 62, in accordance with some embodiments.

FIG. 65 illustrates a top view of a talar protector, in accordance with some embodiments.

DETAILED DESCRIPTION

Figure 1:
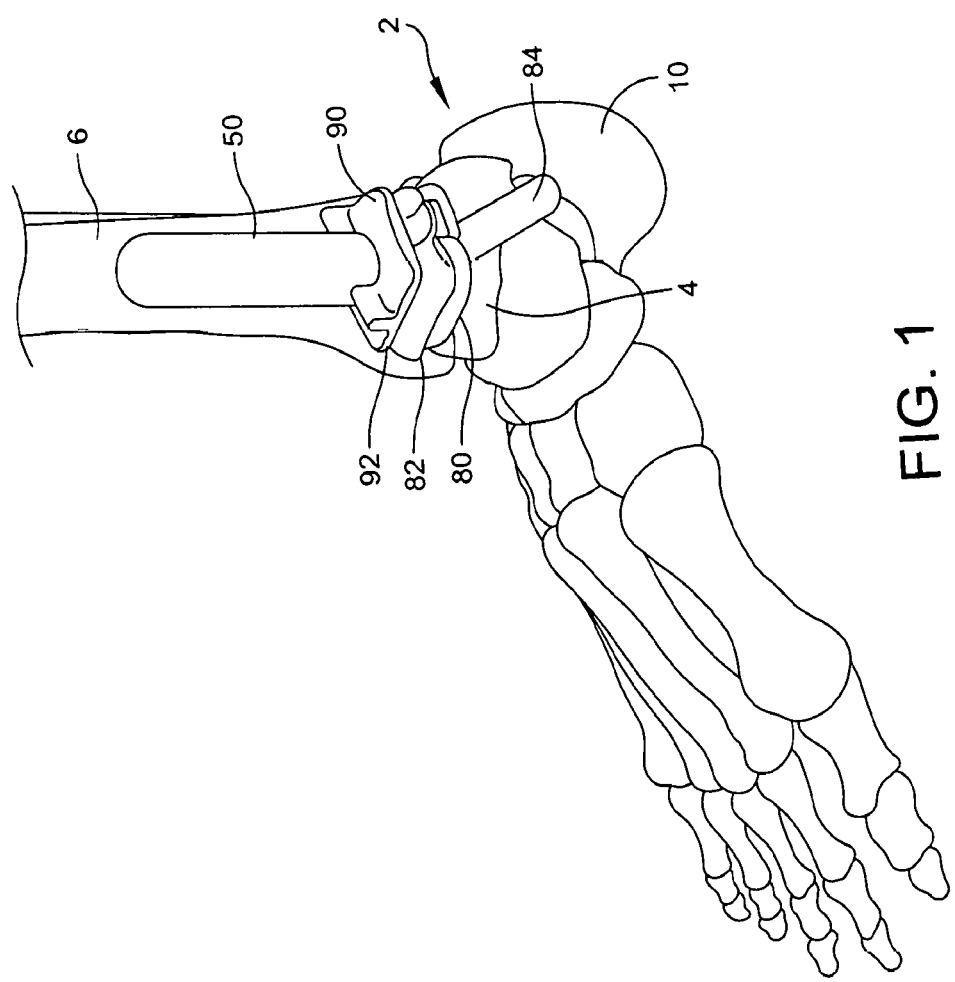
FIG. 1 illustrates an ankle joint.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top," "bottom," "proximal," "distal," "superior," "inferior," "medial," and "lateral" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected," refer to a relationship wherein structures are secured or attached to one another either directly or indirectly through intervening structures, as well as both movable or rigid attachments or relationships, unless expressly described otherwise. As used herein, proximal/distal refers to a relationship between an identified element (such as a surgical instrument) and a user (e.g., a surgeon) grasping or manipulating the identified element. The terms superior/inferior refer to a relationship with respect to an identified surgical site.

In various embodiments, an anterior ankle replacement system is disclosed. The anterior ankle replacement system includes a spreader configured to spread a resected tibia. A broach guide is coupled to an anterior surface of the tibia and the spreader removed. An alignment wing is coupled to the broach guide to confirm positioning of the broach guide with respect to the tibia. The anterior ankle system further includes an offset impactor configured to transfer an impaction force to one or more broaches to form a stem hole in a distal end of a tibia. The one or more broaches can include at least one first (or pilot) broach and at least one second (or enlarging) broach. In some embodiments, a stem and/or at least one segment of a multi-component stem is sized and configured for insertion into the stem hole. An implant assembly is coupled to the offset impactor and impacted into a fixed engagement with the tibial stem implant. Additional ankle implants can be coupled to the tibial tray implant and/or a talus to complete total ankle replacement.

FIG. 1 illustrates an anatomic view of an ankle joint 2. The ankle joint 2 comprises a talus 4 in contact with a tibia 6 and a fibula (not labelled). A calcaneus 10 is located adjacent to the talus 4. In total ankle replacements, the talus 4 and the tibia 6 may be resected, or cut, to allow insertion of a talar implant and a tibial implant.

A total ankle replacement system can include a talar implant 80 and a tibial implant 90. The talar implant 80 can include an articulation surface 82 configured to mimic a natural articulation surface of the talus 4. A tibial implant 90 can be sized and configured for installation into the tibia 6. The tibial implant 90 can include a body having an articulation surface 92 configured to mimic a natural articulation of the tibia 6 and a stem 50 extending into the tibia 6 to anchor the tibial implant 80. The articulation surfaces 82, 92 of the respective implants 80, 90 replace the natural ankle joint surfaces, which are removed, to restore a range of motion that mimics the natural joint.

The articulation surfaces 82, 92 may be made of various materials, such as, for example, polyethylene, high molecular weight polyethylene (HMWPE), ultrahigh molecular weight polyethylene (UHMWPE), rubber, titanium, titanium alloys, chrome cobalt, surgical steel, and/or any other suitable metal, ceramic, sintered glass, artificial bone, pyrocarbon, and/or any combination thereof. In some embodiments, each of the articulation surfaces 82, 92 can comprise the same and/or different materials. For example, the tibial articulation surface 92 may comprise a plastic or other non-metallic material and the talar articulation surface 82 may comprise a metal surface. Those skilled in the art will recognize that any suitable combination of materials may be used.

Figure 2:
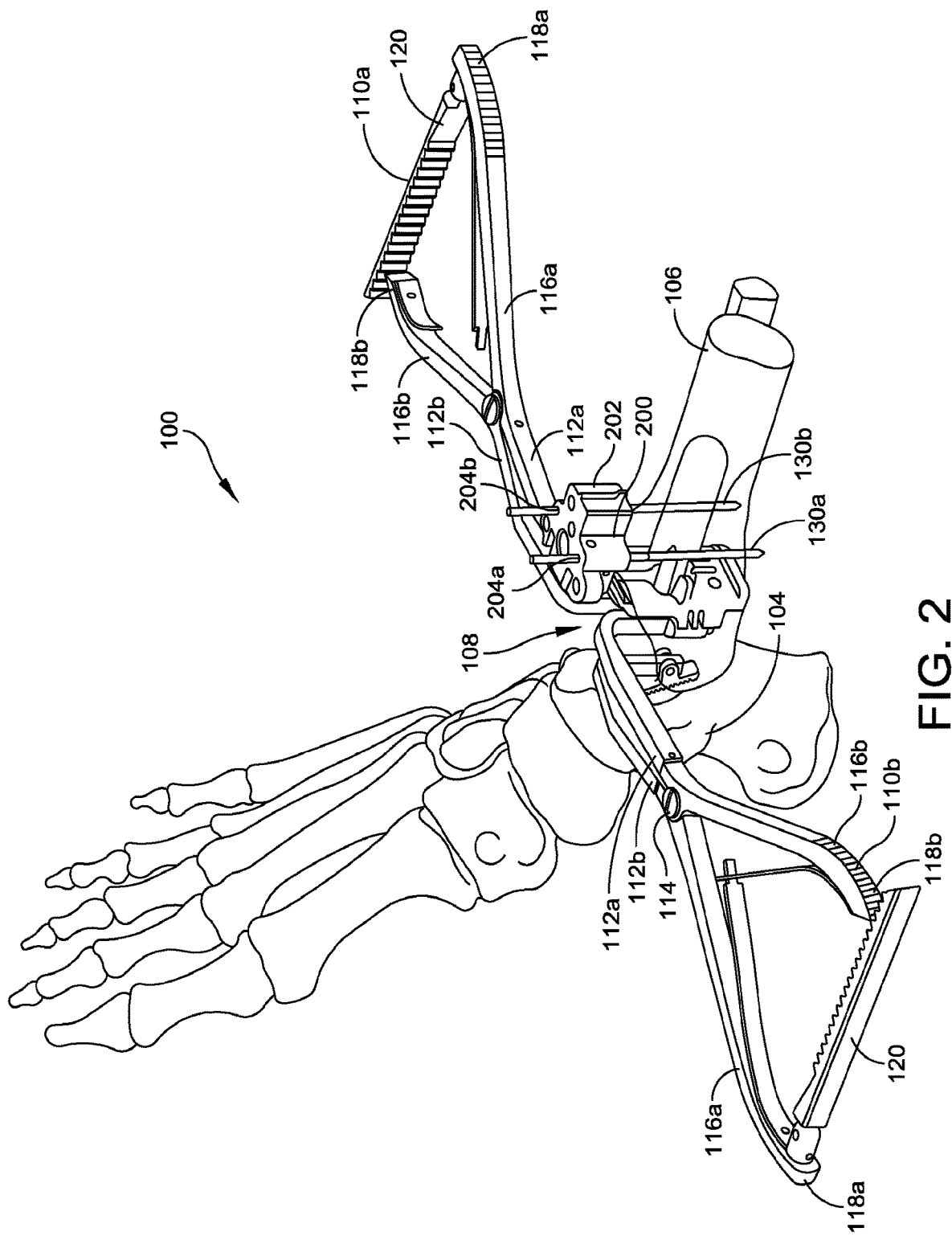
FIG. 2 illustrates a resected ankle joint having a broach guide coupled thereto, in accordance with some embodiments.
Figure 9:
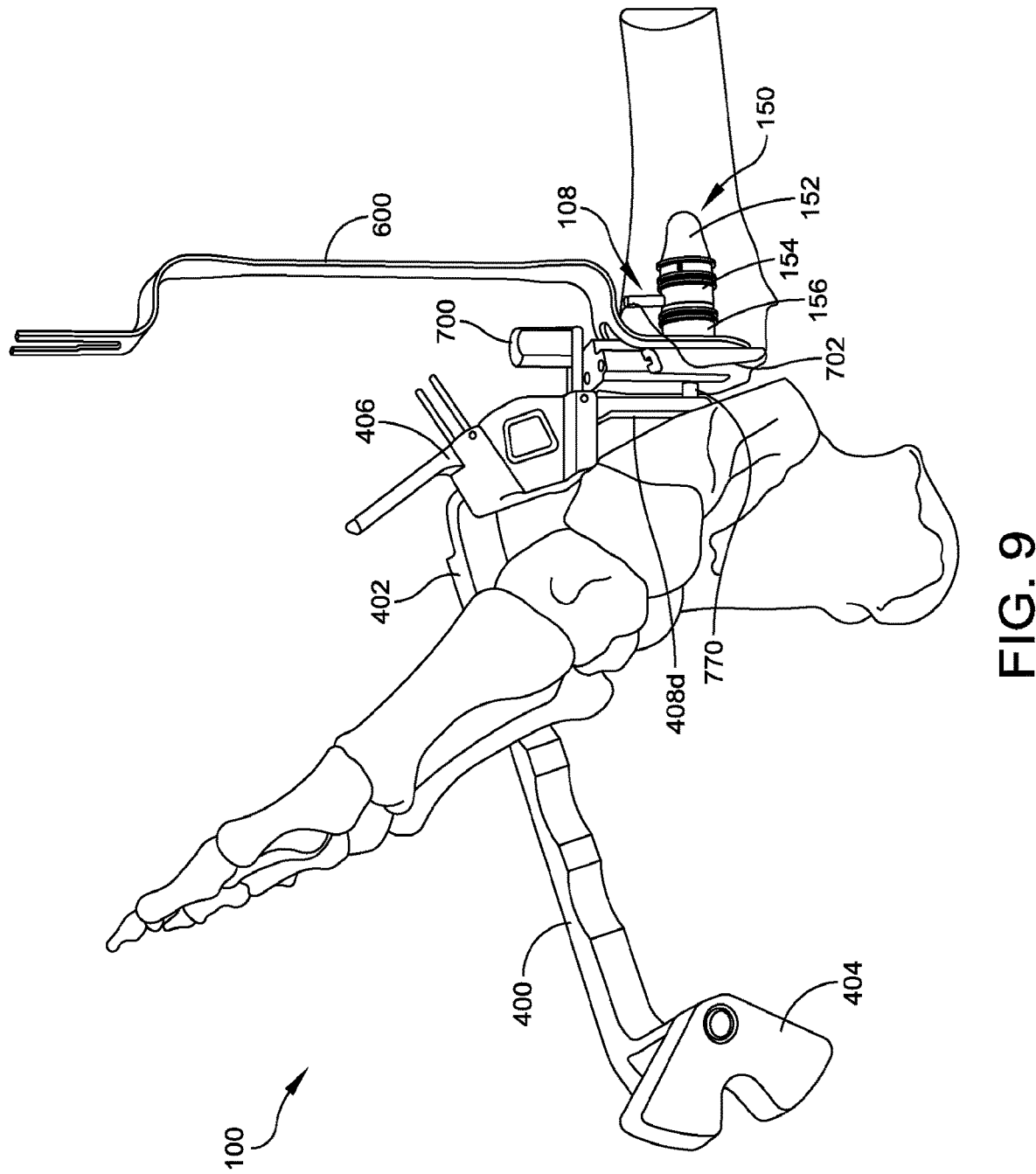
FIG. 9 illustrates the resected ankle joint of FIG. 8 having a tibial tray implant coupled to the offset impactor and a stem assembly, in accordance with some embodiments.
Figure 10:
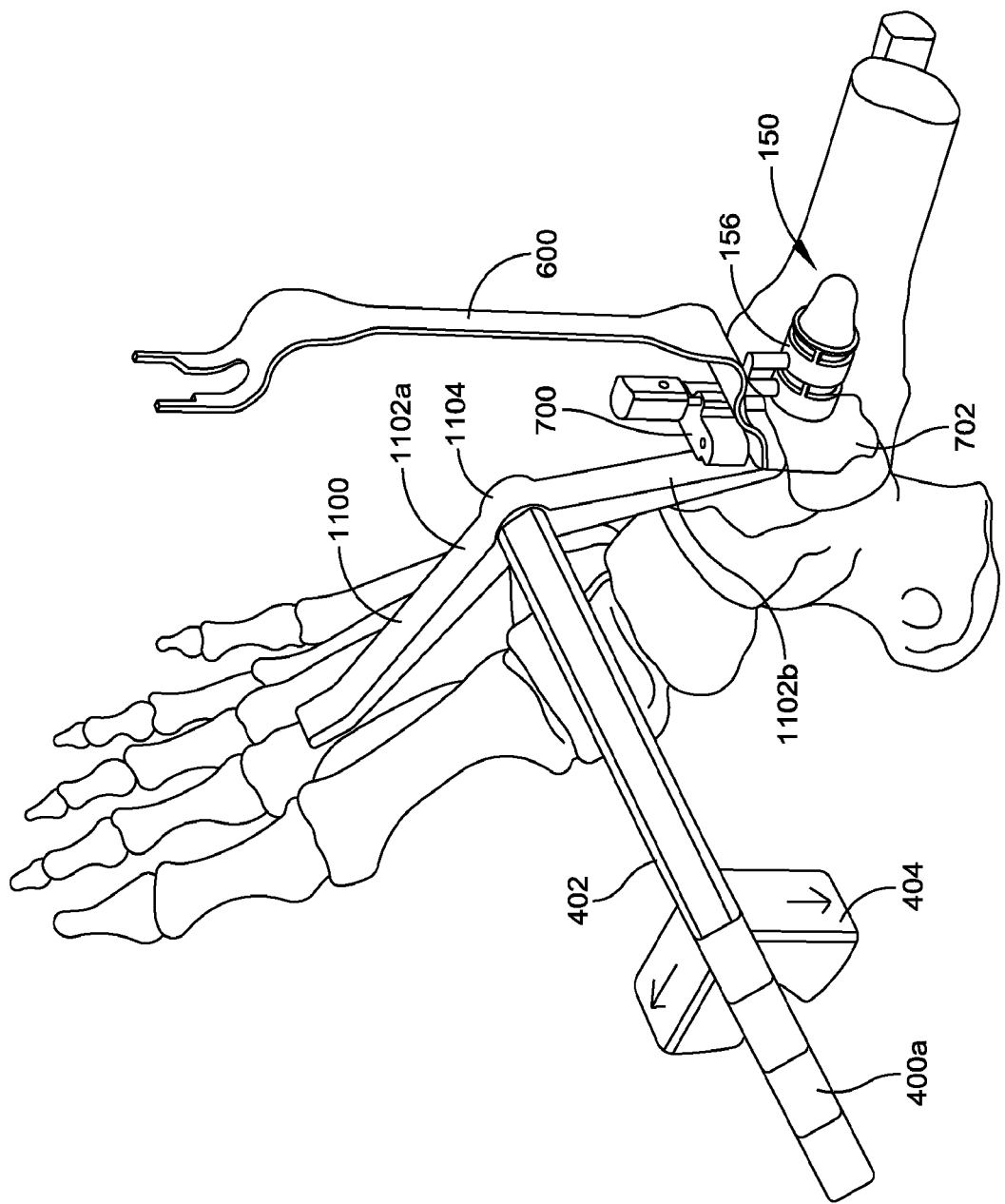
FIG. 10 illustrates the resected ankle joint of FIG. 9, having an offset impactor including an offset wrench coupled to the tibial tray implant, in accordance with some embodiments.
Figure 11:
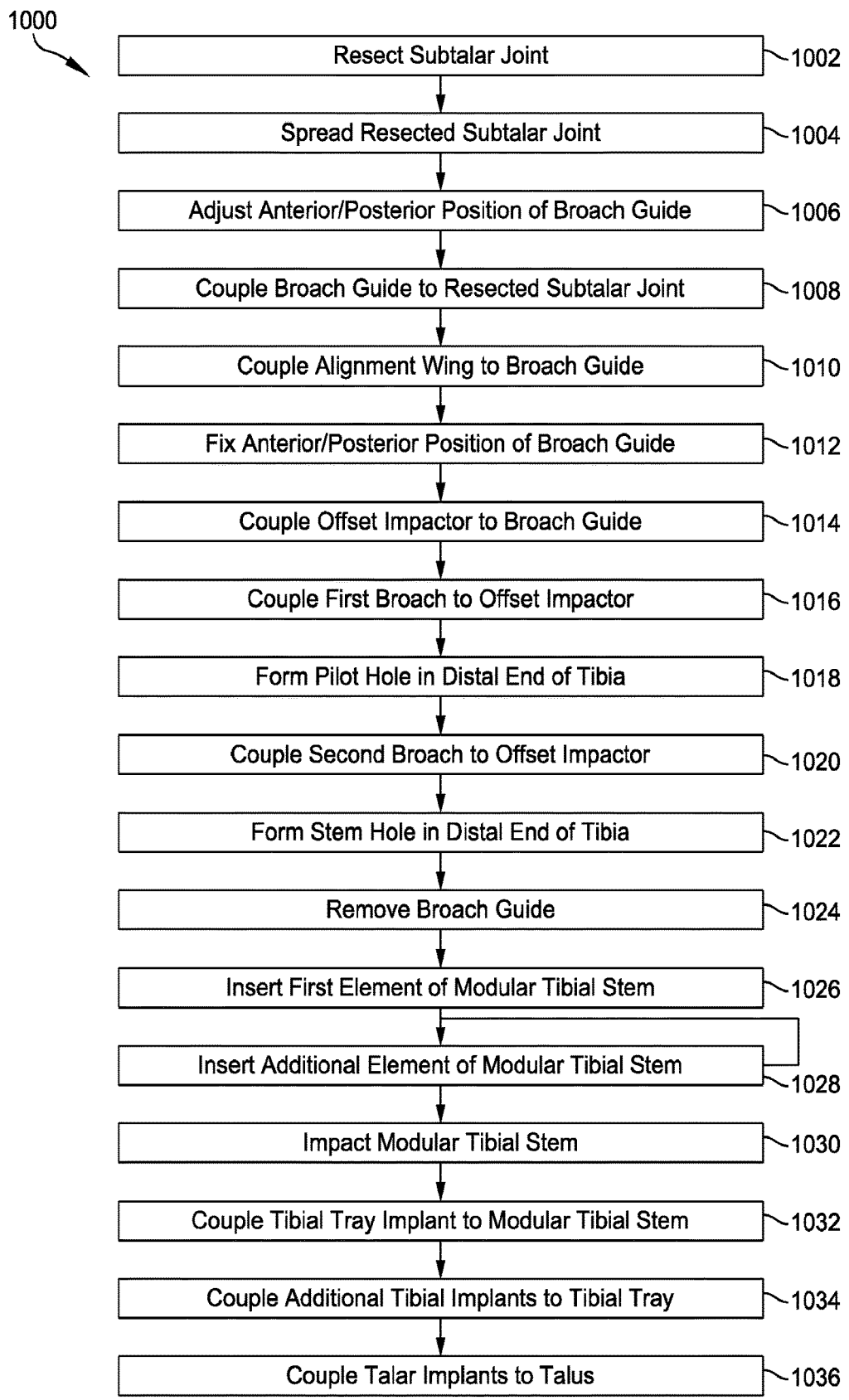
FIG. 11 is a flow chart illustrating an anterior ankle approach method of a total ankle replacement, in accordance with some embodiments.
Figure 12:
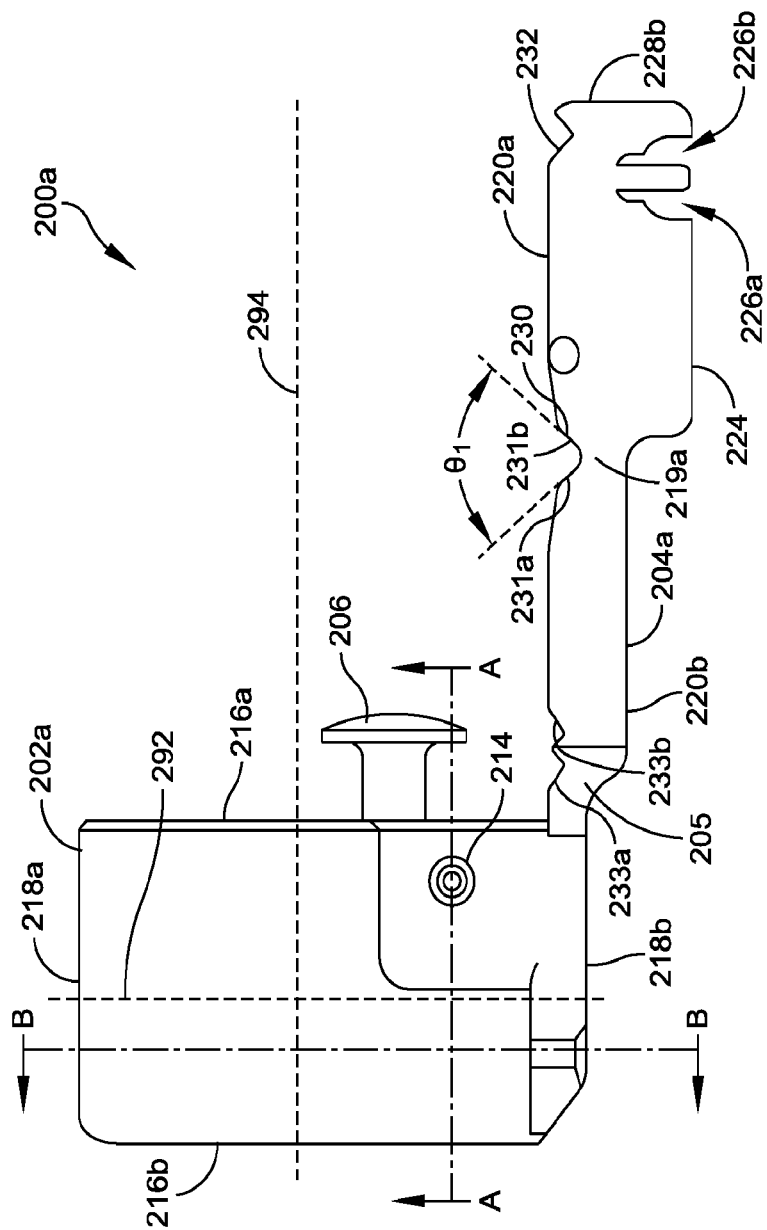
FIG. 12 illustrates a side view of a broach guide, in accordance with some embodiments.
Figure 14:
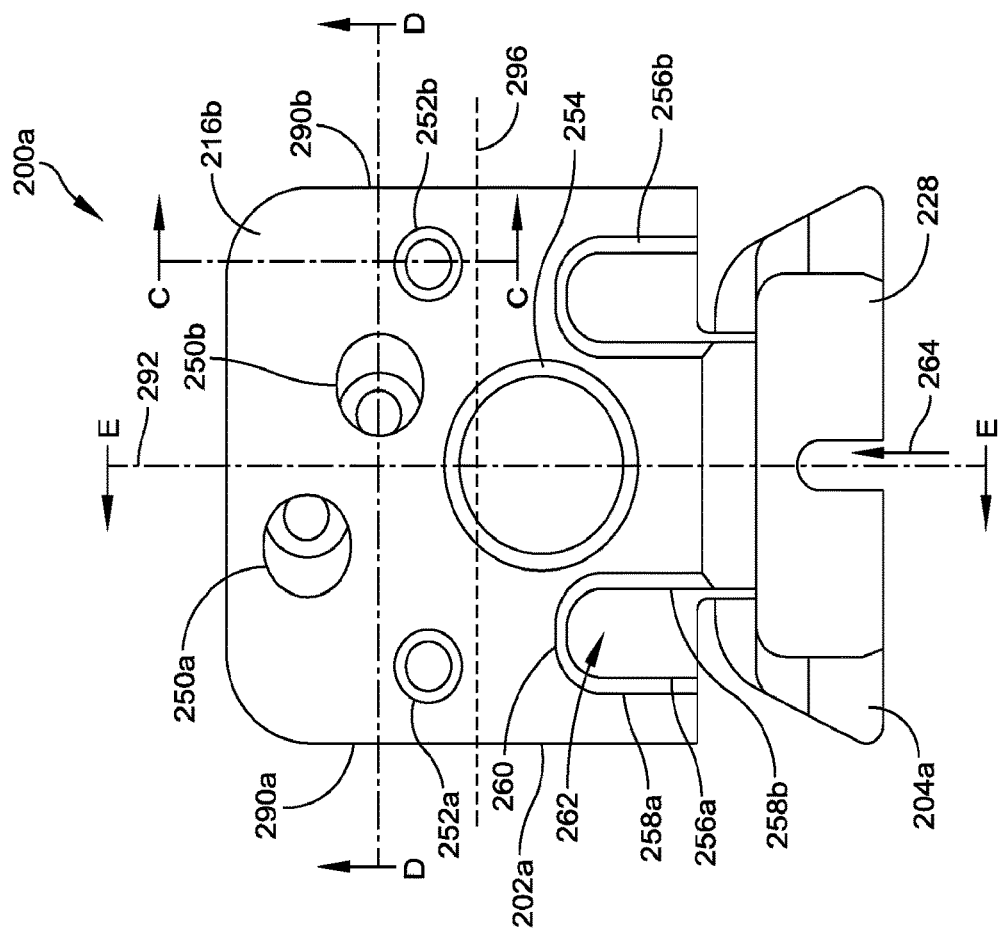
FIG. 14 illustrates a rear view of the broach guide of FIG. 12, in accordance with some embodiments.
Figure 13:
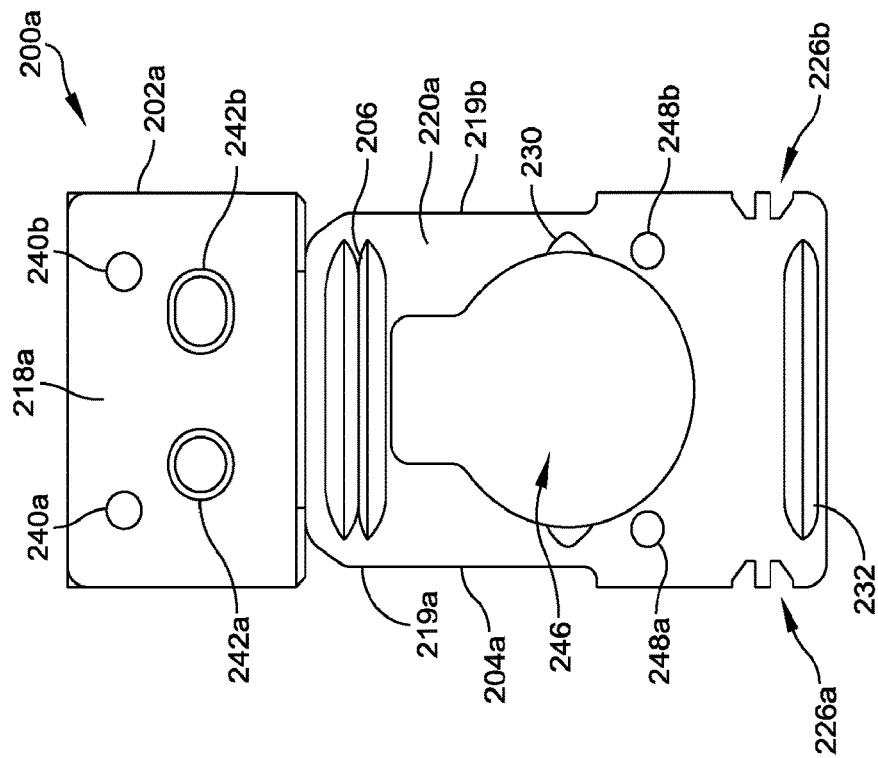
FIG. 13 illustrates a top-down view of the broach guide of FIG. 12, in accordance with some embodiments.
Figure 15:
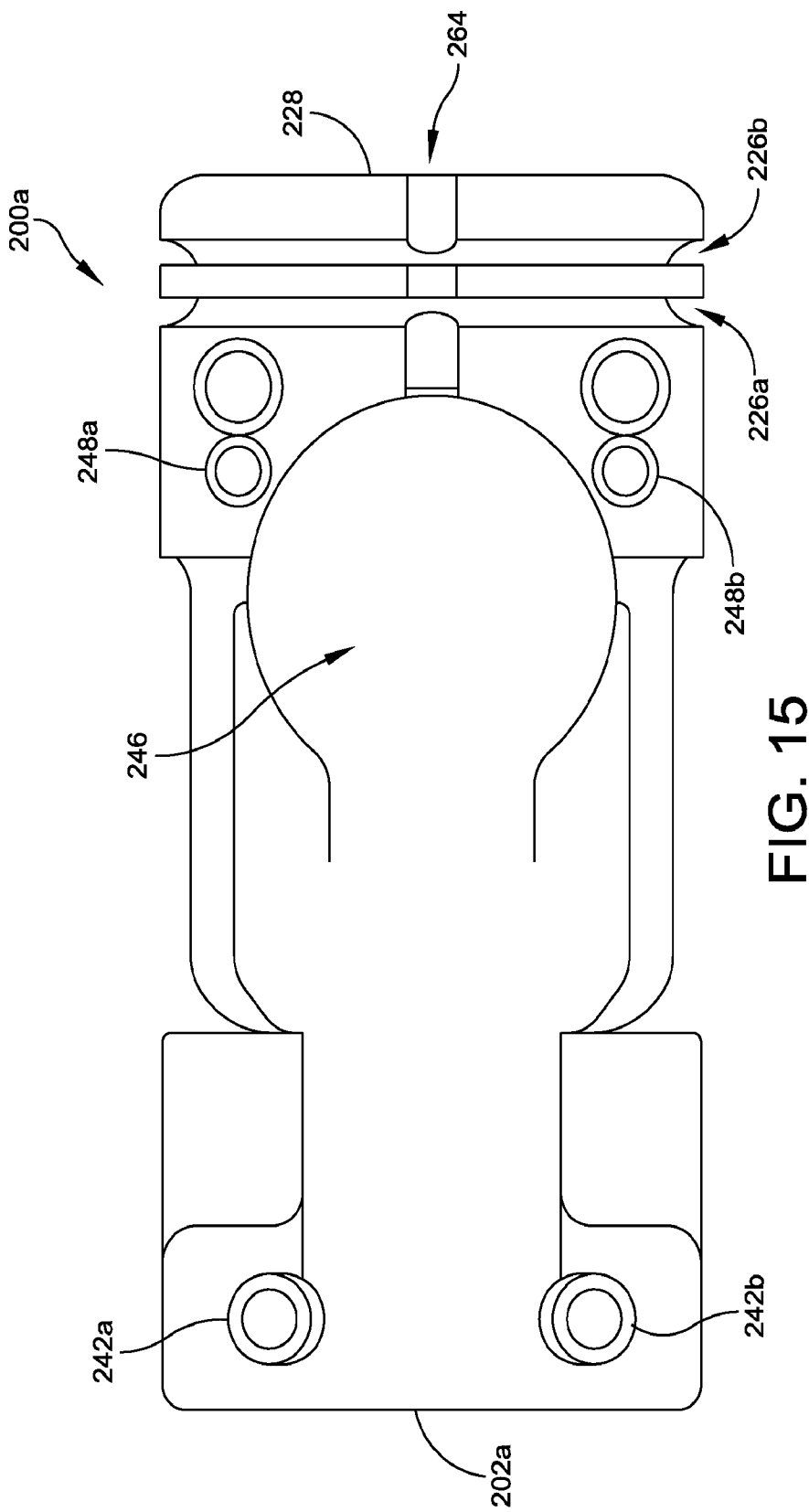
FIG. 15 illustrates bottom view of the broach guide of FIG. 12, in accordance with some embodiments.
Figure 17:
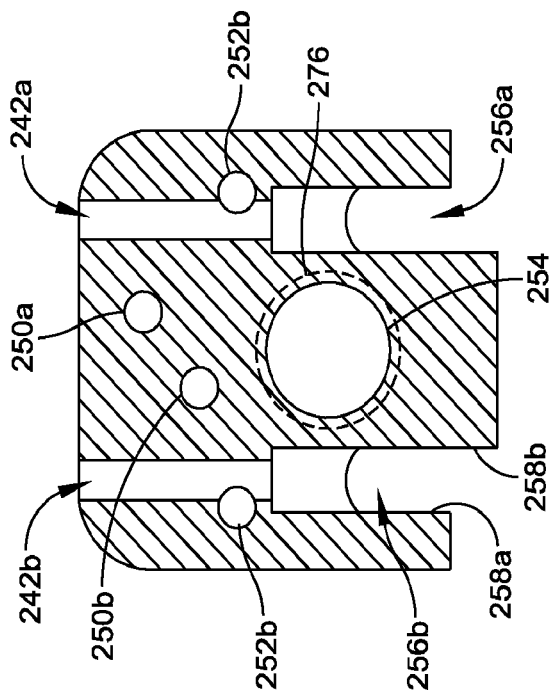
FIG. 17 illustrates a cross-sectional view of the broach guide taken along line B-B of FIG. 12, in accordance with some embodiments.
Figure 16:
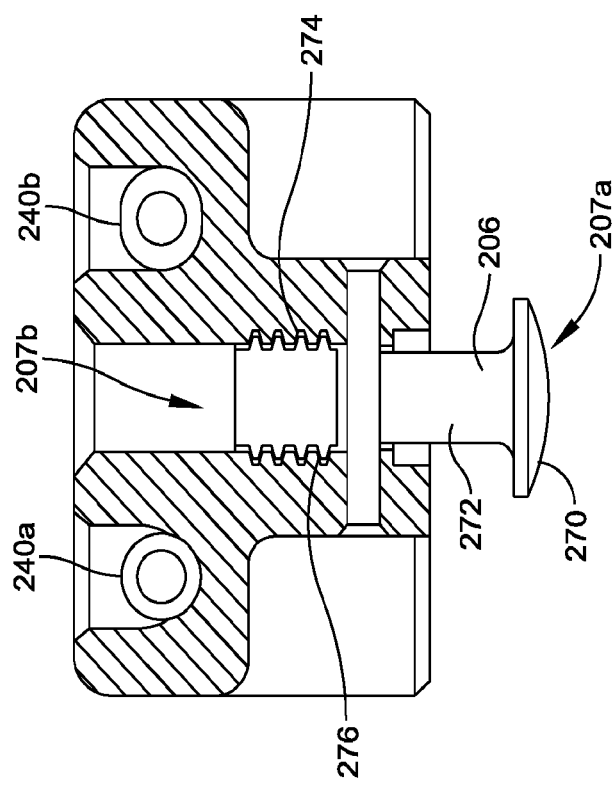
FIG. 16 illustrates a cross-sectional view of the broach guide taken along line A-A of FIG. 12, in accordance with some embodiments.

FIGS. 2-10 illustrate various steps of an anterior approach method 1000 configured to prepare a tibia for insertion of a tibial stem implant(s) and FIG. 11 is a flow chart illustrating an anterior ankle approach method 1000, in accordance with some embodiments. With reference now to FIGS. 2-11, the anterior approach method 1000 is discussed. At step 1002, the ankle joint 100 is resected. For example, as shown in FIG. 2, an ankle joint 100 including a talus 104 and a tibia 106, where the tibia 106 has a resection formed in an inferior (or distal) portion and a talar resection formed on a superior (or proximal) end of a talus 104. The resections can be formed according to one or more known methods.

At step 1004, one or more spreaders 110a, 110b are engaged with the resected tibial portion 108 to expand the resected portion 108 to increase a working area within the ankle joint 100. As shown in FIG. 2, the spreaders 110a, 110b each include a first spreading arm 112a and a second spreading arm 112b coupled in a pivoting engagement. The first spreading arm 112a and the second spreading arm 112b are positioned against abutting surfaces of the inferior resected portion 108 and are further separated to increase the working area within the ankle joint 100. For example, in some embodiments, the first and second spreading arms 112a, 112b of a first spreader 110a are coupled to a lateral side of the resected portion 108 and the first and second spreading arms 112a, 112b of a second spreader 110b are coupled to a medial side of the resected portion 108. In some embodiments, each of the spreading arms 112a, 112b extend are coupled to a pivot point 114. Handles 116a, 116b extend from the pivot point 114. In some embodiments, the handles 116a, 116b are formed integrally with the spreading arms 112a, 112b.

In use, the handles 116a, 116b are drawn together by an external force (such as a surgeon squeezing the handles 116a, 116b). A distal end 118a of the first handle 116a includes a ratcheting extension 120 and a distal end 118b of a second handle 116b is configured to engage the ratcheting extension 120. When a force is applied to the handles 116a, 116b, first and second spreading arms 112a, 112b are driven apart. The ratcheting extension 120 prevents the spreading arms 112a, 112b from compressing and spreads the resected tibial portion 108 to increase a working area.

At step 1006, a broach guide 200 is coupled to an anterior surface of the tibia 106. As shown in FIG. 2, the broach guide 200 includes a body 202. A lower edge of the body 202 can be positioned in an abutting relationship with the superior edge of the resected portion 108 such that the broach guide 200 is flush with the resected portion 108. The broach guide 200 can be coupled to the anterior surface of the tibia 106 by one or more temporary fixation elements 130a, 130b, such as, for example, k-wires, screws, pins and/or any other suitable temporary fixation element. In some embodiments, the temporary fixation elements 130a, 130b maintain a fixed lateral-medial position and a fixed superior-inferior position of the broach guide 200 with respect to the tibia 106, while allowing adjustment of the anterior/posterior position or alignment of the broach guide 200.

Figure 3:
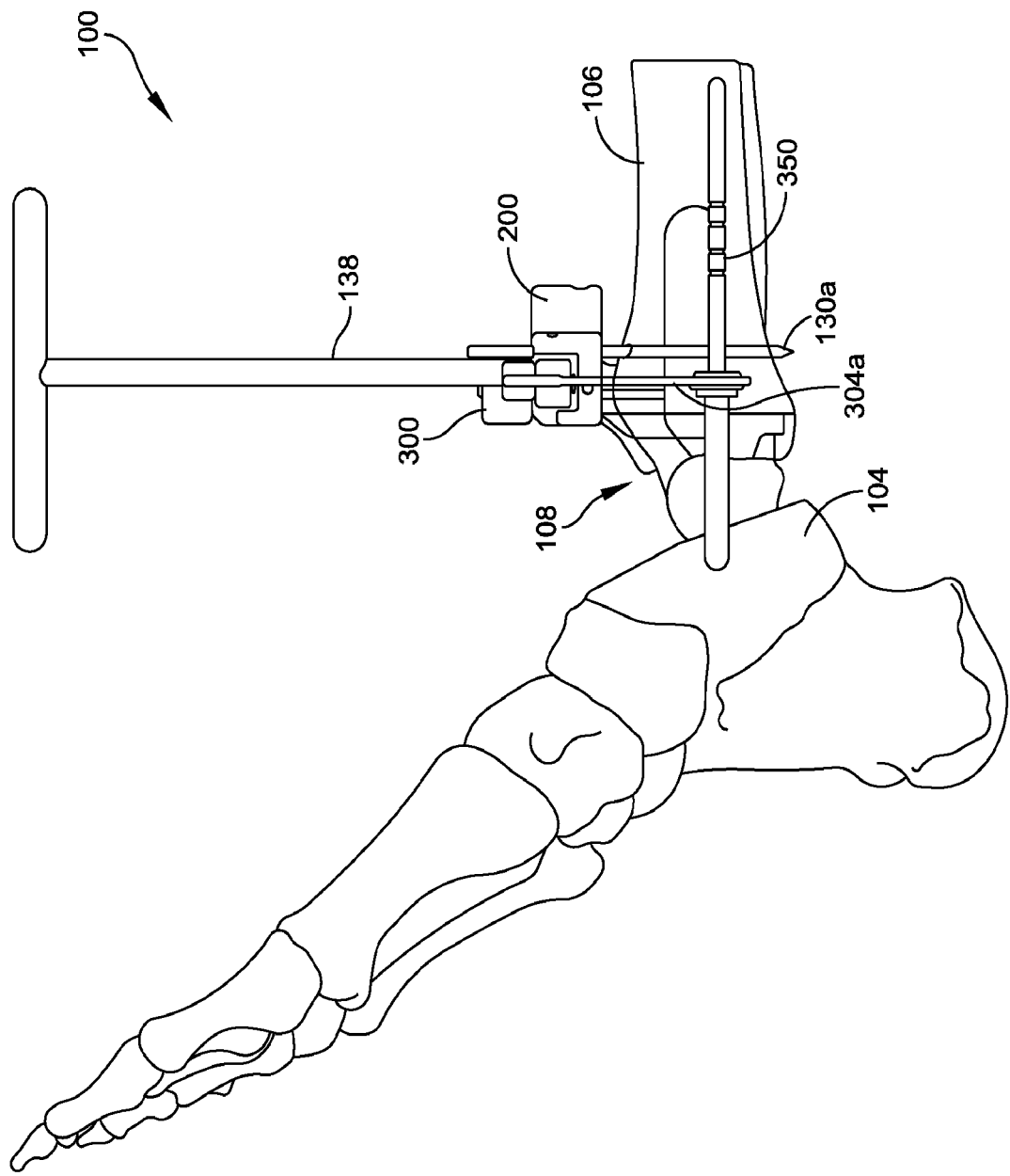
FIG. 3 illustrates the anterior ankle joint of FIG. 2 having an alignment wing and T-handle coupled to the broach guide, in accordance with some embodiments.
Figure 4:
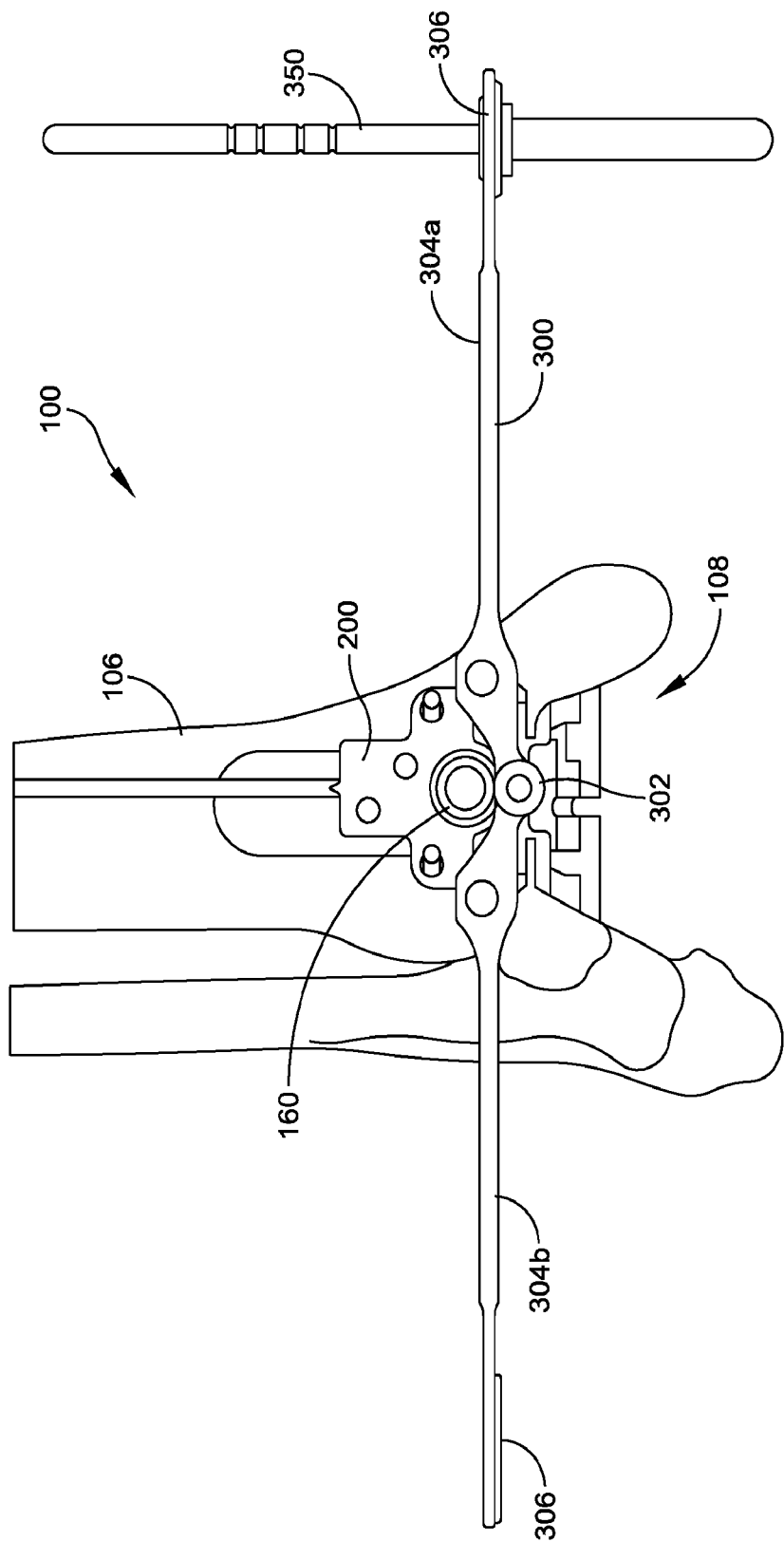
FIG. 4 illustrate an anterior view of the ankle joint of FIG. 3, in accordance with some embodiments.

At step 1008, an alignment wing 300 is coupled to the broach guide 200, as shown in FIGS. 3-4. The alignment wing 300 provides a visual indication of the position of the broach guide 200 with respect to the tibia 106, such as, for example, an anterior/posterior position of the broach guide 200. In some embodiments, the alignment wing 300 includes a body portion 302 configured to couple the alignment wing 300 to the broach guide 200. A first alignment arm 304a extends from the body portion 302 in a medial direction and a second alignment arm 304b extends from the body portion 302 in a lateral direction. Although embodiments are discussed herein including two alignment arms 304a, 304b, it will be appreciated that the alignment wing 300 can include a greater and/or lesser number of alignments arms, such as one alignment arm, three alignment arms, etc. Each of the alignment arms 304a, 304b include a rod receiving portion 306 that curves from the alignment arms 304a, 304b in a posterior direction. The rod receiving portion 306 includes a hole 314 (see FIG. 25) sized and configured to receive an alignment rod 350 therethrough. The alignment rod 350 extends through the rod receiving portion 306 and indicates the anterior/posterior position of the broach guide 200 with respect to the tibia 106. In some embodiments, an alignment rod 350 is coupled to the broach guide 200 to provide a visual indicator of the medial/lateral position and/or the anterior/posterior alignment of the broach guide 200. In some embodiments, the alignment rod 350 includes one or more indicators corresponding to a length of a stem insert and/or one or more components of a multi-component stem insert.

At step 1010, the anterior/posterior position of the broach guide 200 can be adjusted. For example, in some embodiments, a wrench 138 is configured to adjust an anterior/posterior position of the broach guide 200 with respect to the tibia 106. The wrench 138 can be inserted into an adjustment hole 254 formed in the broach guide 200 (as discussed in greater detail below with respect to FIGS. 12-23). For example, in some embodiments the broach guide 200 includes an anterior/posterior adjustment screw 206a. The adjustment screw 206a includes a driver head cavity sized and configured to receive the wrench 138 therein. Rotation of the wrench 138 causes advancement of the adjustment screw 206a in the anterior/posterior direction and further provides adjustment of the broach guide 200 in the same direction.

At step 1012, the anterior/posterior position of the broach guide 200 is fixed. For example, in some embodiments, a temporary AP (anterior/posterior) fixation device 136 is inserted through an angled fixation hole 250a, 250b formed in the broach guide 200 (see FIG. 14). The temporary AP fixation device 136 includes a shaft having a sharpened end configured to penetrate the tibia 106 and a stop 140 fixedly coupled to the shaft. The stop 140 is configured to abut the broach guide 200 to prevent anterior/posterior movement of the broach guide 200 when the temporary AP fixation element 136 is coupled to the tibia 106. The temporary AP fixation element 136 can include any suitable temporary fixation element, such as a pin, screw, k-wire, and/or any other suitable element. The stop 140 can include any suitable surface configured to maintain the broach guide 200 in a fixed position, such as a screw or pin head, a washer coupled to a k-wire, and/or any other suitable element. In some embodiments, the broach guide 200 includes a locking feature configured to maintain the broach guide 200 in a fixed position and prevent anterior/posterior movement of the broach guide 200. In some embodiments, a plurality of fixation elements, such as a plurality of pins, screws, etc., are configured to maintain the broach guide 200 in a fixed position.

At step 1014, an offset impactor 400 is coupled to the broach guide 200. The offset impactor 400 can include an offset shaft 402 having an impactor head 404 disposed at a first end and an impactor body 406 coupled to a second end. The impactor body 406 is configured to transfer an impaction force applied to the impactor head 404 to an impaction arm 408 extending from the impactor body 406 into the resected tibial portion 108. The offset shaft 402 of the offset impactor 400 is configured to position an impactor head 404 below an inferior surface of a foot and an impactor body 406 in alignment with the resected tibial portion 108. In some embodiments, the offset impactor is coupled to the broach guide 200 by one or more spring-loaded coupling pins 486a, 486b inserted into slots 256a, 256b and/or holes forms in the broach guide 200, as discussed in greater detail with respect to FIGS. 32-37. In some embodiments, the coupling pins 486a, 486b are not spring-loaded.

At step 1016, a first broach 500 is coupled to a distal end of the impaction arm 408. The first broach 500 can be coupled to the impaction arm 408 prior to, during, and/or subsequent to coupling the offset impactor 400 to the broach guide 200. The first broach 500 is positioned by the impaction arm 408 to pass through a broach guide hole formed in a guide body of the broach guide 200, as discussed in greater detail with respect to claims 12-21. In some embodiments, the first broach 500 is a pilot broach including a broach head having a plurality of cutting features defining one or more cutting edges, such as, for example, flutes, sharpened edges, teeth, and/or any other suitable cutting feature.

At step 1018, an impaction force is applied to the impactor head 404 to drive the first broach 500 into contact with a distal end of the tibia 106 (e.g., a superior surface of the resected tibial portion 108). The first broach 500 forms a first hole, or pilot hole, through the distal end of the tibia 106.

At step 1020, the first broach 500 is removed from the impaction arm 408 and a second broach 550 is coupled to the impaction arm 408. The second broach 550 is coupled to the impaction arm 408 and is positioned to be inserted into the pilot hole formed by the first broach 500. In some embodiments, the second broach 550 is an enlarging broach including a broach head having a plurality of cutting features defining a plurality cutting paths, as discussed in greater detail with respect to FIGS. 46-47. The first broach 500 and/or the second broach 550 can be configured to form a hole through any suitable cutting method, such as reaming, boring, drilling, lapping, etc.

At step 1022, an impaction force is applied to the impactor head 404 to drive the second broach 550 into contact with a superior surface of the resected tibial portion 108. The second broach 550 enlarges the pilot hole formed by the first broach 500. In some embodiments, the second broach 550 forms a stem hole 160 sized and configured to receive a tibial implant, such as tibial stem (modular and/or non-modular). In other embodiments, one or more additional enlarging broaches having a diameter greater than or equal to the second broach 550 are attached to the offset impactor 400 and impacted to enlarge and/or deepen the hole formed in the distal end of the tibia 106.

At step 1024, the broach guide 200 and/or the offset impactor 400 (including an attached broach 550) are removed from the resected tibial portion 108. The broach guide 200 can be removed from the resected tibial portion 108 by removing the temporary fixation elements 130a, 130b, 136 from the tibia. In some embodiments, the offset impactor 400 is temporarily removed from the tibia 106 and is used in subsequent steps of the method 1000.

Figure 7:
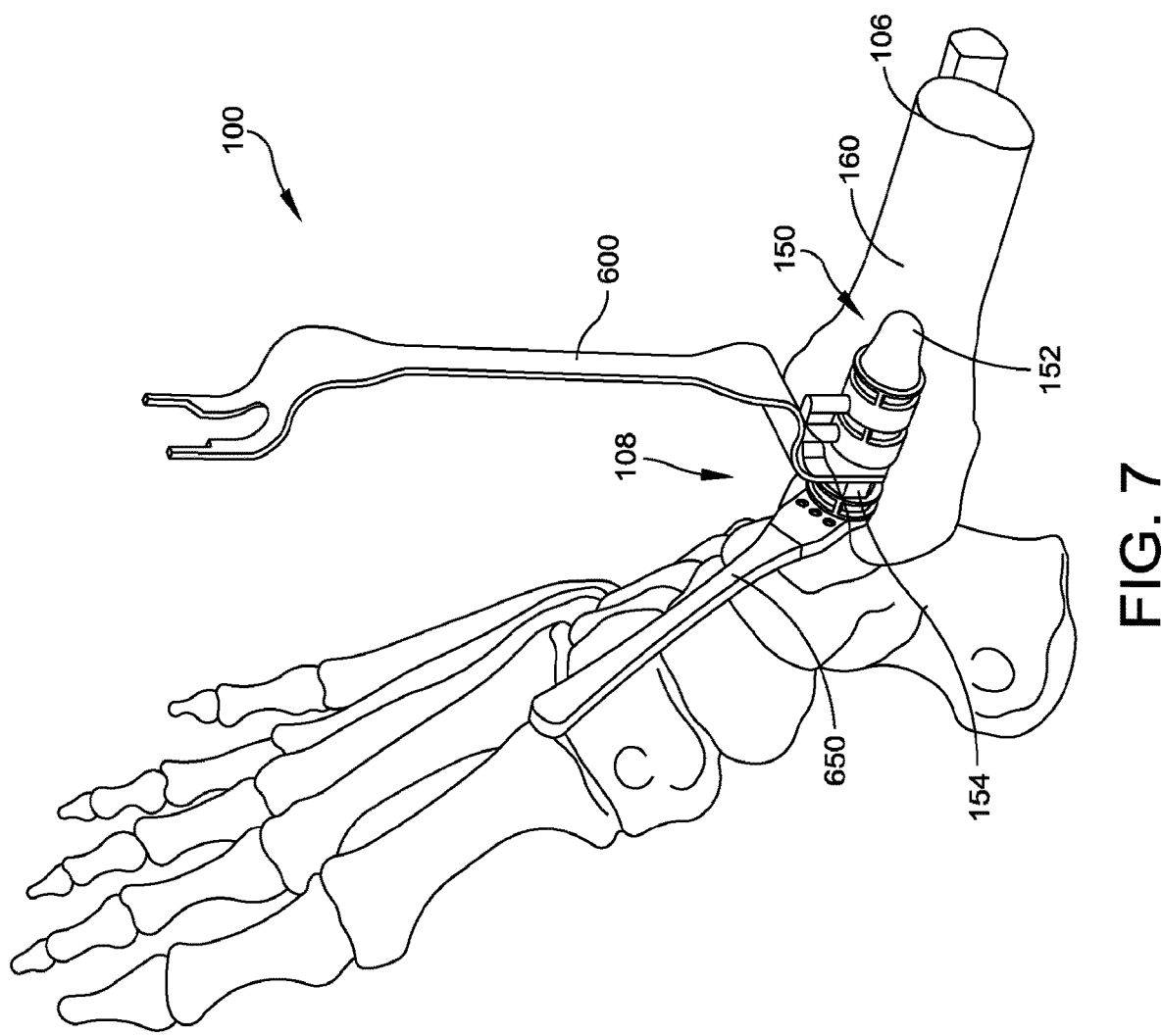
FIG. 7 illustrates the resected ankle joint of FIG. 6 having a stem assembly inserted into a stem hole formed in a tibia by the offset impactor, in accordance with some embodiments.
Figure 8:
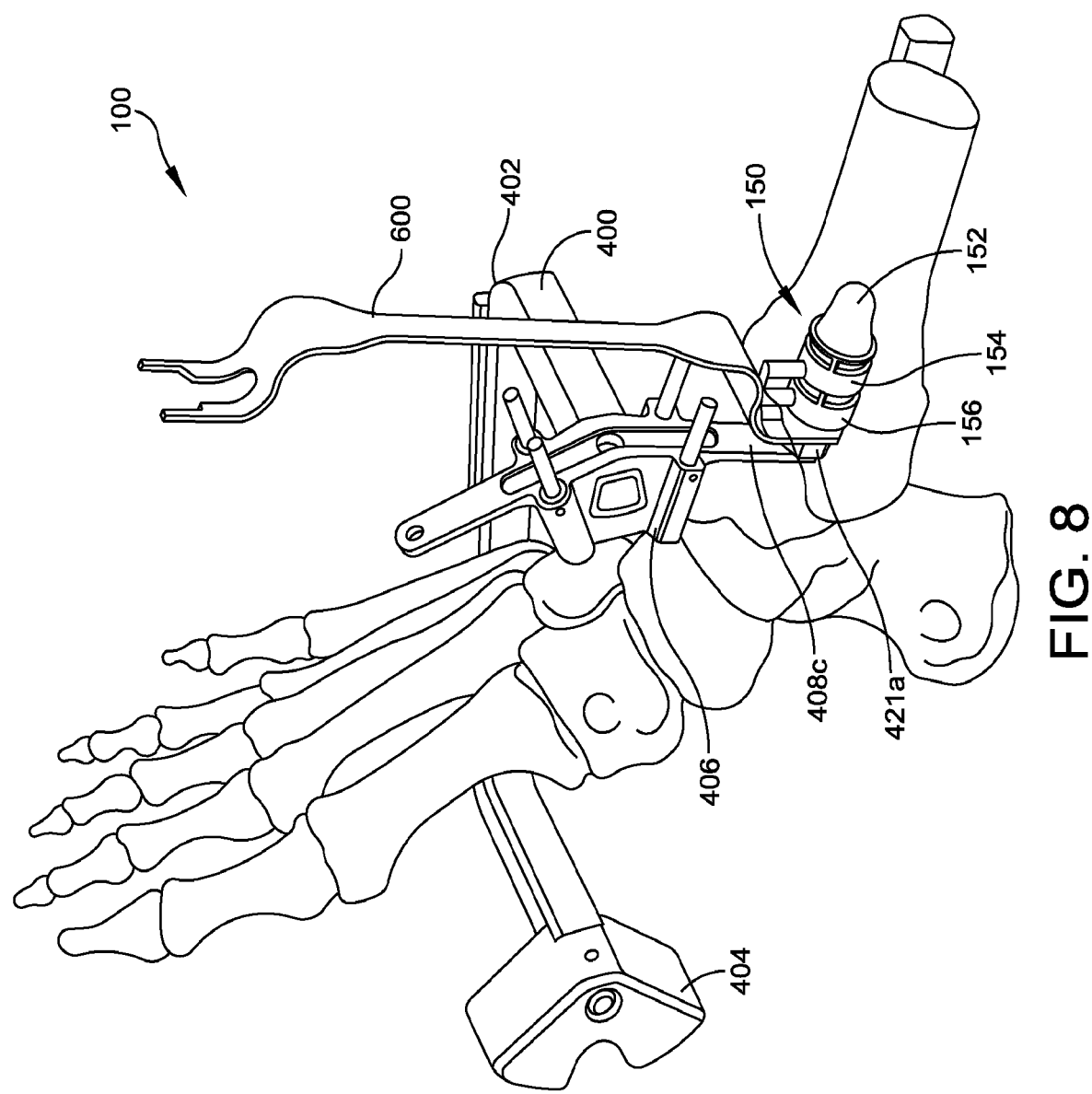
FIG. 8 illustrates the resected ankle joint of FIG. 7 having an offset impactor coupled to the stem assembly inserted into the stem hole, in accordance with some embodiments.

At step 1026, a first element 152 of a modular tibial stem 150 is positioned at least partially within the stem hole 160 formed by the first broach 500, the second broach 550, and/or any additional broaches. As shown in FIG. 7, the first element 152 is sized and configured to be fully inserted into the enlarged hole 160. The first element 152 is positioned within the stem hole 160 by inserting the first element 152 through the anterior tibial resection 108 and without forming a hole in and/or displacing the talus or other foot bones. The insertion of the modular tibial stem 150 using the anterior ankle approach discussed herein advantageously maintains the integrity of the foot and talus 104 during a total ankle replacement procedure. Although embodiments are discussed herein including a modular stem 150, it will be appreciated that the disclosed systems and methods can be used with a monolithic stem and are within the scope of this disclosure.

At step 1028, a second element 154 of the modular tibial stem 150 is inserted through the anterior tibial resection 108. The second element 154 is positioned at least partially in and/or aligned with the stem hole 160. The upper surface of the second element 154 is coupled to the lower surface of the first element 152. In some embodiments, the second element 154 is coupled to the first element by a threaded and/or other rotatable engagement mechanism, although it will be appreciated that any suitable engagement mechanism can be used. For example, in various embodiments, a rotational coupling mechanism (such as a threaded coupling), a press or force coupling mechanism, an adhesive coupling mechanism, and/or any other suitable coupling mechanism can be used to couple the first stem component 152 to the second stem component 154.

In some embodiments, an offset wrench 600 and/or an offset driver 650 are configured to couple the second stem component 154 to the first stem component 152. For example, as shown in FIG. 7, an offset wrench 600 can be coupled to a first stem component 152 to maintain the first stem component in a fixed rotational position. An offset driver 650 can be coupled to the second stem component 154 to rotate the second stem component 154 with respect to the first stem component 152. As shown in FIG. 7, in some embodiments, the offset driver 650 defines a ratcheting driver having a head sized and configured to be inserted into a cavity formed in the second stem component 154. In other embodiments, the ratcheting driver 650 defines a head sized and configured to be received at least partially over an outer surface of the second stem component 154. The outer surface of the second stem component 154 can define one or more drive surfaces configured to couple the offset driver 650 to the second stem component 154. Rotation of the offset driver 650 in a first direction causes rotation of the second stem component 154 in the same direction. In some embodiments, the head includes a ratcheting element such that rotation of the offset driver 650 in a second direction does not cause rotation of the second stem component 154. In other embodiments, the offset driver 650 can include a driver shaft coupled to a driver head having a drive bit disposed at an angle with respect to the driver shaft. The drive bit is sized and configured for insertion into a driver cavity formed in a lower surface of the second stem component 154. Pivoting movement of the offset driver 650 in a first direction causes rotation of the second stem component 154. In some embodiments, the driver head includes a gear engagement such that movement of the offset driver 650 in a second direction causes rotation of the second stem component 154 in the same direction. Although an offset wrench 600 and an offset driver 650 are illustrated, it will be appreciated that any suitable tool can be used to couple the first stem component 152 to the second stem component 154.

Additional elements 156 of the modular tibial stem 150 can be positioned at least partially in and/or aligned with the stem hole 160 and coupled to the proximal end of the modular tibial stem 150. The additional stem components 156 can be coupled to the modular tibial stem 150 using any suitable coupling mechanism. In some embodiments, the additional stem components 156 can be coupled to the stem 150 using a similar coupling mechanism as the first stem component 152 and the second stem component 154 or can utilize a different coupling mechanism, such as, for example, a press-fit coupling mechanism. In some embodiments, the additional elements 156 of the modular tibial stem 150 are coupled to the second element 154 using the offset wrench 600 and/or the offset driver 650.

At step 1030, the offset impactor 400 is coupled to the modular tibial stem 150 to provide an impaction force to the modular tibial stem 150, as shown in FIG. 9. In some embodiments, a stem impactor arm 408*d* is coupled to the impactor housing 406 at a first end and an impactor element 770 at a second end. The impactor element 770 is configured to transfer an impaction force from the impactor body 406 (applied to an impactor head 404 coupled to the impactor body 406 by an offset shaft 402) to the tibial stem 150.

Figure 61:
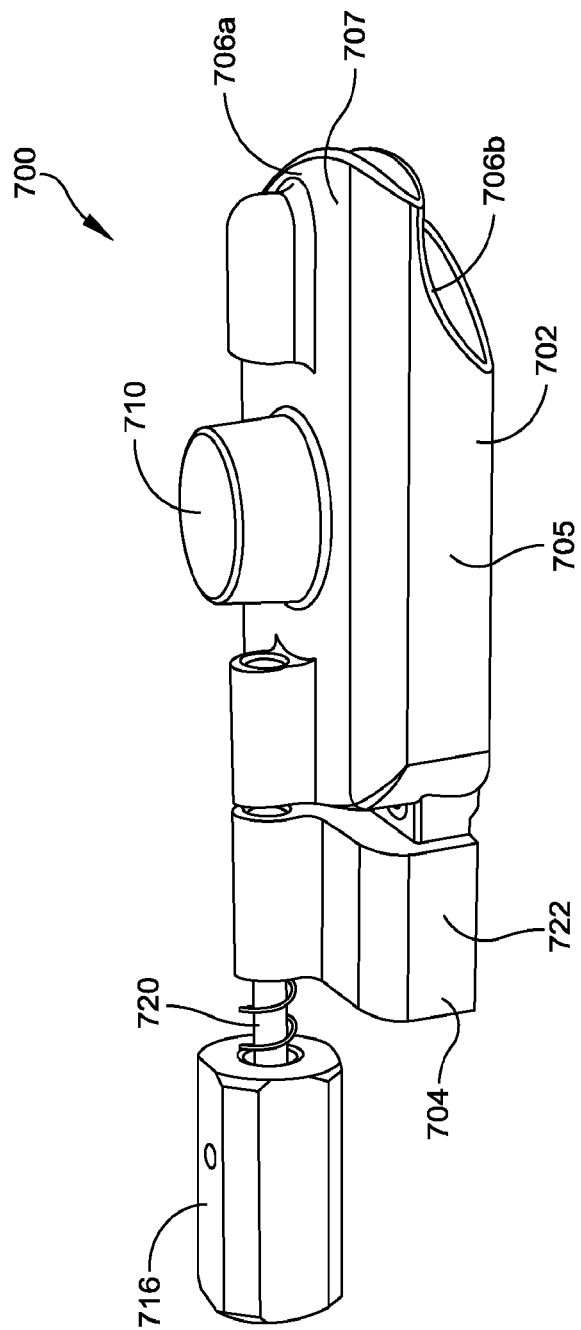
FIG. 61 is a side perspective view of an implant assembly, in accordance with some embodiments.

At step 1032, a tibial tray 702 is coupled to an inferior element of the modular tibial stem 150. For example, in some embodiments, the tibial tray 702 is coupled a third stem component 156, although it will be appreciated that the tibial tray 702 can be configured to be coupled to any of the tibial stem components 152-156 of the modular tibial stem 150. The tibial tray 702 includes a coupling element 710 (see FIG. 61) configured to be inserted into the inferior-most stem component 156 of the tibial stem 150. For example, in some embodiments, an inferior end of the modular tibial stem 150 includes a cavity (not shown) sized and configured to receive the coupling element 710 in a press-fit engagement, such as a Morse taper engagement. In other embodiments, the tibial tray 702 can be coupled to the modular tibial stem 150 using any suitable coupling element, such as a pin, a threaded screw, a force-fit engagement, and/or any other suitable coupling element.

In some embodiments, the tibial tray 702 is coupled to the inferior element 156 of the tibial stem 150 by the offset impactor 400. The tibial tray 702 can include a first surface having a coupling element 710 extending therefrom and a second surface configured to engage a tibial tray insert 700. The tibial tray insert 700 has a first surface configured to engage the tibial tray 702 and a second surface configured to engage an impactor arm 408*d* of the offset impactor 400. An impaction force is applied to the offset impactor head 404 and transferred to tibial tray insert 700 and the tibial tray 702. The impaction force drives the coupling element 710 into a press-fit engagement with the inferior element 156 of the tibial stem 150. The offset impactor 400 can be removed from the tibia 106 after impacting the tibial tray 702 into the tibial stem 150.

At step 1034, one or more tibial implants are coupled to the tibial tray 702 through the anterior tibial resection 108. The one or more additional implants can include, but are not limited to, an articulation surface, a spacing insert, and/or any other suitable tibial implants.

At step 1036, one or more talar implants are coupled to the talus 104. The one or more talar implants can include, but are not limited to, an articulation surface (such as a talar dome), a coupling plate, and/or any other suitable talar implants.

FIGS. 12-20 illustrate one embodiment of a broach guide 200*a*, in accordance with some embodiments. The broach guide 200*a* is similar to the broach guide 200 discussed in conjunction with FIGS. 2-11, and similar descriptions are not repeated herein. The broach guide 200*a* includes a body 202a extending between a bone contact surface 216a, an outer surface 216b, a superior surface 218a, an inferior surface 218b, and side surfaces 290a, 290b. In some embodiments, the body 202a can have a generally rectangular cuboid shape defined by the surfaces 216a-218b, 290a-290b, although it will be appreciated that the body 202a can have any suitable shape defined by one or more surfaces 216a-218b, 290a-290b. In the illustrated embodiments, a vertical axis 292 of the body 202a extends from the superior surface 218a to the inferior surface 218b, a longitudinal axis 294 extends from the bone facing surface 216a to the outer surface 216b, and a transverse axis 296 extends from the first side surface 290a to a second side surface 290b. In some embodiments, the body 202a defines a plurality of holes extending from one or more surfaces at least partially into the body 202a.

In some embodiments, a first set of holes 240a-240b and a second set of holes 242a-242b extend from the superior surface 218a of the body 202a along a vertical axis 292 of the body 202. The first set of holes 240a-240b extend from the superior surface 218a to an inferior surface 218b. In some embodiments, each hole of the first set of holes 240a-240b are configured to assist in sterilization of the body 202.

In some embodiments, the second set of holes 242a-242b each comprise a guide hole each sized and configured to receive an alignment wing 300, 300a therethrough. The alignment wing posts 310a, 310b are sized and configured be inserted into the guide holes 242a-242b of the broach guide 200 to provide a visual indication to a user (such as a surgeon) regarding medial/lateral alignment and/or the anterior/posterior location of the guide 200 with respect to a tibia 106. In some embodiments, the guide holes 242a, 242b extend from a superior surface 218a of the body 202 to an inferior surface 218b.

In some embodiments, a first slot 256a and a second slot 256b are defined in the body 202a. The first and second slots 256a, 256b extend from the bone contact surface 216a to the outer surface 216b and extend into the body 202a from the inferior surface 218b. The slots 256a, 256b are sized and configured to receive guide rods 486a, 486b therein. The sidewalls 258a, 258b of the first and second slots 256a, 256b define an opening larger than a width of the guide rods 486a, 486b. The guide rods 486a, 486b extend into the guide holes 242a, 242b and maintain the anterior/posterior and medial/lateral positioning of the impactor body 406, while permitting inferior-superior movement of the impactor body 406, for example, to transfer an impaction force to an impactor arm 408.

In some embodiments, the guide rods 486a, 486b are inserted into the slots 256a, 256b from the outer surface 216b towards the bone contact surface 216a. Insertion of the guide rods 486a, 486b into the slots 256a, 256b allows the impactor body 406 of the offset impactor 400 to be positioned in the resected portion 108 using anterior to posterior movement. Insertion of the impactor body 406 using anterior to posterior movement advantageously allows the impactor body 406 to be positioned within the resected portion 108 through the anterior opening and without needing to remove additional sections of the tibia and/or the talus to allow superior/inferior movement during insertion.

In some embodiments, the body 202a defines a plurality of parallel pin holes 252a-252b and one or more angled pin holes 250a-250b extending from the outer surface 216b to the bone contact surface 216a. The plurality of parallel pin holes 252a-252b each extend through the body along a hole axis that is aligned with the longitudinal axis 294 of the body. The parallel pin holes 254a, 254b are sized and configured to receive temporary fixation elements 130a, 130b therethrough to couple the body 202a to an anterior surface of a tibia 108, as illustrated in FIG. 2. The temporary fixation elements 130a, 130b can include any suitable temporary fixation device, such as, for example, a k-wire, a pin, a screw, and/or any other suitable temporary fixation element. The temporary fixation elements 130a, 130b are configured to fix the lateral-medial position and/or the superior-inferior position of the broach guide 200a with respect to a tibia 106, while permitting movement of the broach guide 200a in an anterior/posterior direction.

Figure 19:
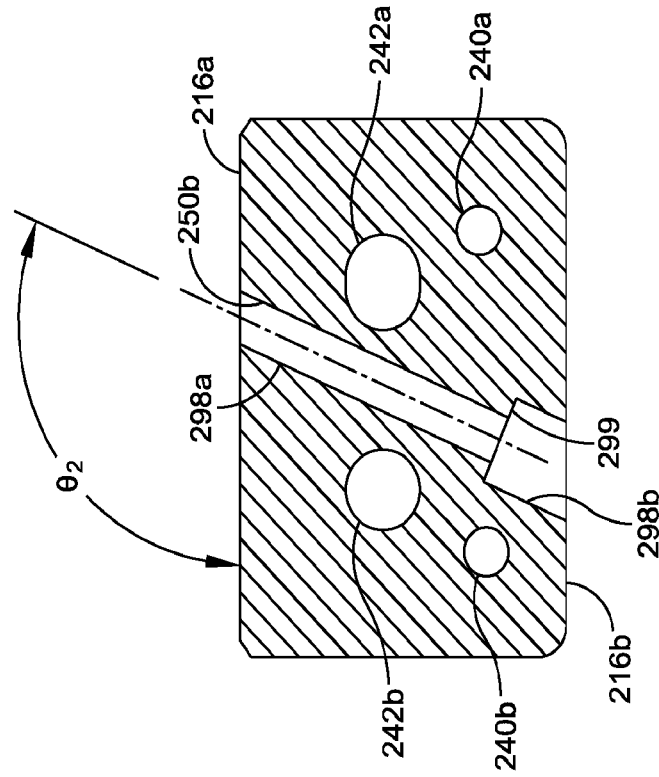
FIG. 19 illustrates a cross-sectional view of the broach guide taken along line D-D of FIG. 14, in accordance with some embodiments.
Figure 18:
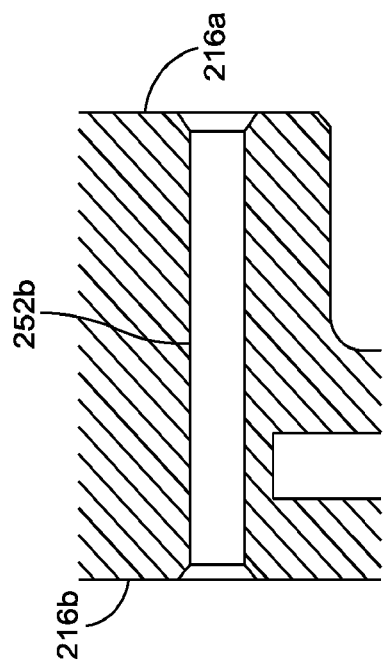
FIG. 18 illustrates a cross-sectional view of the broach guide taken along line C-C of FIG. 14, in accordance with some embodiments.
Figure 20:
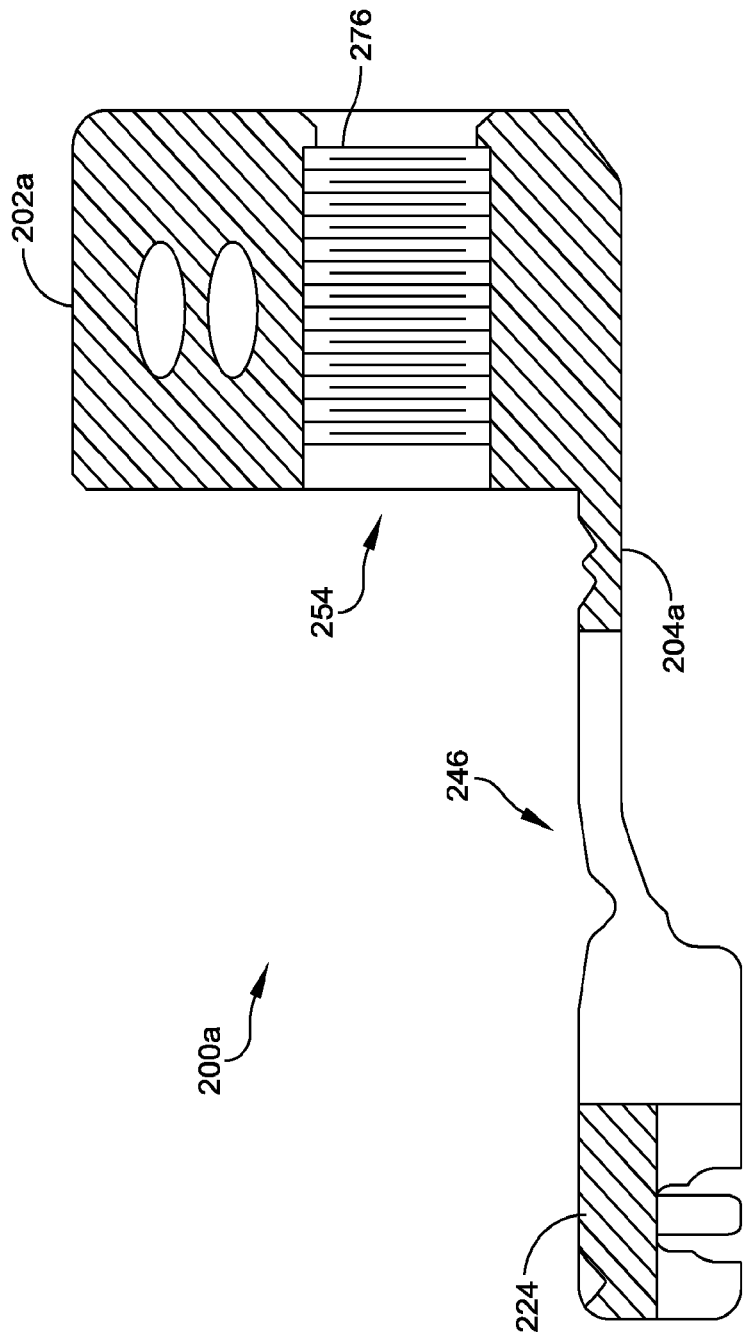
FIG. 20 illustrate a cross-sectional view of the broach guide taken along line E-E in FIG. 14, in accordance with some embodiments.

In some embodiments, the one or more angled pin holes 250a-250b each extend through the body along a hole axis that angled with respect to the longitudinal axis 294 of the body 202a. For example, in the illustrated embodiment, a first angled pin hole 250a extends through the body 202a at an oblique angle $\Theta_2$, as illustrated in FIG. 19. A second angled pin hole 250b can be a mirror image of the first angled pin hole 250a such that the second angled pin hole extends through the body 202a at a similar angle but mirrored with respect to the longitudinal axis 294, although it will be appreciated that the second angle pin hole 250b can extend through the body 202 at any suitable oblique angle greater than 90°.

Figure 5:
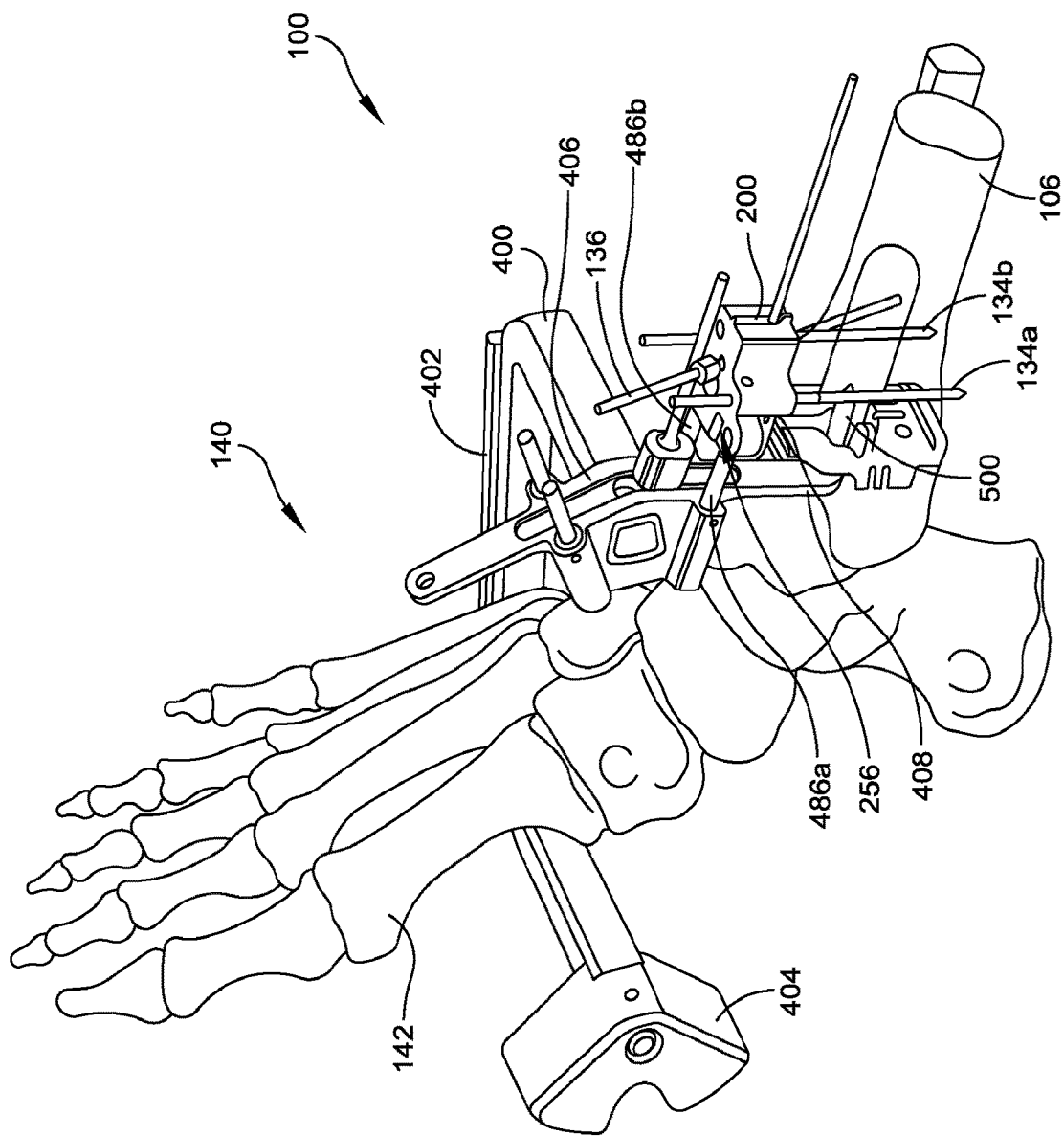
FIG. 5 illustrates the resected ankle joint of FIG. 4 having an offset impactor including a first broach and coupled to the broach guide, in accordance with some embodiments.
Figure 6:
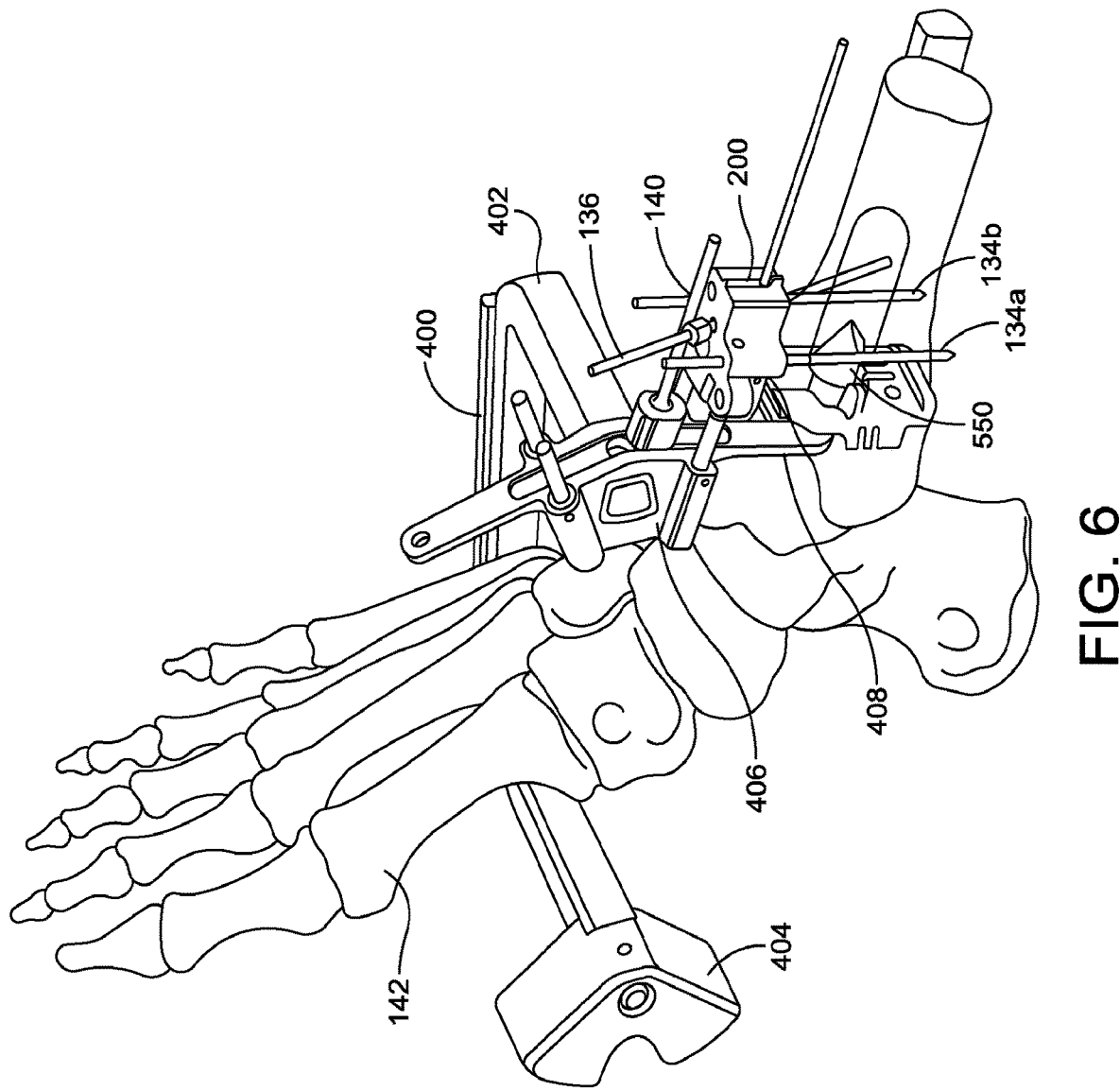
FIG. 6 illustrates the resected ankle joint of FIG. 5 having an offset impactor including a second broach coupled to the broach guide, in accordance with some embodiments.

In some embodiments, the one or more angled pin holes 250a-250b are sized and configured to receive a temporary AP fixation element 136 therethrough (see FIG. 5). The temporary AP fixation element 136 is configured to fix the anterior/posterior position of the broach guide 200a with respect to a tibia 106. For example, in some embodiments, the temporary AP fixation element 136 includes a stop 140 configured to abut an outer surface 216b of the body 202a to prevent anterior/posterior movement of the body 202a. In other embodiments, the stop 140 can be sized and configured to be partially inserted into one of the angled pin holes 250a-250b. In other embodiments, the angled pin holes 250a-250b are each configured to receive a k-wire, therethrough to fix the anterior/posterior position of the broach guide 200a.

In some embodiments, each of the angled pin holes 250a-250b include a first portion 298a having a first diameter and a second portion 298b having a second diameter, as illustrated in FIG. 19. The first diameter is less than the second diameter. In some embodiments, the first diameter allows a fixation portion of a temporary AP fixation element 136 to pass therethrough. The transition between the first portion 298a and the second portion 298b defines a stop surface 299. The stop 140 of the temporary AP fixation element 136 can be inserted into the second portion 298b of the angled pin hole 254a, 254b until the stop 140 contacts the stop surface 299. Contact between the stop surface 299 and the stop 140 prevents anterior/posterior movement of the broach guide 200. In other embodiments, the stop 140 can be configured to abut the outer surface 216b of the broach guide 200a. Although embodiments are illustrated including angled pin holes 250a-250b having a first diameter and a second diameter, it will be appreciated that the angle pin hole 250a-250b can have a constant diameter in a first portion 298a and a second portion 298b.

In some embodiments, the body 202a defines an adjustment hole 254 extending from the outer surface 216b to the bone contact surface 216a. The adjustment hole 254 is sized and configured to receive an AP adjustment screw 206a therein. The AP adjustment screw 206 is inserted into the adjustment hole 254 from the bone facing surface 216a. In some embodiments, the adjustment hole 254 defines an internal thread 276 extending from a first side 216a to a second side 216b, although it will be appreciated that the internal thread 276 can extend over only a portion of the adjustment hole 254, such as a proximal portion, a distal portion, and/or any other portion of the adjustment hole 254. The AP adjustment screw 206a defines a thread 274a sized and configured to engage with the internal threads 276 of the adjustment hole 254.

In some embodiments, the distal end 207a of the adjustment screw 206 extends from the bone facing surface 216a of the body 202a. The distal end 206a includes a bone contacting head 270 coupled to the threaded portion 273 by a shaft 272 (see FIG. 21). The AP adjustment screw 206 can be advanced into/out of the adjustment hole 254 to adjust the anterior/posterior spacing of the body 202s with respect to the bone. For example, in some embodiments, the adjustment screw 206 is positioned at a minimum spacing, the head 270 is positioned within the adjustment hole 254 and the bone contact surface 216a is in contact with an anterior surface of the bone. The adjustment screw 206 can be rotated clockwise from the initial position to increase the spacing between the bone contact surface 216a and the bone. As the adjustment screw 206 is adjusted, the head 270 is placed in contact with the bone and increases the distance between the bone contacting surface 216a and the bone. The adjustment screw 206 can be adjusted until a stop 214 is contacted. This configuration may be referred to as a maximum spacing between the body 202a and the bone. The adjustment screw 206 can be rotated counter-clockwise to reduce the spacing with respect to the bone contact surface 216a. In some embodiments, the adjustment screw 206 can be rotated, for example by a driver 138, to position the body 202a at any spacing between the minimum spacing and the maximum spacing.

FIGS. 21-22 illustrate one embodiment of an adjustment screw 206a, in accordance with some embodiments. In some embodiments, the proximal end 207a of the adjustment screw 206a defines a driver cavity 280 sized and configured to receive a driver, such as the T-wrench 138, therein. The driver cavity 280 can define any suitable shape for receiving a driver therein, such as a hexagonal shape having a sidewall 286 defining a plurality of driver surfaces. The driver cavity 280 is configured to receive a guide tip of a driver 138, and it will be appreciated that the driver cavity 280 can define any suitable shape configured to receive a drive shaft and/or a guide tip of the driver 138 therein.

In some embodiments, the adjustment screw 206a includes a head 270a having a first diameter a non-threaded shaft 272a extending proximally from the head 270a and having a second diameter. The second diameter is less than the first diameter. The adjustment screw 206a can further include a threaded portion 273 defining external threads 274a and having a third diameter. In some embodiments, the third diameter and the first diameter are the same.

With reference again to FIGS. 12-20, in some embodiments, the broach guide 200a is coupled to the tibia 106 with the adjustment screw 206 at a minimum spacing such that the bone contacting head 270 is positioned within the bone facing surface 216a to define a minimum spacing between the bone facing surface 216a and the bone. A surgeon inserts a driver, such as a T-wrench into the driver cavity 280 defined by the adjustment screw 206a. The surgeon can adjust the thread engagement between the thread 274a of the adjustment screw 206a and the internal thread 276 of the adjustment hole 254 to increase or decrease the distance between the head 270a and the bone facing surface 216a. The distance can be adjusted to position a broach opening 246 defined in a guide portion 204a of the guide broach 200a at a desired tibial stem insertion position. In some embodiments, the body 202a defines a pin hole 214 sized and configured to receive a pin therein. The pin prevents the adjustment screw 206 from being fully unthreaded and/or falling out of the adjustment hole 254. In other embodiments, the pin may be replaced with other suitable elements, such as a set screw, configured to prevent the adjustment screw 206 from being removed from the adjustment hole 254. One or more temporary AP fixation elements 136 can be inserted through one or more angled pin holes 250a-250b to maintain the broach guide 200a in the selected anterior/posterior position with respect to the tibia 106, as previously discussed.

In some embodiments, the broach guide 200a includes a guide body 204a extending from the body portion 202a. The guide body 204a is coupled to the body portion 202a by an offset coupling extension 205. The offset coupling extension 205 positions at least a portion of the guide body 204a below a plane defined by the inferior surface 218b of the body 202a. The guide body 204a extends between side walls 219a, 219b extending from a first end 228a coupled to the offset coupling extension 205 to a second end 228b along the longitudinal axis 294. The guide body 204a defines a broach guide hole 246 extending from a bone facing surface 220a to a broach-contacting surface 220b. The broach guide hole 246 is sized and configured to receive a broach, such as first broach 500 and/or second broach 550, therethrough. A center of the broach guide hole 246 is positioned a predetermined distance from the bone facing surface 216a of the body 202a, such that when the body 202a is fixedly coupled to the tibia 106, the broach guide hole 246 is positioned at a desired tibial stem insertion position.

In some embodiments, an alignment extension 224 extends from a broach-contacting surface 220b. The alignment extensions 224 includes at least a first slot 226a and a second slot 226b extending from a first sidewall 219a to a second side wall 219b. The slots 226a, 226b are sized and configured to provide parallax cues for fluoroscopy alignment. In some embodiments, the broach guide 200a can include a plurality of holes 248a-248d extending from a bone facing surface 220a to a broach contacting surface 220b. The holes 248a-248d can be configured to receive one or more additional surgical instruments, such as, for example, a spreader. In some embodiments, the broach guide 200a includes an alignment slot 264 extending from a distal end 228b through the alignment extension 224. The alignment slot is configured to provide visualization of a center of the broach guide 200a and/or a center of a cut to be formed with the broach guide 200a.

In some embodiments, a bone facing surface 220a includes a distal sizing notch 232 and one or more proximal sizing notches 233a, 233b. The distance between the distal sizing notch 232 and each of the proximal sizing notches 233a, 233b corresponds to a length of a tibial tray portion of a tibial implant. For example, in some embodiments, each of the proximal sizing notches 233a, 233b correspond to one of a plurality of tibial tray sizes available to a surgeon. The surgeon can select a tibial tray size based on the position and alignment of the sizing notches 232, 233a, 233b with respect to the resected bone.

In some embodiments, the bone facing surface 220a further defines a tibial stem indicator notch 230. The tibial stem indicator notch 230 identifies a center of the broach guide hole 246, which corresponds to the location of a tibial stem coupled to the tibia, as discussed above with respect to FIGS. 2-11. The tibial stem indicator notch 230 can include a V-shaped opening having an angle $\Theta_1$ between a first side wall 231a and a second side wall 231b. The angle $\Theta_1$ can be any suitable angle to advantageously allow a user to use the notch 230 during anterior/posterior positioning of the broach guide 200.

As discussed above, when the broach guide 200a is properly aligned within the resected tibial portion 108, for example using the adjustment screw 206 as described above in conjunction with the alignment wings 300a, the anterior/posterior position of the broach guide 200a is fixed using one or more temporary AP fixation elements 136. Fixation of the broach guide 200a fixes the position of the broach guide hole 246 in a predetermined position corresponding to the desired placement of the tibial stem 150 in the tibia 106 during the anterior ankle approach method 1000 procedure described above in conjunction with FIGS. 2-11.

Figure 23:
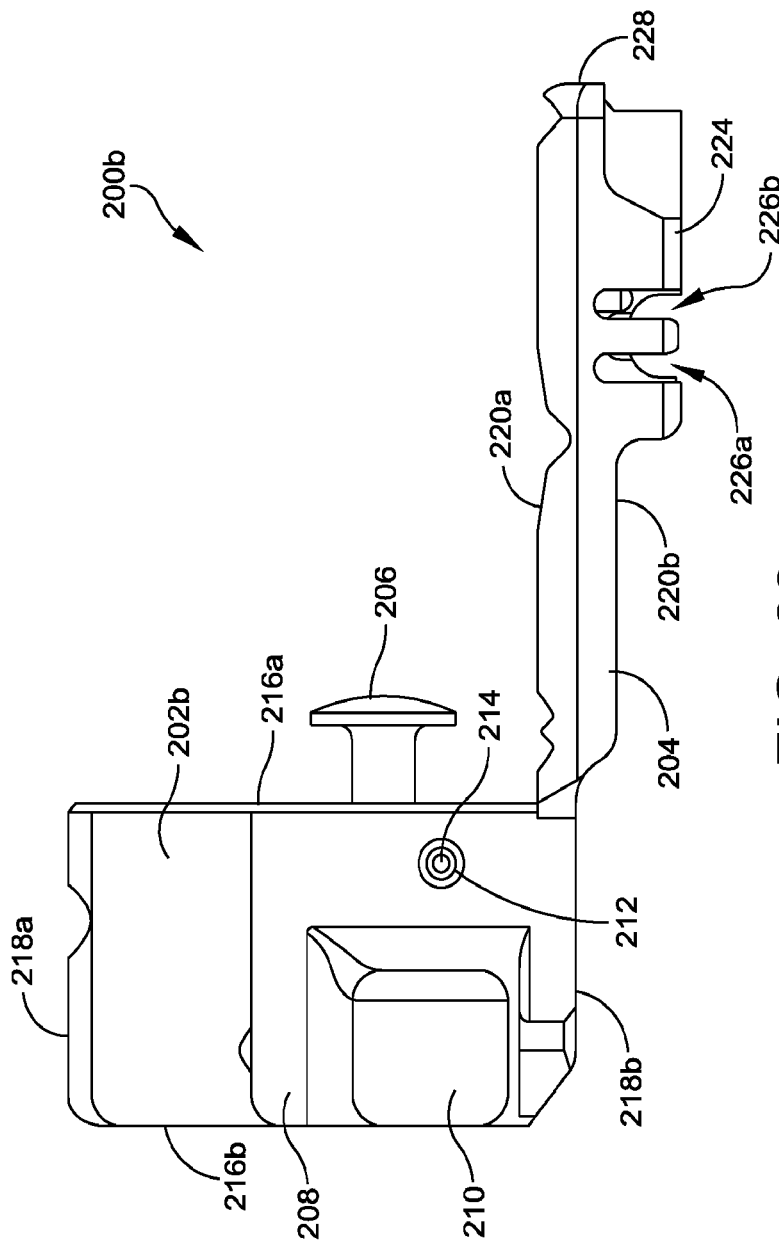
FIG. 23 illustrates a broach guide, in accordance with some embodiments.

FIG. 23 illustrates another embodiment of a broach guide 200b. The broach guide 200b is similar to the broach guides 200, 200a described above, and similar description is not repeated herein. In some embodiments, the broach guide 200b includes a body portion 202b having one or more rounded extensions 208, 210 extending therefrom. The one or more rounded extensions 208, 210 can define one or more holes therethrough. For example, in some embodiments, a first rounded extension 208 defines a parallel pin hole 252a, 252b therethrough and a second rounded extension 210 defines pin hole (not shown) sized and configured to receive an alignment wing 300 therethrough (see FIG. 4).

Figure 24:
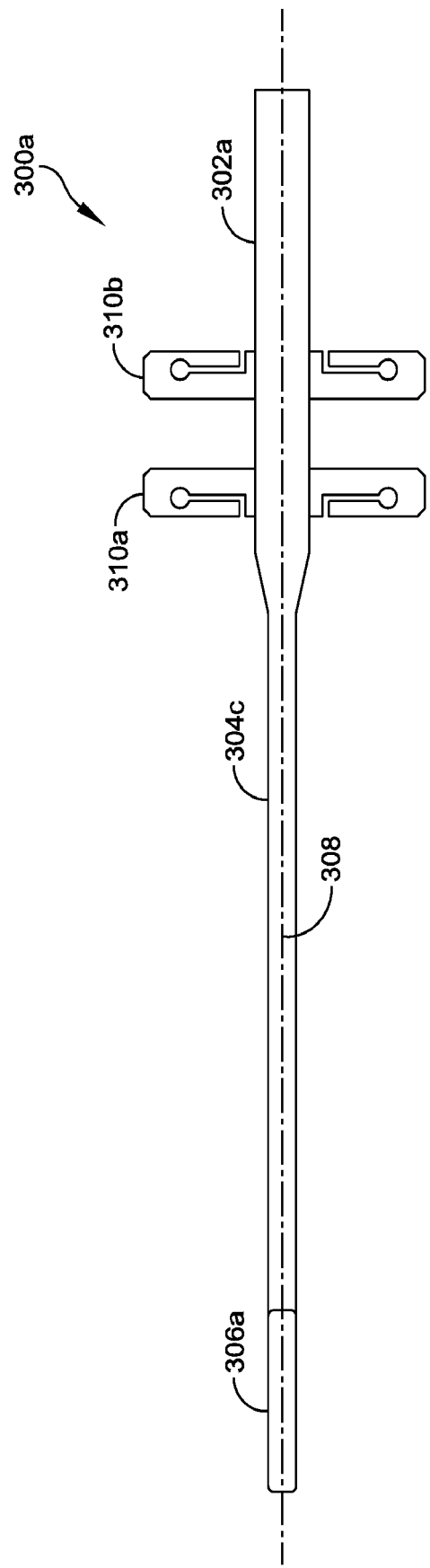
FIG. 24 illustrates a side view of an alignment wing assembly, in accordance with some embodiments.
Figure 25:
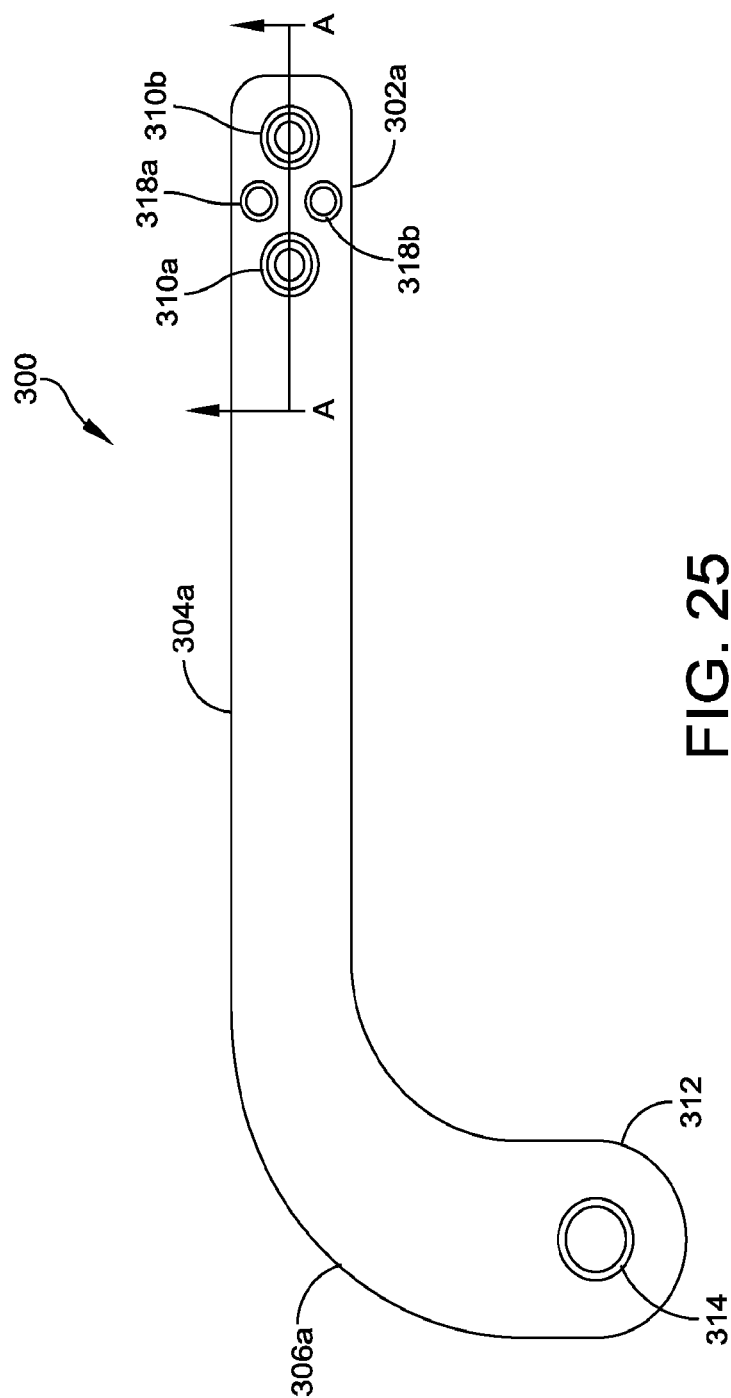
FIG. 25 illustrates a top-down view of the alignment wing assembly of FIG. 24, in accordance with some embodiments.
Figure 26:
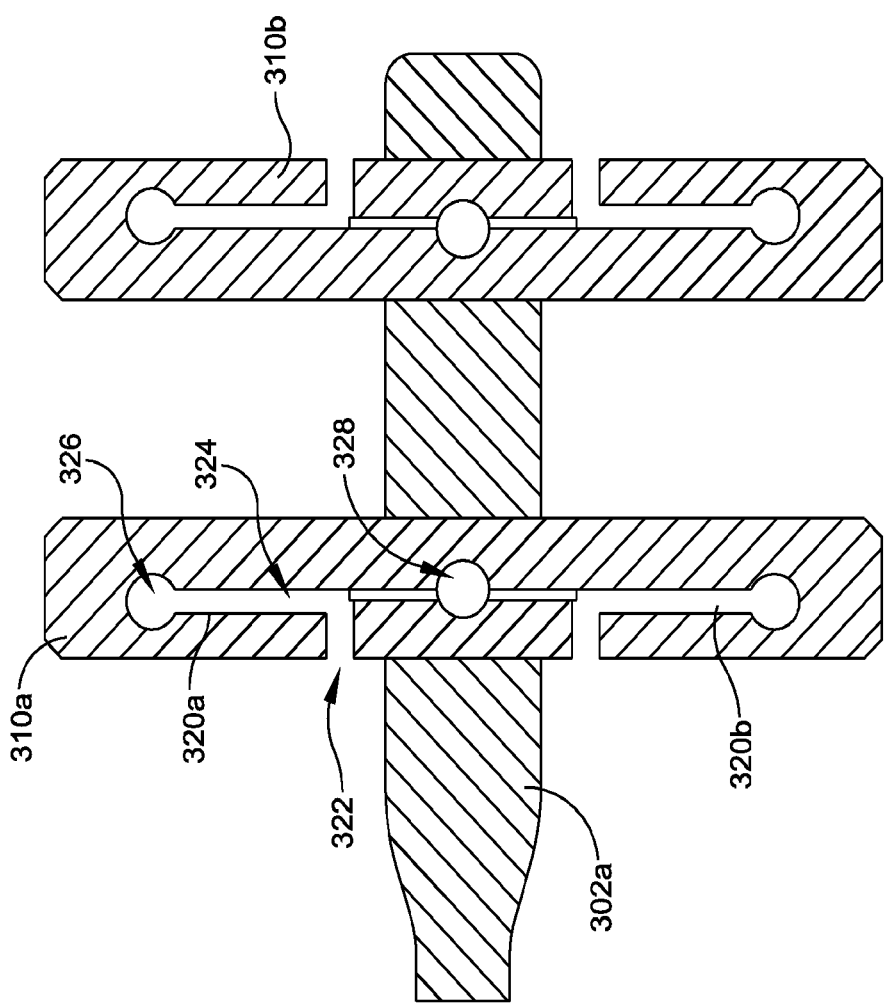
FIG. 26 illustrates a cross-sectional view of the alignment wing assembly taken along line A-A in FIG. 25, in accordance with some embodiments.

FIGS. 24-26 illustrate an alignment wing 300a, in accordance with some embodiments. The alignment wing 300a is similar to the alignment wing 300 described above, and similar description is not repeated herein. The alignment wing 300a includes a body portion 302a having a longitudinal alignment arm 304a extending therefrom. The longitudinal alignment arm 304a extends along a longitudinal axis 308. A pin receiving portion 306a curves from the alignment arm 304a in a continuous curve such that an end of the pin receiving portion 306a is disposed at about 90° with respect to the longitudinal alignment arm 304a, although it will be appreciated that a greater and/or lesser curve can be used. The pin receiving portion 306a includes a hole 314 sized and configured to receive an alignment rod 350 (see FIG. 27) therethrough. The alignment rod 350 extends through the pin receiving portion 306a and indicates the anterior/posterior position of the broach guide 200 with respect to the tibia 106.

In some embodiments, the body portion 302a includes a first coupling extension 310a and a second coupling extensions 310b extending therefrom. The coupling extensions 310a, 310b are sized and configured to couple the alignment wing 300a to a broach guide, such as the broach guide 200. Each of the coupling extensions 310a, 310b include a superior slot 320a and an inferior slot 320b. The slots 320a, 320b each define an opening 322, a vertical extension 324, and an opening 326. The coupling extensions 310a, 310b are configured to provide a force or tension fit between the alignment wing 300a and the broach guide 200. In the illustrated embodiment, the coupling extensions 310a, 310b provide a leaf-spring type connection, although it will be appreciated that the coupling extension 310a, 310b can be configured to provide any suitable force and/or tension fit. In some embodiments, the coupling extensions 310a, 310b are configured to provide coupling of the alignment wing 300a in a selected one of a right-side configuration or a left-side configuration, corresponding to the side of the bone about which the alignment wing 300a curves.

Figure 27:
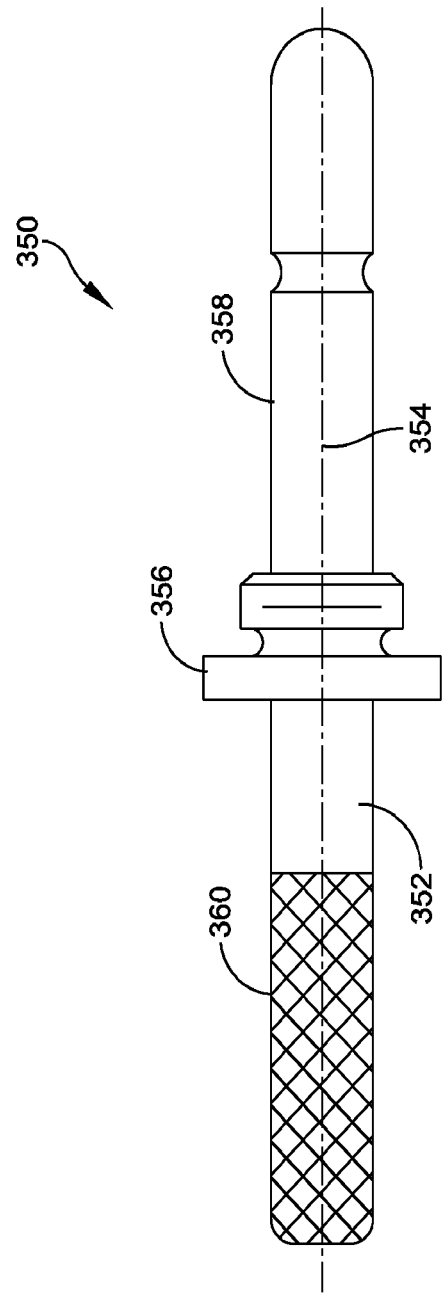
FIG. 27 illustrates an alignment rod configured to be coupled to the alignment wing assembly of FIG. 24, in accordance with some embodiments

FIG. 27 illustrates an alignment rod 350 sized and configured for insertion through the hole 314 of the pin receiving portion 306a of the alignment wing 300a. The alignment rod 350 includes a body 352 extending along a longitudinal axis 354. A stop 356 is positioned between a handle 360 and an insertion portion 358. The alignment rod 350 is coupled to the alignment wing 300a by inserting the insertion portion 358 through the pin receiving hole 314 until the stop 356 abuts the surface of the pin receiving portion 306a. In some embodiments, the alignment rod 350 is threaded into the pin receiving hole 314, although it will be appreciated that a non-threaded connection be used. The stop 356 maintains the alignment rod 350 in a perpendicular alignment with respect to the pin receiving portion 306a. In some embodiments, the alignment rod 350 includes one or more grooves corresponding to one or more sizes of stems configured for insertion into the first bone. The one or more grooves can be used to select and/or confirm stem sizing prior to implantation of a stem. After aligning the broach guide 200, the alignment rod 350 can be removed from the pin receiving hole 314. In other embodiments, the alignment wing 300a (including an attached alignment rod 350) can be removed as a single piece from the broach guide 200.

Figure 28:
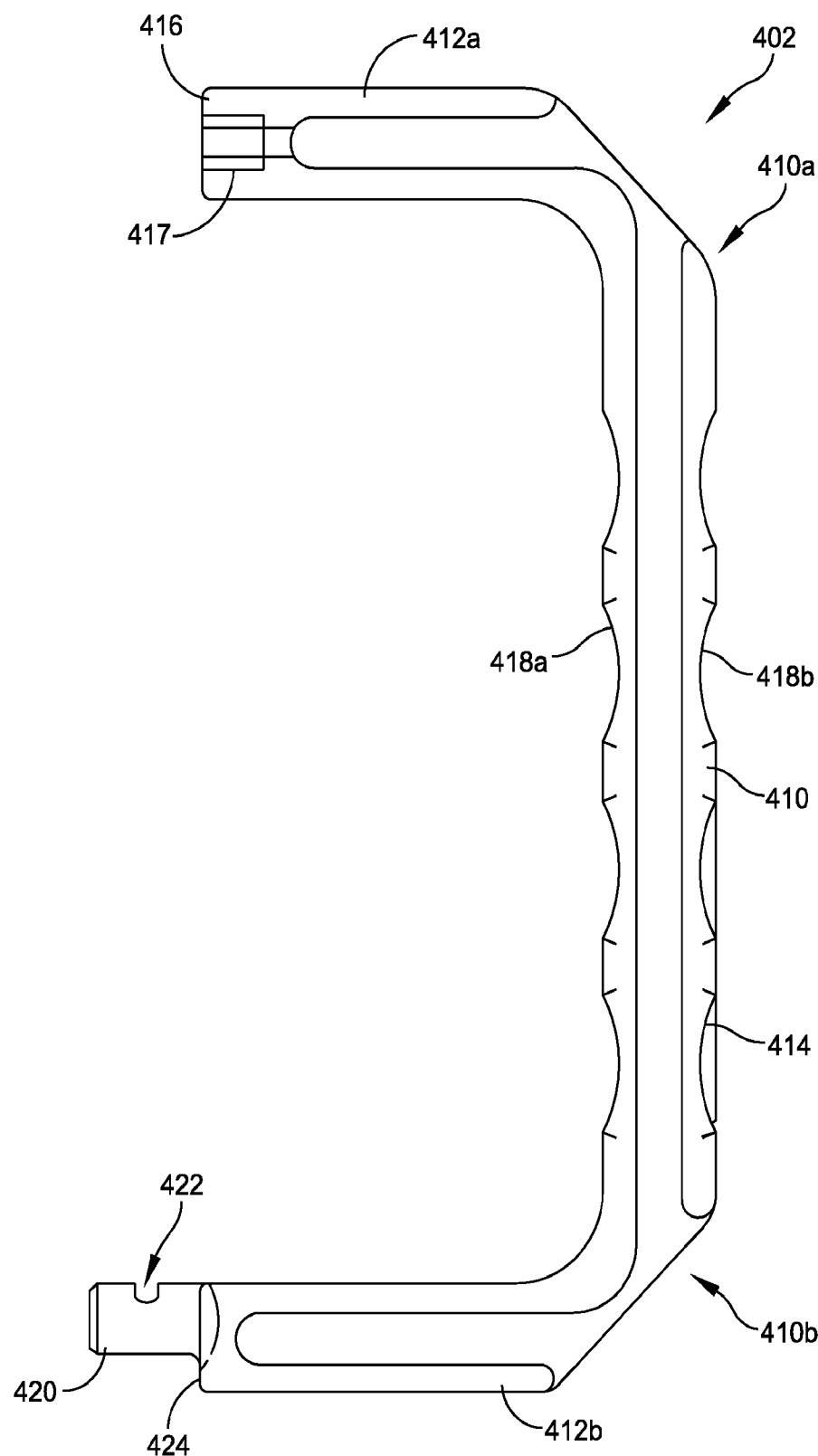
FIG. 28 illustrates a side view of an offset shaft of an offset impactor assembly, in accordance with some embodiments.
Figure 28A:
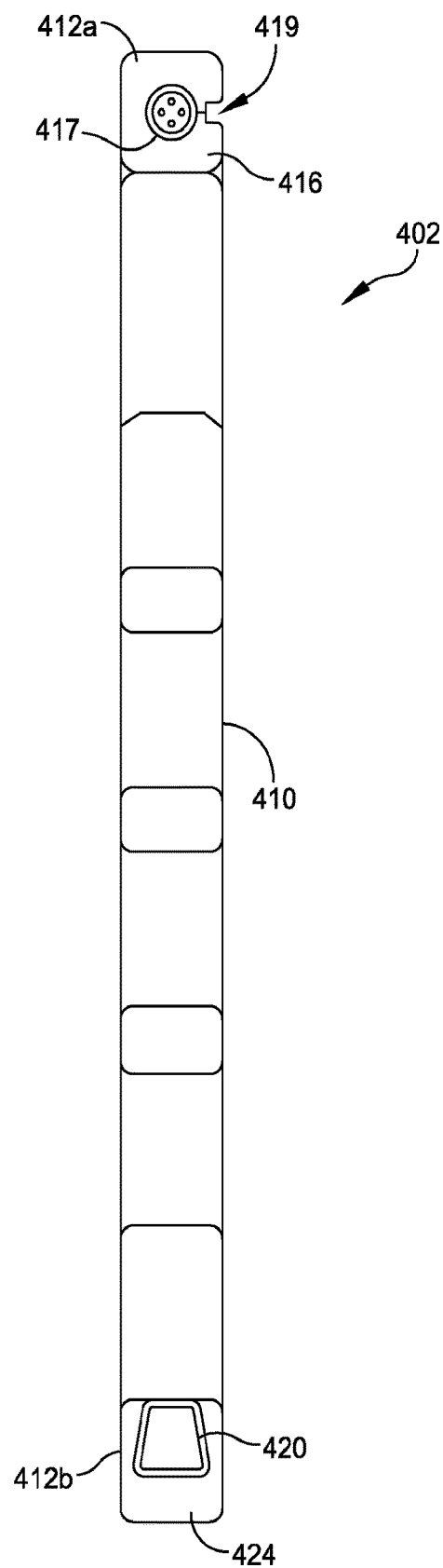
FIG. 28A illustrates a front view of the offset impactor assembly of FIG. 28, in accordance with some embodiments.

FIGS. 28-41 illustrate various elements of an offset impactor assembly 400, in accordance with various embodiments. For example, FIG. 28 illustrates one embodiment of an offset shaft 402a. The offset shaft 402a includes a longitudinal section 410 extending substantially along a longitudinal axis between a first end 410a and a second end 410b. An impactor head extension 412a extends from the first end 410a of the longitudinal section 410 and an impactor body section 412b extends from the second end 410b. In the illustrated embodiments, the impactor head extension 412a and the impactor body section 412b extend perpendicular to the longitudinal section 410, although it will be appreciated that the impactor head extension 412a and/or the impactor body extension 412b can extend at a non-perpendicular angle with respect to the longitudinal section 410. In some embodiments, the longitudinal section 410 includes a plurality gripping features 418a, 418b, such as scallops and/or other cutouts formed along the length of the longitudinal section 410.

The impactor head extension 412a is configured to couple the offset shaft 402a to an impactor head, such as impactor head 404. The impactor head extension 412a can be coupled to the impactor head 404 using any suitable coupling means. For example, in some embodiments, the impactor head extension 412a includes coupling portion 416 having a predetermined geometry with a cutout 419 and defining a threaded opening 417 extending from a distal surface into the coupling portion 416. The coupling portion 416 is configured to be inserted into a shaft opening defined in an impactor head, such as impactor heads 404a, 404b described in more detailed below. A threaded pin (not shown) is inserted through the impactor head 404a, 404b and coupled to the threaded opening 417 to fixedly couple the impactor head 404a, 404b to the coupling portion 416. In other embodiments, the impactor head extension 412a can be coupled to an impactor head 404 using a threaded head extending from the impactor head extension 412a, a force-fit coupling, a set screw, and/or any other suitable coupling element. The extension 412a positions the impactor head 404 for impaction during an anterior approach method 1000.

The impactor body extension 412b is configured to couple the offset shaft 402a to an impactor body, such as impactor body 406. The impactor body extension 412b can be coupled to the impactor body 406 using any suitable coupling means.

For example, in the illustrated embodiments, the impactor body extension 412b includes a trapezoidal coupling element 420 sized and configured to be inserted into an impactor body 406, as discussed in greater detail below with respect to FIGS. 32-33. The trapezoidal coupling element 420 includes a slot 422 configured to receive a locking element, such as a retention protrusion 485 formed on a shaft retainer 464, as discussed in greater detail below. In other embodiments, the coupling element 420 can include any suitable coupling element, such as a threaded coupling element, a press-fit coupling, a set screw coupling, and/or any other suitable coupling element. In some embodiments, the impactor body extension 412b defines a stop surface 424 configured to prevent over insertion of the impactor body extension 412b into an impactor body 406.

Figure 29:
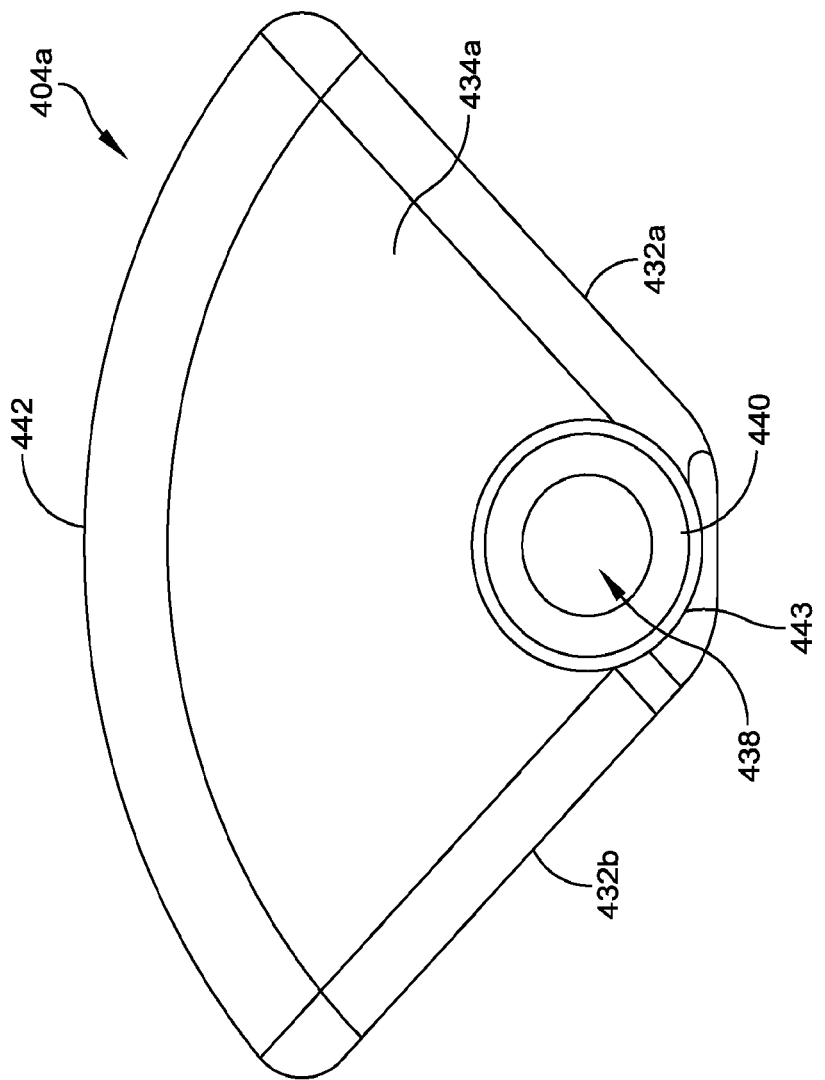
FIG. 29 illustrates a top view of a solid impactor head, in accordance with some embodiments.
Figure 30:
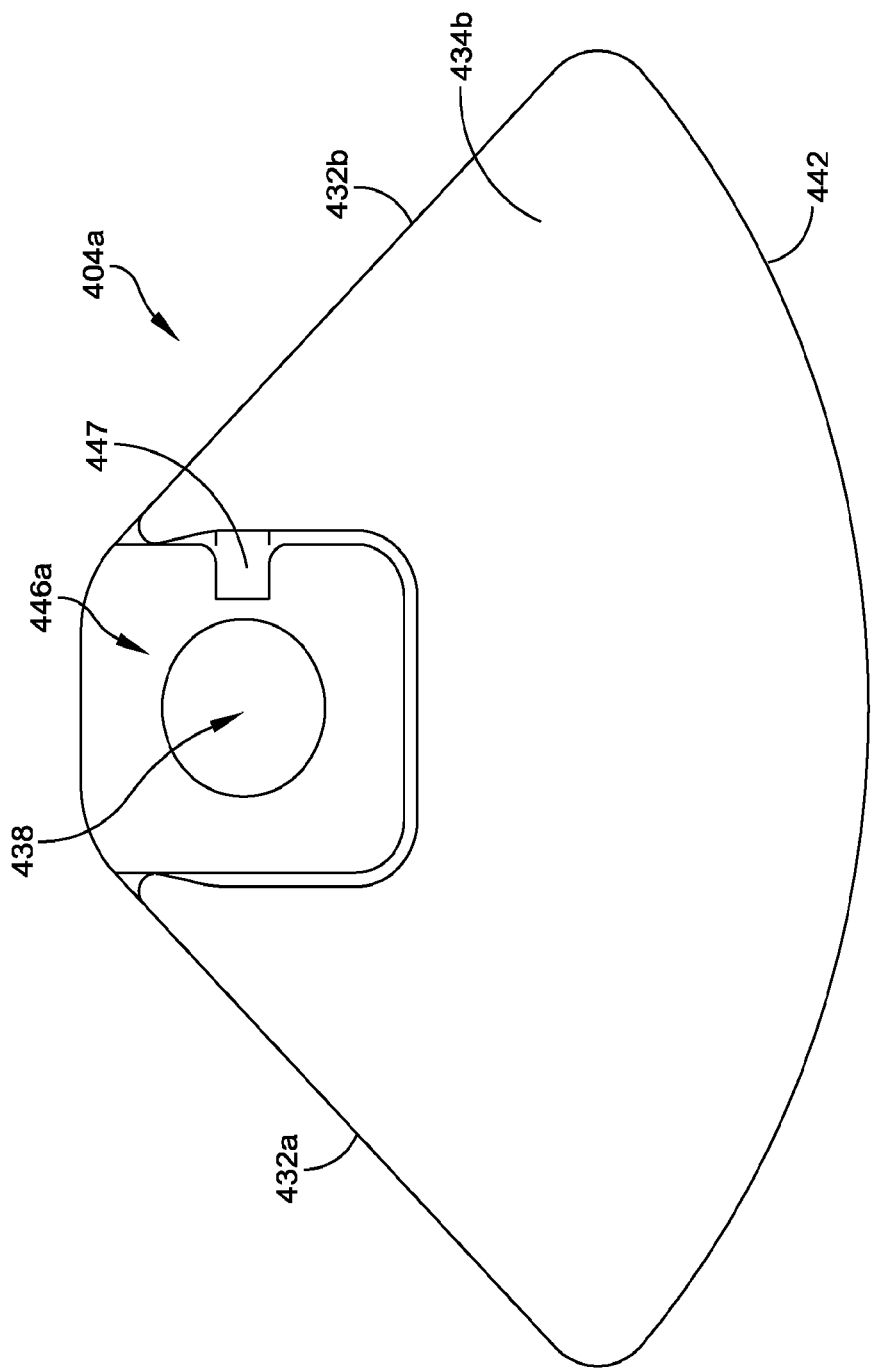
FIG. 30 illustrates a bottom view of the solid impactor head of FIG. 29, in accordance with some embodiments.

FIGS. 29-30 illustrate a solid impactor head 404a, in accordance with some embodiments. The solid impactor head 404a is similar to the impactor head 404 discussed above with respect to FIGS. 2-11, and similar description is not repeated herein. The solid impactor head 404a extends between a first surface 434a and a second surface 434b. The solid impactor head 404a includes an impaction surface 442 extending between distal ends of a first side surface 432a and a second side surface 432b. In some embodiments, a flat surface 443 extends between proximal ends of the first side surface 432a and the second side surface 432b. The impaction surface 442 defines a planar surface configured to receive an impaction force from an impactor. The impactor surface 442 can include a smooth surface and/or a textured surface configured to receive an impaction force.

In some embodiments, a coupling channel 438 extends through the solid impactor head 404a from a first surface 434a to a second surface 434b. The coupling channel 438 is defined by a square opening 446a and a pin opening 446b coupled by a pin shaft channel 444 extending therebetween. The square opening 446a is sized and configured to receive a coupling portion 416 of the offset shaft 402a therein. The pin shaft channel 444 is sized and configured to receive the shaft of a threaded pin therethrough and the pin opening 446b is sized and configured to receive a head of the threaded pin therein.

In use, the solid impactor head 404a is coupled to the impactor head extension 412a of the offset shaft 402a. The coupling portion 416 of the offset shaft 402a is inserted into the shaft opening 446a. In some embodiments, the coupling portion 416 and the shaft opening 446a have a complimentary geometry configured to indicate proper alignment of the offset shaft 402a and the impactor head 404a. For example, in some embodiments, the coupling portion 416 defines a generally square perimeter having a cutout 419 formed in a sidewall of the coupling portion 416 and the shaft opening 446a defines a generally square perimeter having a protrusion 447 extending from one of the sidewalls of the shaft opening 446a into the shaft opening 446a. The protrusion 447 is sized and configured to be received within the cutout 419 in the coupling portion 416 such that the offset shaft 402a and the impactor head 404a can only be coupled in a predetermined alignment.

A threaded pin is inserted through the pin opening 446b and engaged with the threaded opening 417 formed in the coupling portion 416. The threaded pin can include a shaft sized and configured to extend through the pin shaft channel 444 and a head sized and configured to be retained within the pin opening 446b. The threaded pin fixedly maintains engagement between the impactor head 404a and the offset shaft 402a.

Figure 31:
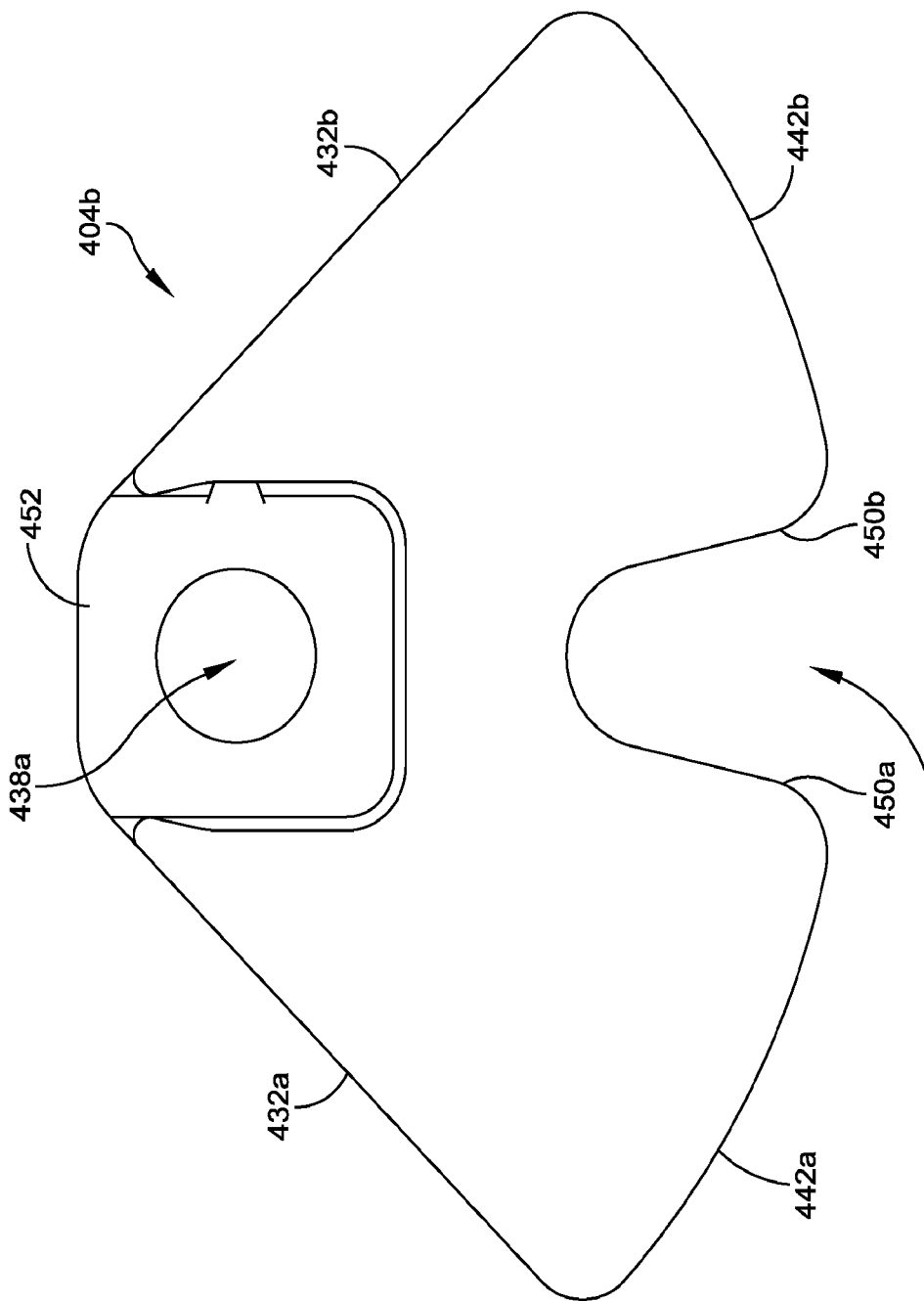
FIG. 31 illustrates a bottom view of a split impactor head of an offset impactor assembly, in accordance with some embodiments.

FIG. 31 illustrates a split impactor head 404b, in accordance with some embodiments. The split impactor head 404b is similar to the solid impactor head 404a described above, and similar description is not repeated herein. The split impactor head 404b includes a slot 448 defining a first rounded surface 442a and a second rounded surface 442b. In some embodiments, the slot 448 is a U-shaped slot including a first sidewall 450a and a second side wall 450b. In some embodiments, the U-shaped slot 448 provides a visual indication for applying an impaction force to the head 404b.

Figure 32:
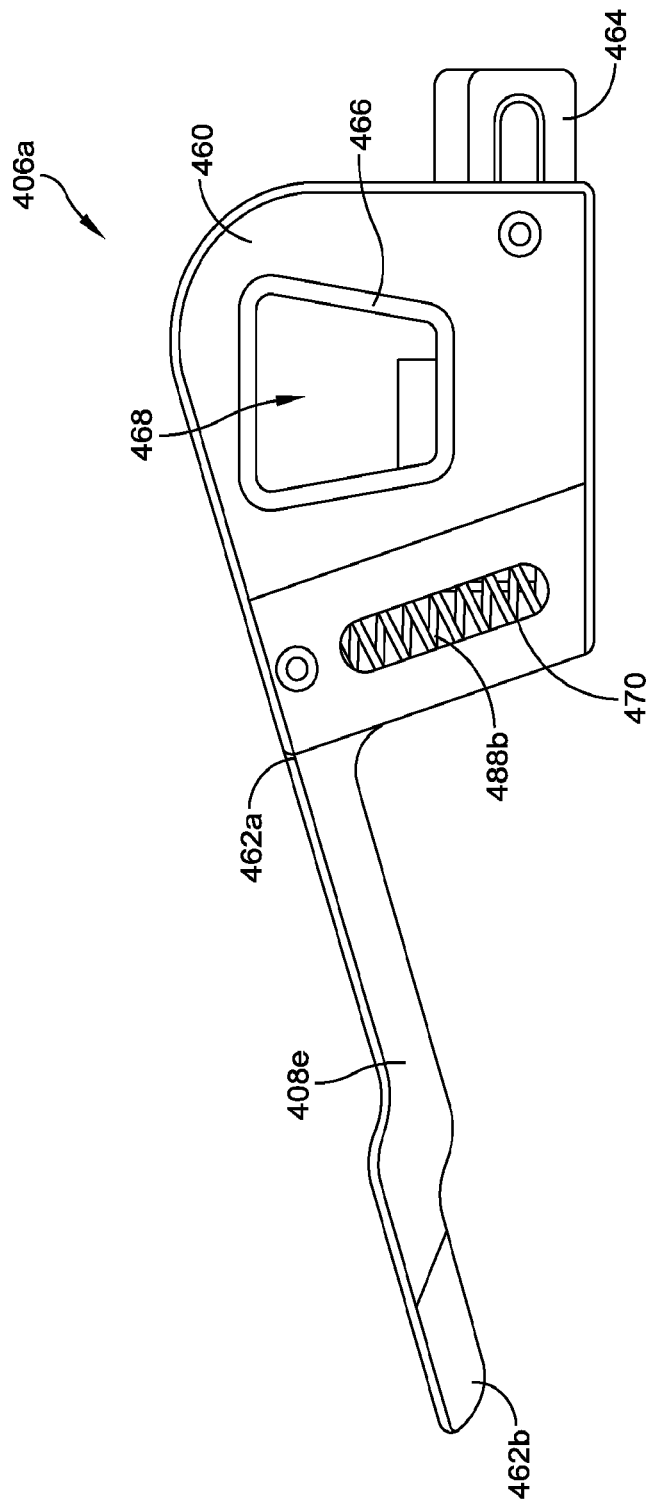
FIG. 32 illustrates a side view of an impactor body of an offset impactor assembly, in accordance with some embodiments.
Figure 33:
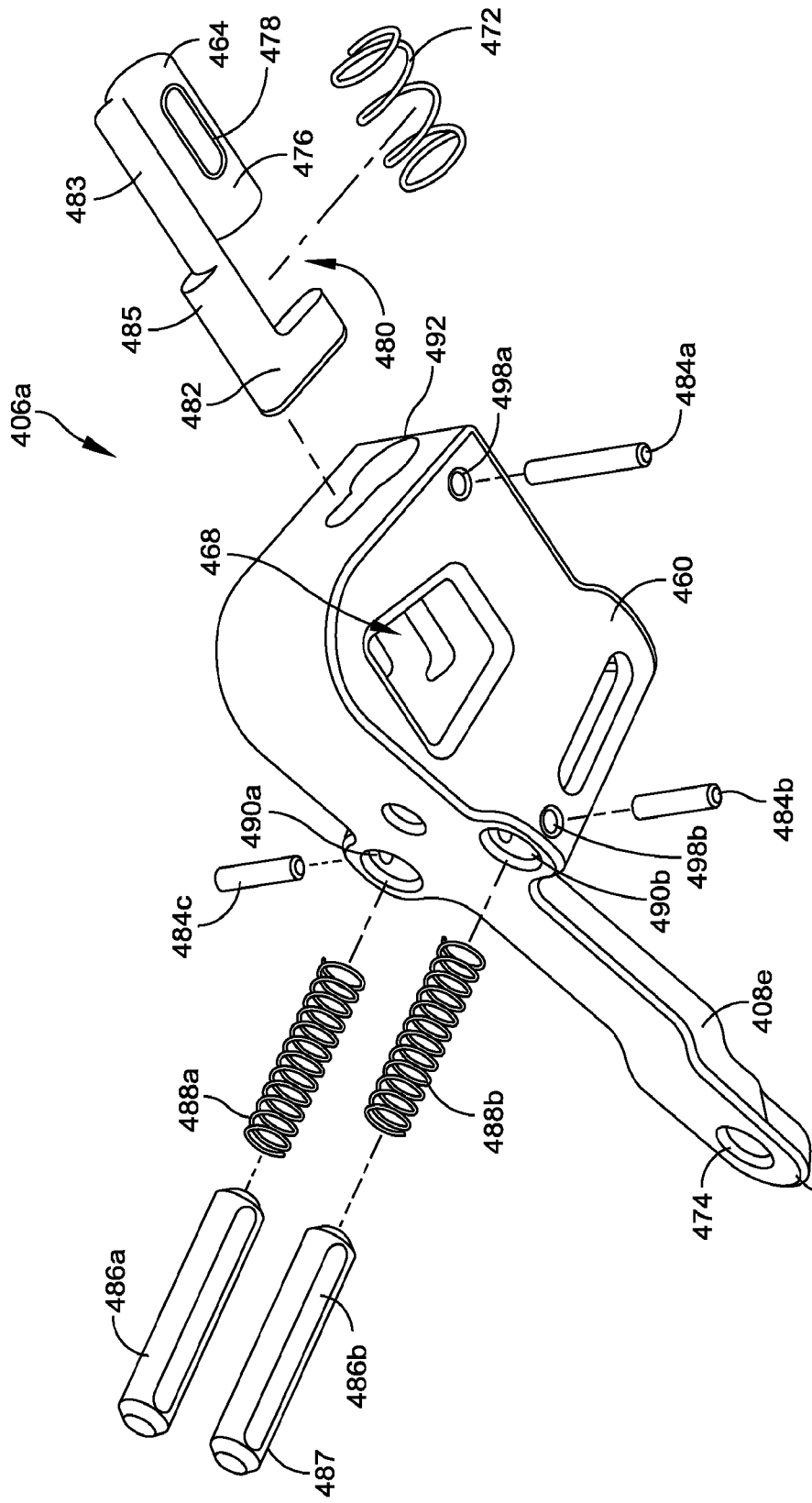
FIG. 33 illustrates an exploded view of the impactor body of FIG. 32, in accordance with some embodiments.
Figure 34:
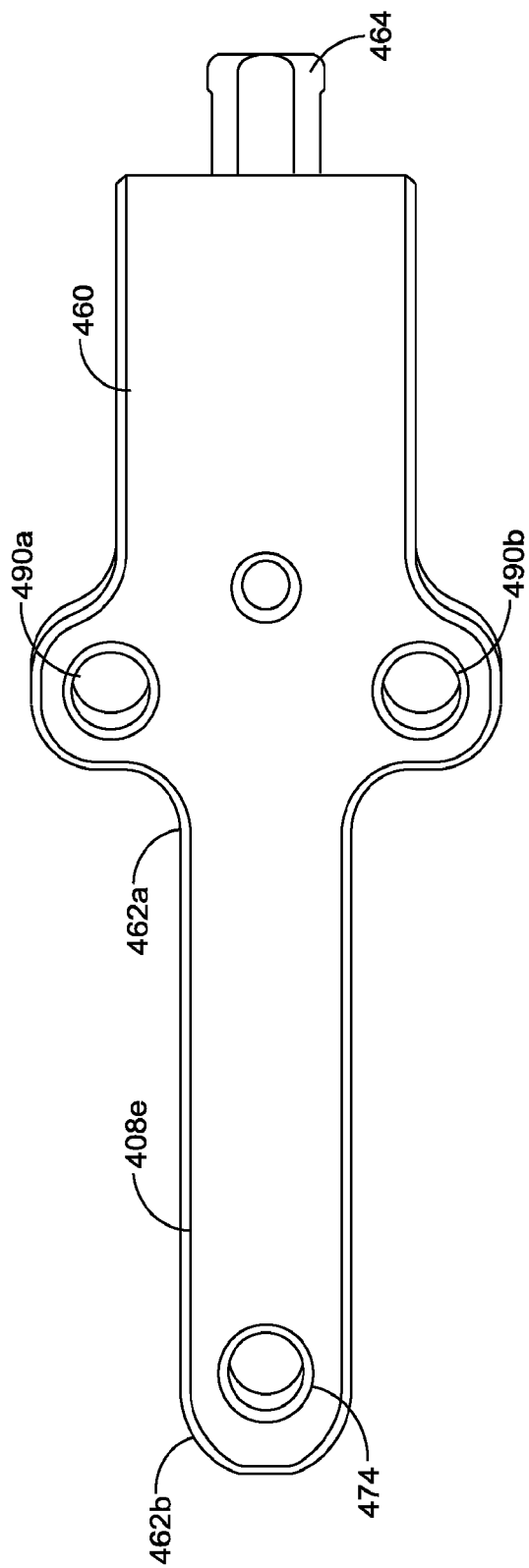
FIG. 34 illustrates a bottom view of the impactor body of FIG. 32, in accordance with some embodiments.
Figure 35:
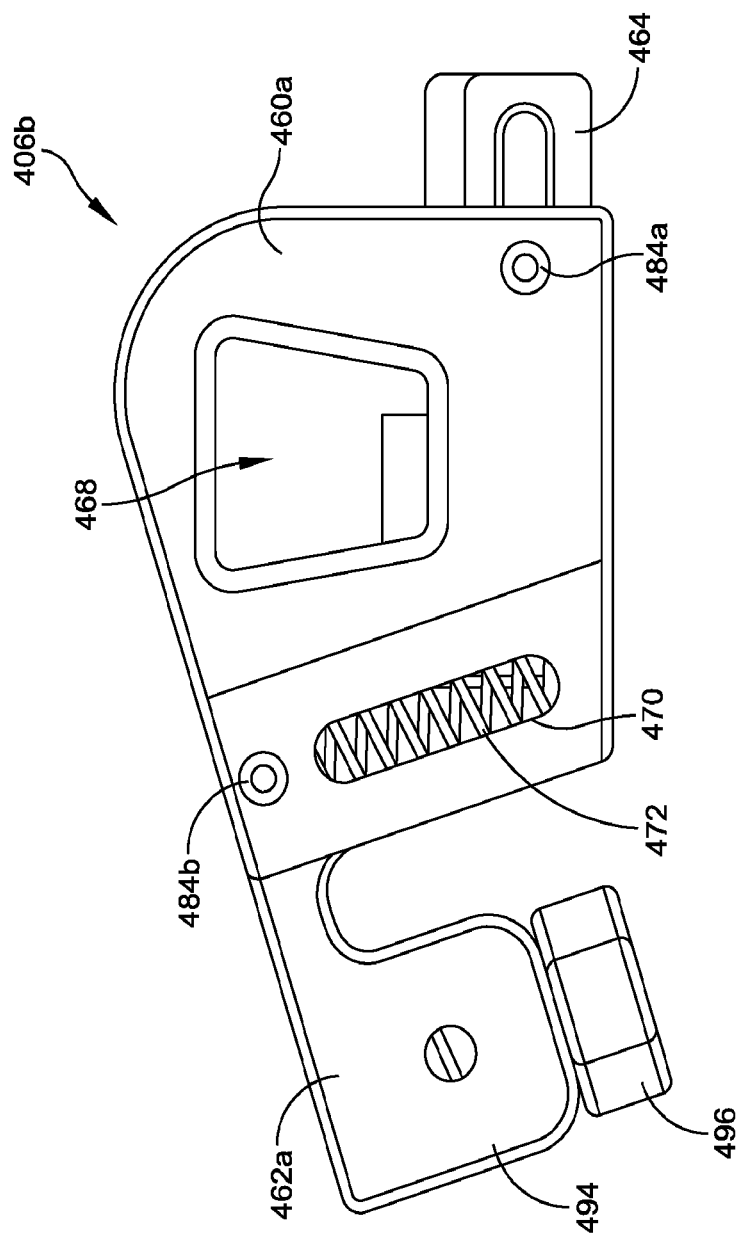
FIG. 35 illustrates a side view of an impactor body of an offset impactor assembly, in accordance with some embodiments.
Figure 36:
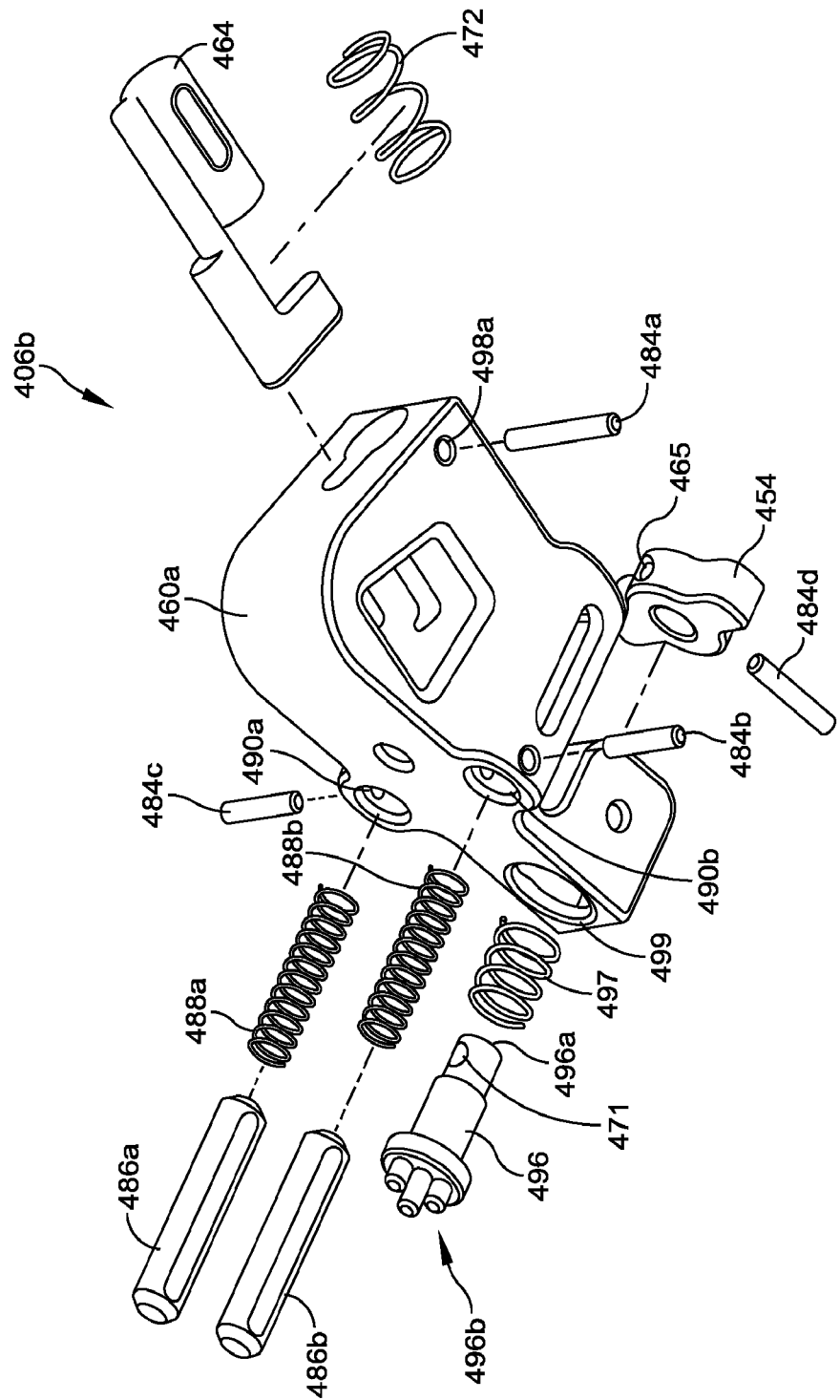
FIG. 36 illustrates an exploded view of the impactor body of FIG. 35, in accordance with some embodiments.
Figure 37:
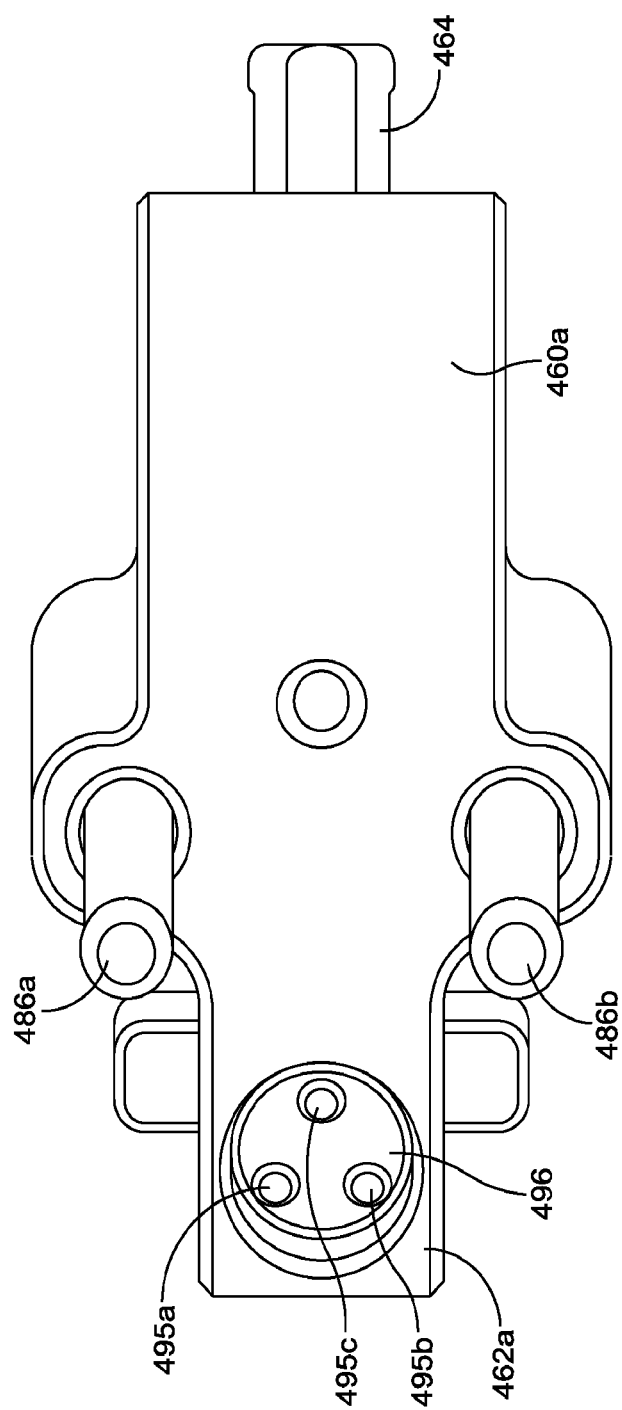
FIG. 37 illustrates a bottom view of the impactor body of FIG. 35, in accordance with some embodiments.
Figure 38:
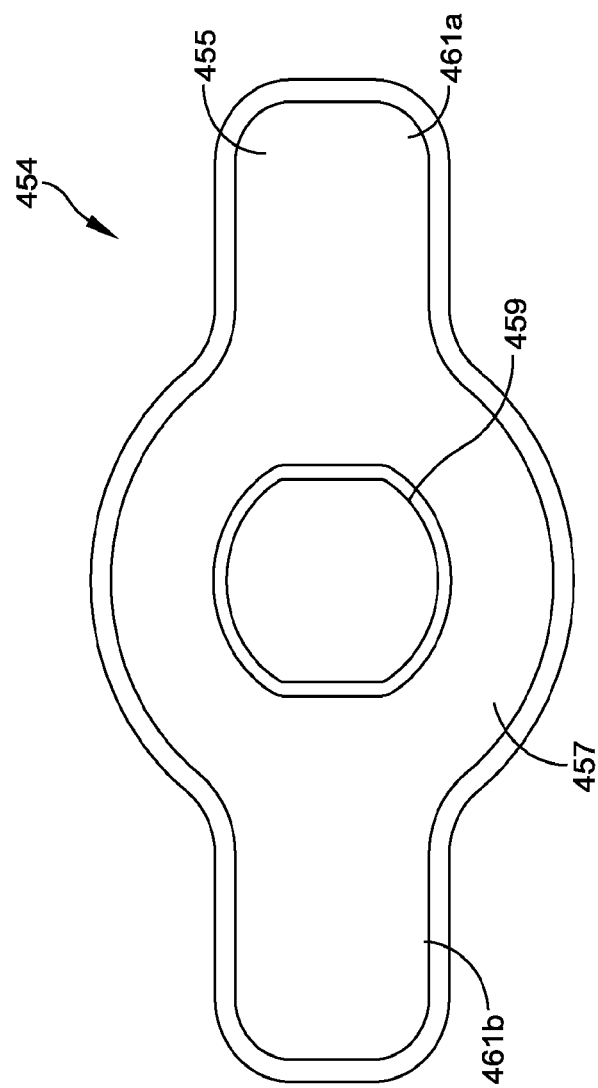
FIG. 38 illustrates front view of an impactor pull of the impactor body of FIG. 35, in accordance with some embodiments.
Figure 39:
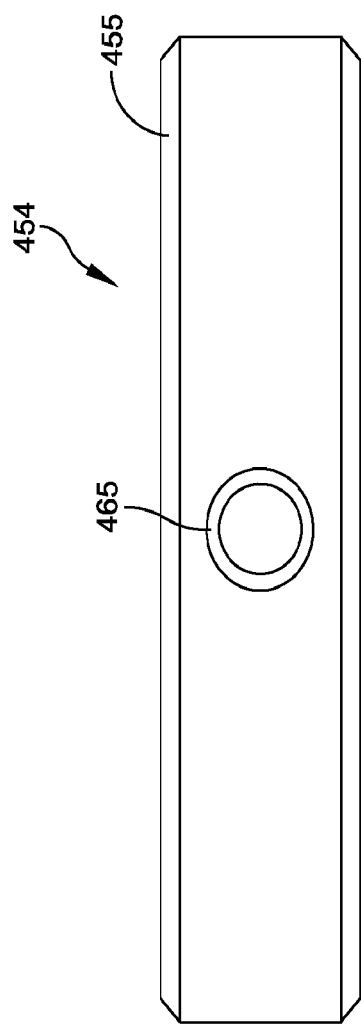
FIG. 39 illustrates a side view of the impactor pull of FIG. 38, in accordance with some embodiments.
Figure 41:
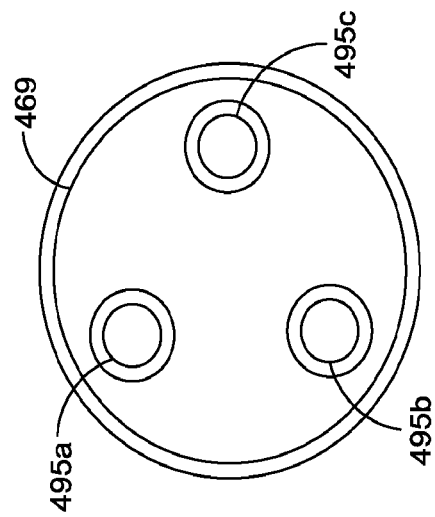
FIG. 41 illustrates a front view of the broach lock of FIG. 40, in accordance with some embodiments.
Figure 40:
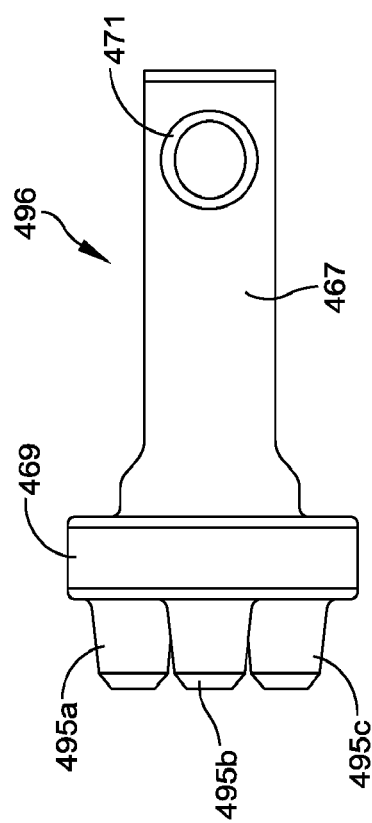
FIG. 40 illustrates a side view of a broach lock of the impactor body of FIG. 35, in accordance with some embodiments.

FIGS. 32-34 illustrate an impactor body 406a, in accordance with some embodiments. The impactor body 406a is similar to the impactor body 406 discussed above, and similar description is not repeated herein. The impactor body 406a includes a housing 460 defining a trapezoidal opening 468 sized and configured to receive a coupling element 420 of an offset shaft 402a therein. For example, in some embodiments, the coupling element 420 is a trapezoidal coupling element and the shaft opening 468 is a trapezoidal opening, although it will be appreciated that one or more alternative complimentary geometries can be used.

In some embodiments, the housing 460 defines a retainer hole 492 sized and configured to receive a shaft retainer 464 therein. The shaft retainer 464 includes a head 476 coupled to a body 482 by an elongate portion 483. A retention protrusion 485 extends from the body 482 and/or the elongate portion 483. The retention protrusion 485 is sized and configured to be received within slot 422 on the coupling element 420 of the offset shaft 402a. A spring 472 is positioned within a space 480 defined between the head 476 and the body 482. When the shaft retainer 464 is inserted into the housing 460, the spring 472 applies a biasing force to bias the shaft retainer 464 in a first direction. The shaft retainer 464 is inserted into the retainer hole 492 and fixed to the housing by a first pin 484a inserted through a first pin hole 498a and into a pin slot 478 defined by the translating head 476.

In some embodiments, the shaft retainer 464 is configured to fixedly couple the offset shaft 402a to the impactor body 406a. During use, the coupling element 420 of the offset shaft 402a is inserted through the shaft opening 468 of the impactor body 406a. The retention protrusion 485 is positioned within the slot 422 defined by the coupling element 420 and prevents the offset shaft 402a from being disconnected from the impactor body 406a. After use, a force is applied to the shaft retainer 464 in a second direction to overcome the spring bias of spring 472 to disengage the retention protrusion 485 from the slot 422. The offset shaft 402a is disconnected from the impactor body 406a while applying the force to the shaft retainer 464.

In some embodiments, the impactor body 406a includes an impaction arm 408e extending from the housing 460. The impaction arm 408e extends generally along a longitudinal axis from a first edge 462a coupled to the housing 460 to a second end 462b. A broach coupling hole 474 is disposed adjacent to the second end 462b and extends through the impaction arm 408e. In some embodiments, the broach coupling hole 474 is configured to couple the impaction arm 408e directly to one or more broaches, such as a first broach 500 and/or a second broach 550. In other embodiments, a slot is configured to couple the impaction arm 462a to a broach impaction arm 408f (see FIGS. 48-50) coupled to a broach 500, 550.

The impactor body 406a is configured to transfer an impaction force applied to an impactor head 404a, 404b coupled to the offset shaft 402a to a broach 500, 550 coupled to the impaction arm 408e. For example, in some embodiments, application of an impaction force to the impactor head 404a, 404b causes translational movement of the offset shaft 402a. The translation movement of the offset shaft 402a causes movement of the impaction arm 408e, which drives a broach coupled to the impaction arm 408e into contact with the distal end of the tibia 106. The broach 500, 550 is driven into contact with the superior surface of the resected tibial portion 108 through the broach guide hole 246 defined in the broach guide 200. The impactor head 404a, 404b can be struck one or more times to drive the broach 500, 550 into the tibia 106 to a predetermined depth to form a stem hole 160 for receiving a tibial stem 150 therein.

In some embodiments, the housing 460 defines one or more holes 490a, 490b sized and configured to receive a spring-loaded shaft 486a, 486b and/or a spring 488a, 488b therein. The holes 490a, 490b can be positioned adjacent to the impaction arm 408e, although it will be appreciated that the housing 460 can define any number of holes 490a, 490b extending through any suitable portion of the housing 460. In some embodiments, the springs 488a, 488b are inserted into the holes 490a, 490b. Subsequently, the shafts 486a, 468b are inserted into the holes 490a, 490b and can partially compress the springs 488a, 488b. The shafts 486a, 486b are retained within the holes 490a, 490b by respective pins 484b, 484c inserted through respective pin holes 498b, 498c and shaft slots 4XX, 4XX. Although embodiments are illustrated herein using retaining pins 498b-498c, it will be appreciated that any suitable retention system, such as pins, screws, detents, and/or any other suitable retention system can be used.

The shafts 486a, 486b are biased to a first position having a portion of the shaft 486a, 486b extending out of the holes 490a, 490b. During use, the shafts 486a, 486b are positioned in contact with one or more surfaces, such as being positioned within slots 256a, 256b defined by the broach guide 200a. When an impaction force is applied to the offset shaft 402, the shafts 486a, 486b are driven into a second position within the holes 490a, 490b and compress the springs 488a, 488b. After application of the impaction force, the springs 488a, 488b apply biasing force to the shafts 486a, 486b to return the shafts 486a, 486b to the first position, which causes the offset shaft 402a to translate in an opposite direction and return the impactor head 404a, 404b to an initial position. In some embodiments, the springs 488a, 488b are configured reduce the amount force applied by the impactor body 406a to one or more system components, such as, for example, the broach guide 200. For example, in some embodiments, the shafts 486a, 486b and the springs 488a, 488b can act as dampeners to reduce a force transferred from the impactor body 406a to a broach guide 200.

FIGS. 35-41 illustrate an embodiment of an impactor body 406b configured to be coupled to a broach impaction arm 408f. The impactor body 406b is similar to the impactor body 406a described above, and similar description is not repeated herein. The impactor body 406b includes an impactor lock 496 coupled to an impactor lock housing 462a. The impactor lock housing 462a is coupled to an impactor head housing 460a. The impactor lock 496 is inserted through a lock hole 499 extending through the lock housing 462a. In some embodiments, a spring 497 is coupled to the impactor lock 496. A first end 496a of the impactor lock 496 is coupled to an impactor pull 454, for example, by inserting the shaft 467 of the impactor lock 496 at least partially through a lock hole 459 defined extending through a pull body 455 between a first surface 457 and a second surface. A pin 484d is inserted through pin holes 471, 465 formed in the first end 496a of the impactor lock 496 and the impactor pull 454, respectively, to couple the impactor lock 496 to the impactor pull 454.

A second end 496b of the impactor lock 496 includes a plurality of arm coupling elements 495a-495c extending from a face 469 of the impactor lock 496. The arm coupling elements 495a-495c are configured to couple the impactor lock 496 to a broach impaction arm, such as the broach impaction arm 408f illustrated in FIGS. 48-50. The arm coupling elements 495a-495c are configured to provide a force-fit coupling to the broach impaction arm 408f, for example, through one or more holes formed in the broach impaction arm 408f. To disconnect the broach impaction arm 408f from the impactor lock 496, a force is applied to the impactor pull 454 to retract the face 469 and the arm coupling elements 495a-495c into the lock housing 462a, forcing the coupling elements 495a-495c out of engagement with the holes in the broach impaction arm 408f.

Figure 71:
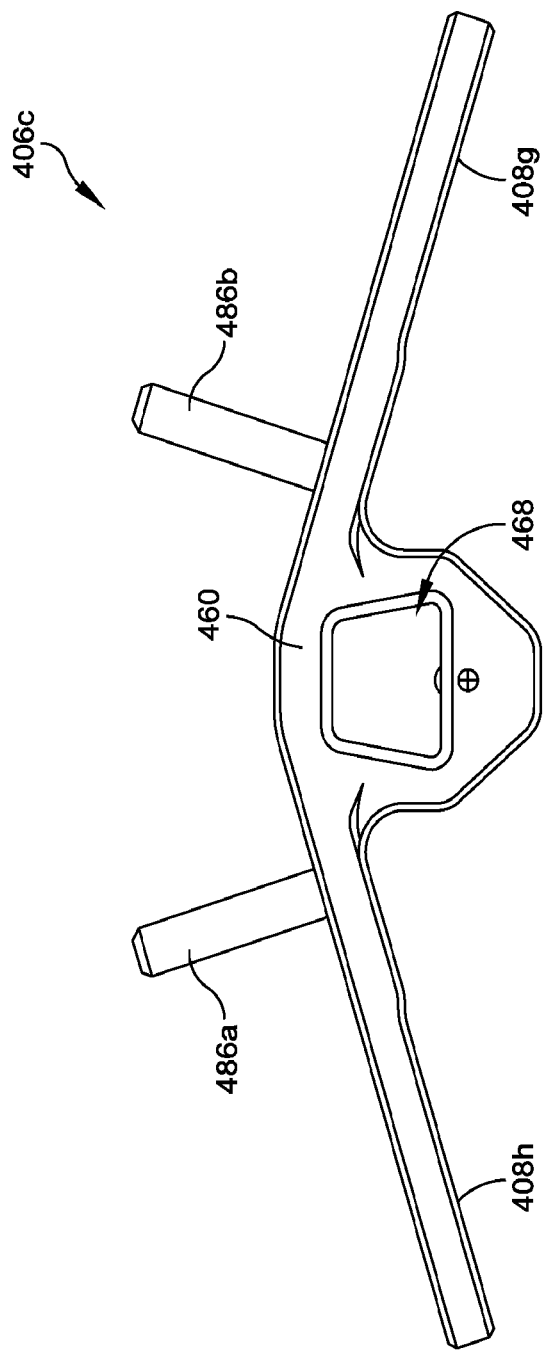
FIG. 71 illustrates a side view of an impactor body, in accordance with some embodiments.
Figure 72:
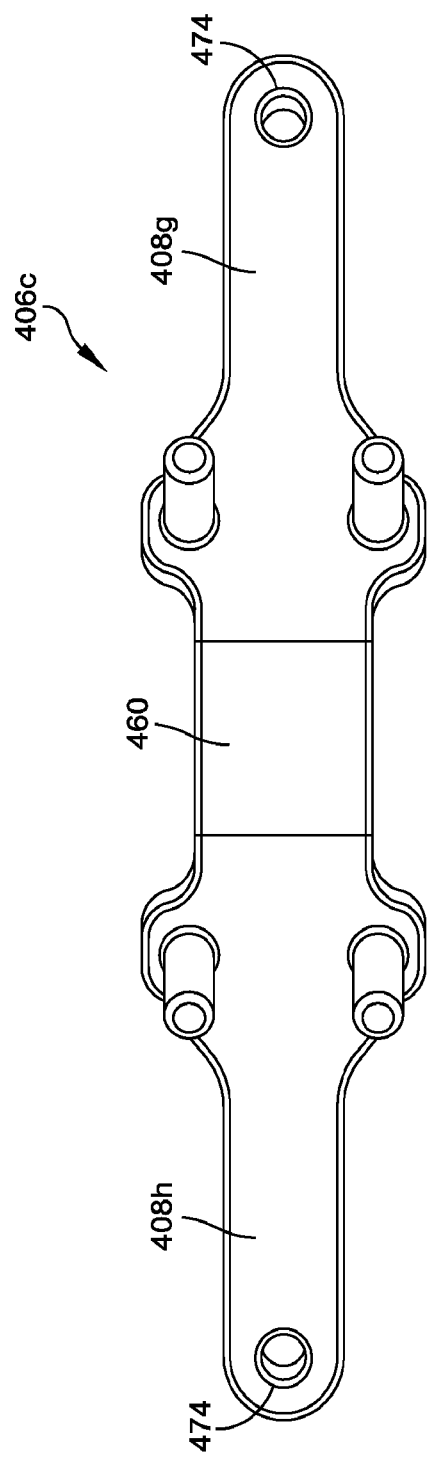
FIG. 72 illustrates a bottom view of the impactor body of FIG. 71, in accordance with some embodiments.

FIGS. 71-72 illustrates an alternative embodiment of an impactor body 406c. The impactor body 406c is similar to the impactor body 406a described above, and similar description is not repeated herein. The impactor body 406c includes a first impaction arm 408g extending from a first side of the housing 460 and a second impaction arm 408h extending from a second side of the housing 460. In some embodiments, the first impaction arm 408g and/or the second impaction arm 408h can be used interchangeably depending on the orientation of the housing 460 when coupled to the offset shaft 404a. In other embodiments, the first impaction arm 408g can have a first angle and/or a first length and the second impaction arm 408h can have a second angle and/or a second length with respect to the housing 460.

Figure 44:
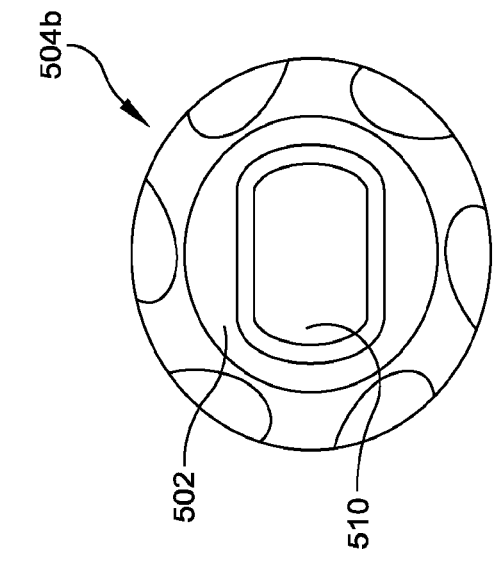
FIG. 44 illustrates a rear view of the first broach of FIG. 42, in accordance with some embodiments.
Figure 42:
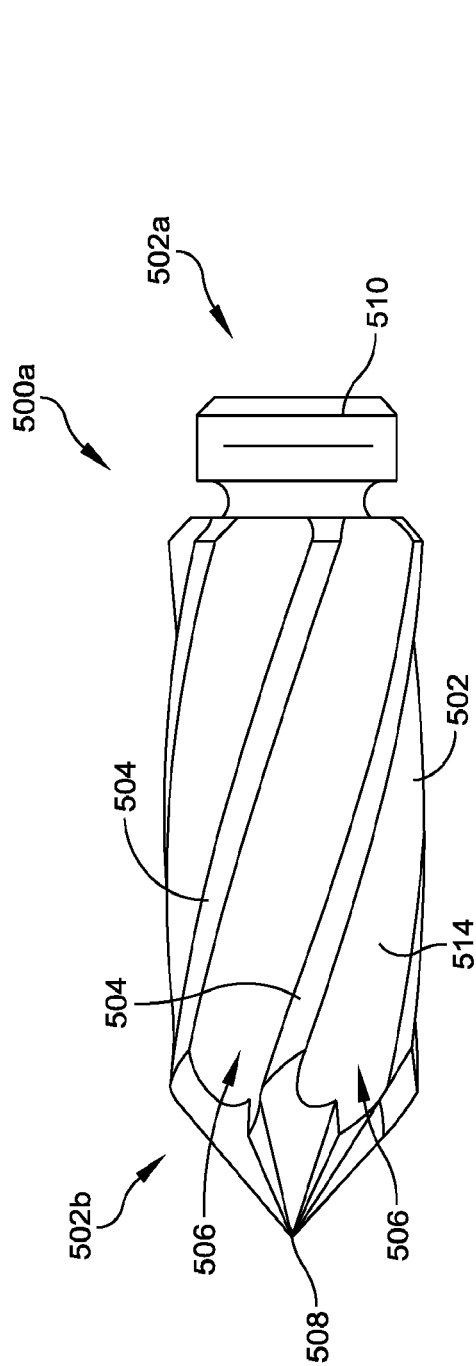
FIG. 42 illustrates a side view of a first broach, in accordance with some embodiments.
Figure 43:
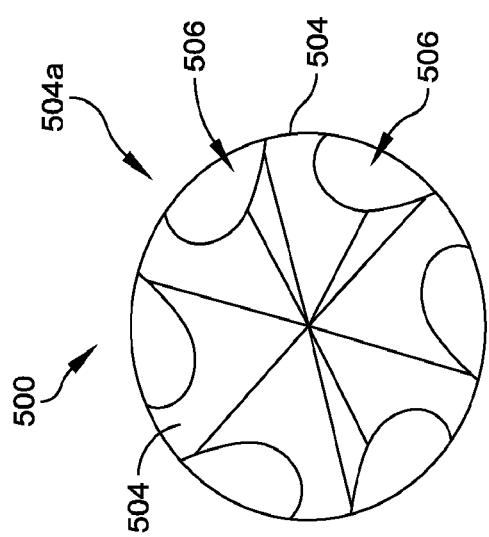
FIG. 43 illustrates a front view of the first broach of FIG. 42, in accordance with some embodiments.

FIGS. 42-44 illustrate a first broach 500a, in accordance with some embodiments. The first broach 500a is similar to the first broach 500 discussed above, and similar description is not repeated herein. The first broach 500a includes a body 502 extending between a proximal end 502a and a distal end 502b. The proximal end 502a includes a fluted portion 514 plurality of flutes 506 defining a plurality of cutting edges 504 disposed in a spiral about the proximal end 502a. The cutting edges 504 define a sharpened tip 508 configured to penetrate a distal end of a resected tibia 106, such as the superior surface of resected tibial portion 108. The distal end 502b of the first broach 500a includes a coupling element 510 configured to couple the first broach 500a to an impaction arm, such as the impaction arm 408f and/or the broach 500a can be connected to an impaction arm 408e by a threaded connection. It will be appreciated that the first broach 500a can be coupled to an impaction arm 408e using any suitable locking element, such as, for example, a force-fit locking element, a threaded locking element, a detent locking element, and/or any other suitable locking element.

The first broach 500a is configured to form a first hole, or pilot hole, in the distal end of the tibia 106. The first broach 500a is coupled to an impaction arm 408 coupled to an impactor body 406 and an impaction force is applied to an impactor head 404. The impaction force is transferred by the impactor body 406 to the impaction arm 408, which drives the first broach 500a into the bone. The impaction force can be applied to the impactor head 404 a plurality of times to drive the first broach 500a into the tibia 106 to a predetermined depth. In some embodiments, the predetermined depth is equal to the length of the fluted portion 514 of the body 502, although it will be appreciated that a greater and/or lesser depth can be used. In some embodiments, the predetermined depth corresponds to a length of a tibial stem implant 150 configured to be inserted into the distal end of the tibia 106.

Figure 45:
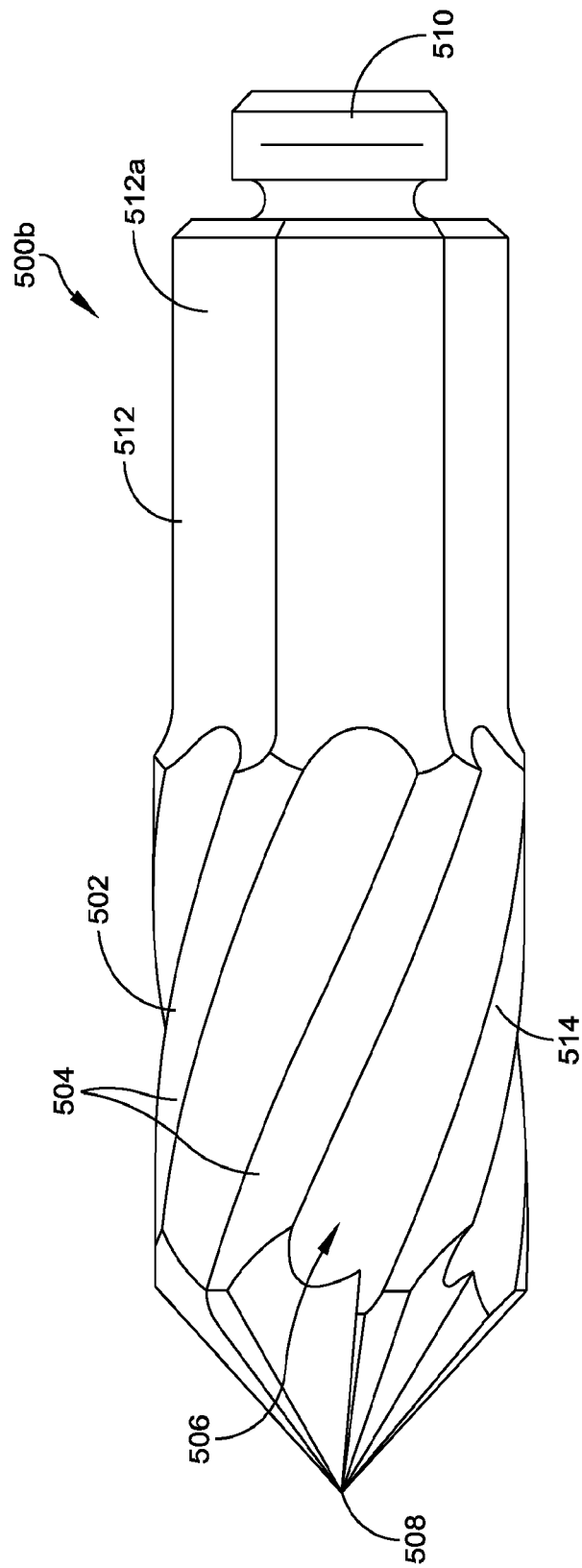
FIG. 45 illustrates a side view of a first broach including an extension shaft, in accordance with some embodiments.

FIG. 45 illustrates a first broach 500b including an extension shaft 512, in accordance with some embodiments. The first broach 500b is similar to the first broach 500a described above, and similar description is not repeated herein. The first broach 500b includes a shaft 512 extending between a fluted portion 514 of the first broach 500b and a coupling element 510. The shaft 512 has a predetermined length corresponding to a predetermined depth of a pilot hole to be formed in a distal end of a tibia 106. In some embodiments, the predetermined depth of the first broach 500b can correspond to a tibial stem implant 150 having additional stem components 156 coupled thereto.

In some embodiments, the extensions shaft 512 is sized and configured to couple to a driver and/or wrench, such as an offset wrench. The wrench is configured to rotate the first broach 500b to couple the first broach 500b to an impaction arm 408 of the offset impactor 400. For example, in some embodiments, the extension shaft 512 includes an outer surface configured to be received within a drive head of an offset wrench.

FIGS. 46-47 illustrate a second broach 550a, in accordance with some embodiments. The second broach 550a includes a fluted portion 552 including a plurality of flutes 556. The fluted portion 556 includes a plurality of teeth 568 extending in a partial-spiral. A shaft 560 is coupled to the fluted portion 552 and extends distally therefrom. A coupling element 562 is disposed at a distal end of the shaft 560. In some embodiments, the coupling element 562 is substantially similar to the coupling element 510 of the first broach 500a, 500b.

The second broach 550a is configured to enlarge the pilot hole formed by the first broach 500a, 500b to a main hole sized and configured to receive a tibial stem implant 150 therein. The second broach 550a is coupled to an impaction arm 408f and/or the second broach 550a can be connected to an impaction arm 408e by a threaded connection. It will be appreciated that the second broach 550a can be coupled to an impaction arm 408e using any suitable locking element, such as, for example, a force-fit locking element, a threaded locking element, a detent locking element, and/or any other suitable locking element. The second broach 550a is coupled to an impaction arm 408f coupled to an impactor body 406b and an impaction force is applied to an impactor head 404a, 404b. The impaction force is transferred by the impactor body 406b to the impaction arm 408f, which drives the second broach 550a into the tibia 106. The impaction force can be applied to the impactor head 404a, 404b a plurality of times to drive the second broach 550a into the tibia 106 to a predetermined depth. In some embodiments, the predetermined depth is equal to the length of the fluted portion 552, although it will be appreciated that a greater and/or lesser depth can be used. In some embodiments, the predetermined depth corresponds to a length of a tibial stem implant 150 configured to be inserted into the distal end of the tibia 106.

Figure 73:
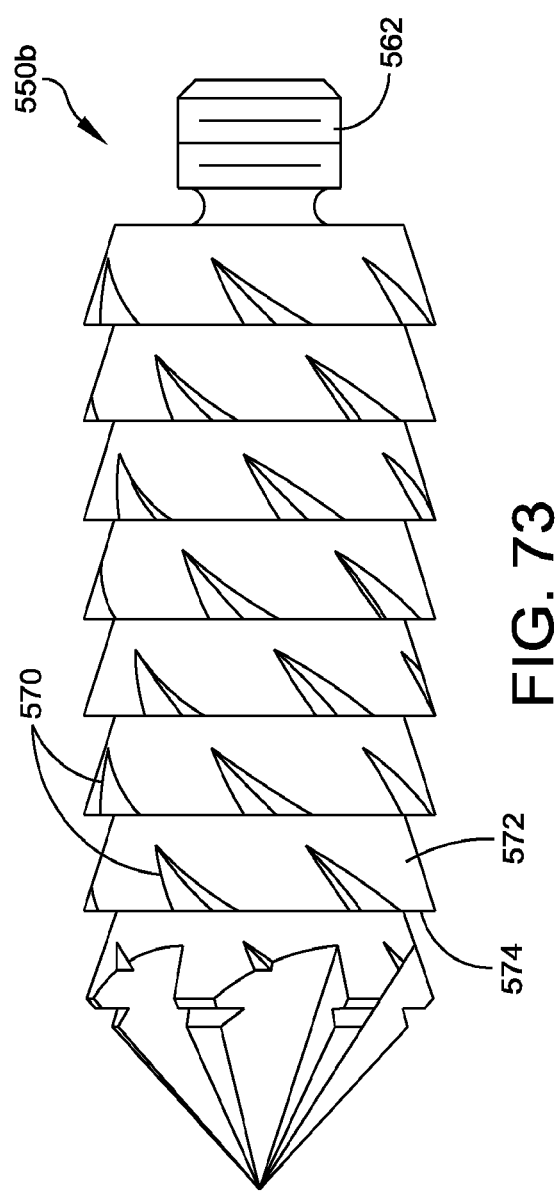
FIG. 73 illustrates a side view of a second broach, in accordance with some embodiments.

FIG. 73 illustrates an alternative embodiment of a second broach 550b, in accordance with some embodiments. The second broach 550b is similar to the second broach 550a described in conjunction with FIGS. 46-47, and similar description is not repeated herein. The second broach 550b includes a plurality of cutting elements 570 configured to enlarge a pilot hole formed by the first broach 500a. In some embodiments, the cutting elements 570 are formed on a plurality of circumferential extensions 572 tapered from a proximal end 564a to a distal end 564b. A proximal surface 574 of the each of the circumferential extensions 572 define a flat.

Figure 49:
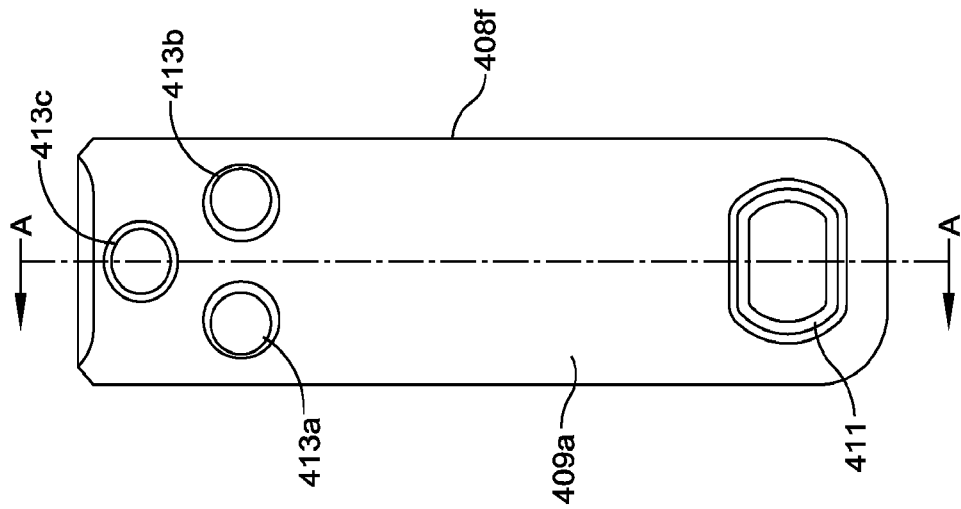
FIG. 49 illustrates a top-down view of the broach impactor arm of FIG. 48, in accordance with some embodiments.
Figure 48:
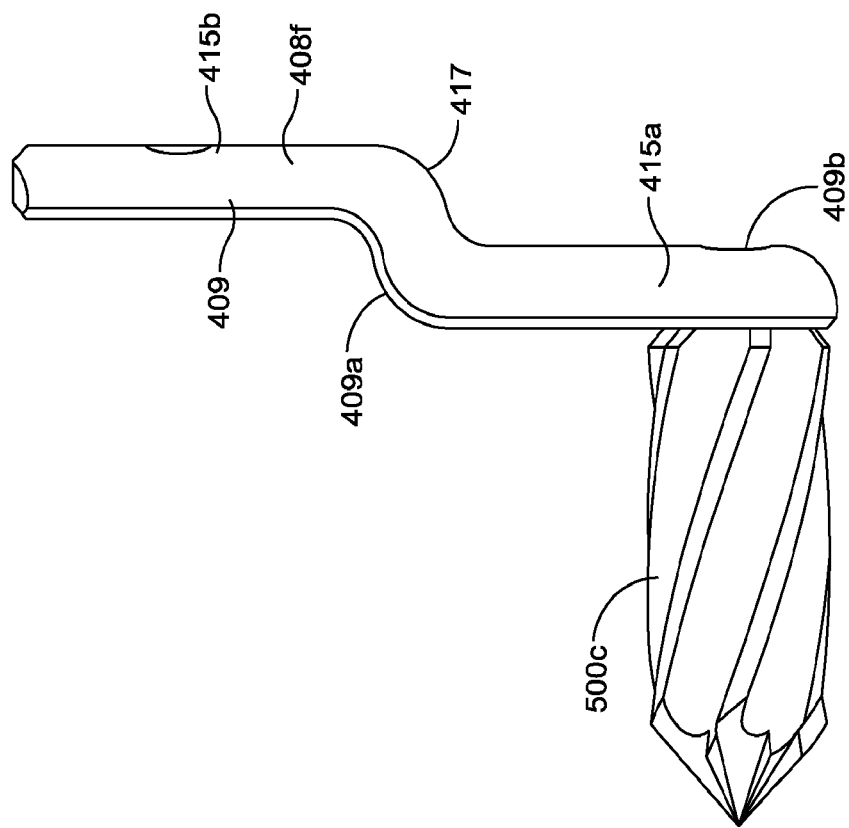
FIG. 48 illustrates a side view of a broach impactor arm having a first broach coupled thereto, in accordance with some embodiments.
Figure 50:
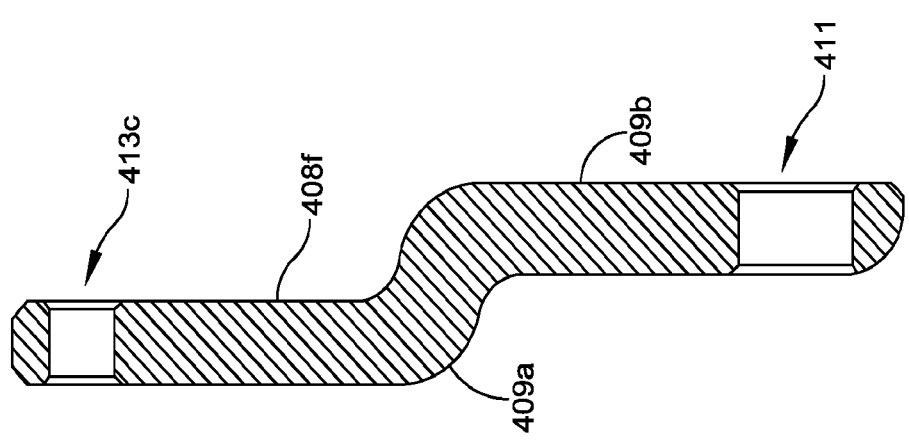
FIG. 50 illustrates a cross-sectional view of the broach impactor arm taken along line A-A of FIG. 48, in accordance with some embodiments.
Figure 51:
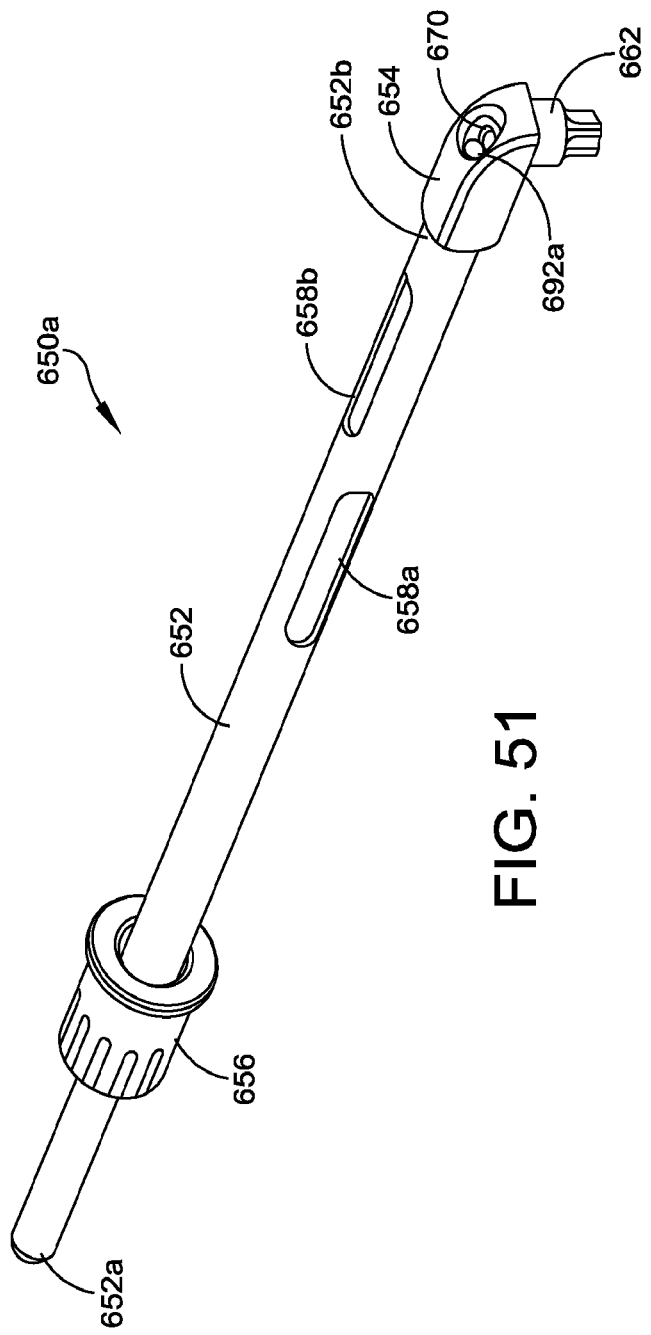
FIG. 51 illustrates a side perspective view of an offset driver, in accordance with some embodiments.
Figure 52:
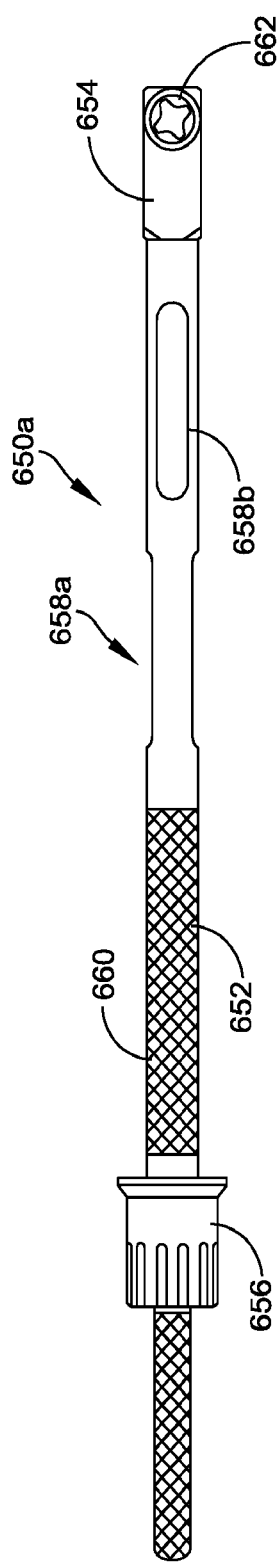
FIG. 52 illustrates a bottom view of the offset driver of FIG. 51, in accordance with some embodiments.
Figure 53:
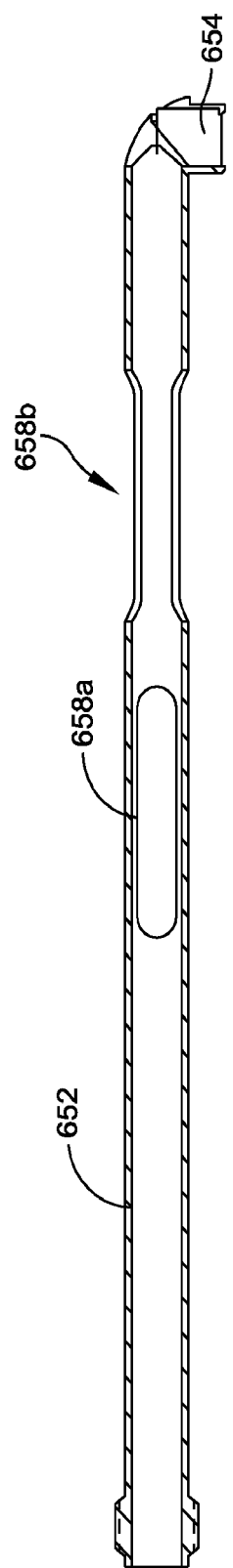
FIG. 53 illustrates a side view of the offset driver of FIG. 51, in accordance with some embodiments.
Figure 56:
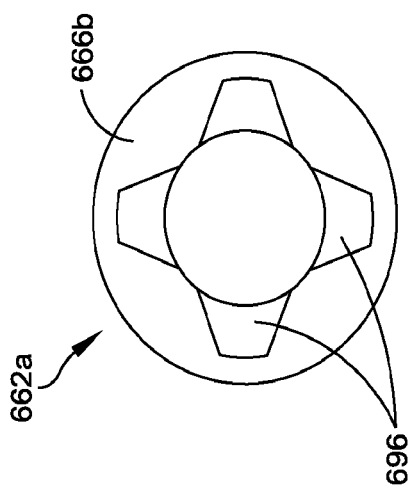
FIG. 56 illustrates a distal view of the offset driver bit of FIG. 54, in accordance with some embodiments.
Figure 55:
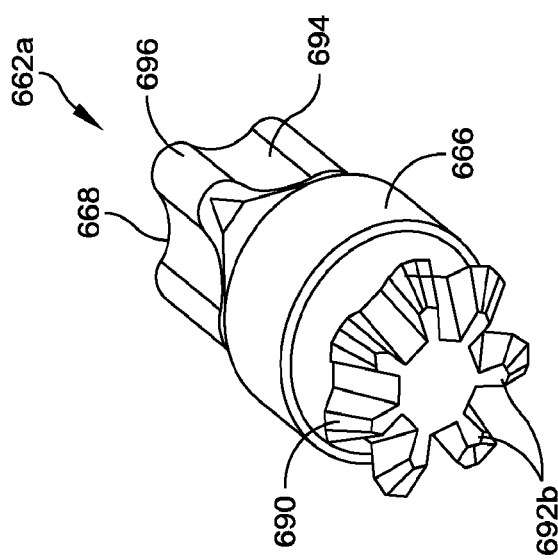
FIG. 55 illustrates an isometric view of the offset driver bit of FIG. 54, in accordance with some embodiments.
Figure 54:
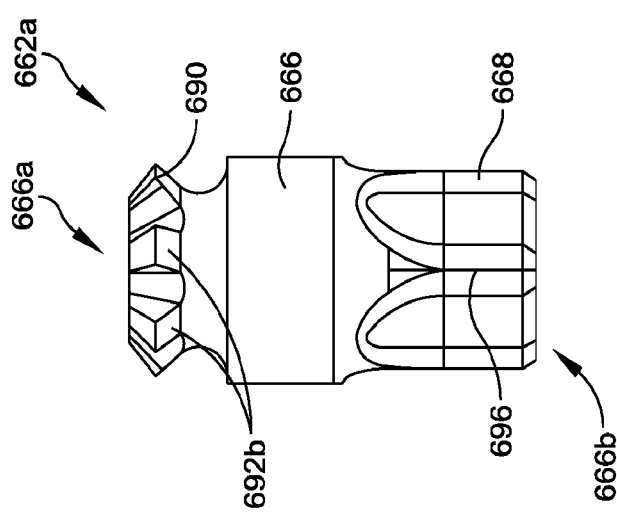
FIG. 54 illustrates a side view of an offset driver bit, in accordance with some embodiments.
Figure 57:
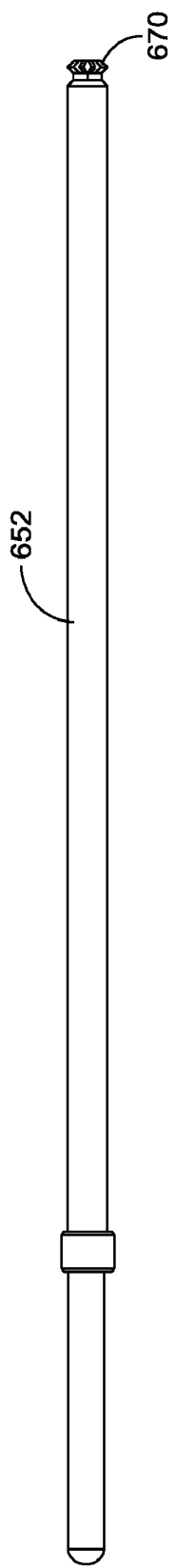
FIG. 57 illustrates a shaft of the offset driver of FIG. 51, in accordance with some embodiments.

FIGS. 48-50 illustrate a broach impaction arm 408f, in accordance with some embodiments. The broach impaction arm 408f includes a body 409 extending between a first surface 409a and a second surface 409b. A first longitudinal portion 415a of the body 409 is disposed in a first plane and a second longitudinal portion 415b is disposed in a second plane. In some embodiments, the first longitudinal portion 415a and the second longitudinal portion 415b are substantially parallel. The first longitudinal portion 415a is coupled to the second longitudinal portion 415b by an offset portion 417. The offset portion 417 extends at an angle between the first longitudinal portion 415a and the second longitudinal portion 415b. For example, in the illustrated embodiment, the offset portion 417 is substantially perpendicular to the first and second longitudinal portions 415a, 415b, although it will be appreciated that the offset portion 417 can have a greater and/or lesser angle with respect to the longitudinal portion 415a, 415b.

In some embodiments, the first longitudinal portion 415a defines a broach hole 411 therethrough. The broach hole 411 is sized and configured to receive a coupling element of a broach therethrough, such as coupling element 510 or 562. The broach hole 411 maintains the broach 500, 550 in a fixed position with respect to the first longitudinal portion 415a.

In some embodiments, the second longitudinal portion 415b defines a plurality of locking holes 413a-413c. Each of the plurality of locking holes 413a-413c are sized and configured to receive a coupling element 495a-495c of an impactor lock 496 therethrough. The locking holes 413a-413c and the impactor lock 496 couple the broach impactor arm 408f to an impactor body 406b. Although embodiments are illustrated herein having locking holes 413a-413c, it will be appreciated that the broach impaction arm 408f can be coupled to an impactor body 406b using any suitable locking element, such as, for example, a force-fit locking element, a threaded locking element, a detent locking element, and/or any other suitable element.

FIGS. 51-57 illustrate a rotational driver 650a, in accordance with some embodiments. The rotational driver 650a is similar to the offset driver 650 described above, and similar description is not repeated herein. The rotational driver 650a includes a longitudinal housing 652 sized and configured for insertion into a resected tibial portion 108 through an anterior opening. In some embodiments, the longitudinal housing 652 defines one or more slots 658a, 658b therethrough.

A head 654 is coupled to a distal end 652b of the longitudinal housing 652. The head 654 has a hole sized and configured to receive a transverse drive bit 662 therein. The transverse driver bit 662 is substantially disposed at an angle with respect to the longitudinal housing 652, such as, for example, a 90° angle, although it will be appreciated that a greater and/or lesser angle is possible and is within the scope of this disclosure. The inline rotation shaft 670 includes a first set of gear teeth 692a and the transverse driver bit 662a includes a second set of gear teeth 692b sized and configured to be coupled to the first set of gear teeth 692a. In some embodiments, the first gear teeth 692a and the second gear teeth 692b have a 1:1 ratio, although it will be appreciated that the gear teeth 692a, 692b can have a greater and/or lesser gear ratio.

Rotation of the inline rotation shaft 670 causes complimentary rotation of the driver bit 662a. In some embodiments, the driver bit 662a includes a drive head 668 sized and configured to interact with a driver cavity formed in one or more tibial stem components 152-156. In some embodiments, the drive head 668 includes a plurality of drive elements 696 defining a predetermined shape, such as, for example, a star-head drive, a hexagonal drive, and/or any other suitable drive shape. In some embodiments, a gear portion 690 of the driver bit 662 is separated from a drive head 668 by a smooth shaft 666, although it will be appreciated that the smooth shaft 666 can be omitted and the drive head 668 can be coupled directly to the gear portion 690.

In some embodiments, the rotational driver 650*a* includes a locking knob 656 disposed adjacent to the proximal end 652*a* of the inline rotation shaft 670. The inline rotation shaft 670 is inserted through the longitudinal housing 652 and coupled thereto with the locking knob 656, such that the inline rotation shaft 670 can rotate with respect to the longitudinal housing 652. In use, a surgeon or other user can rotate the inline rotation shaft 670 while maintaining the longitudinal housing 652 (in the user's hand) in a fixed position. In some embodiments, a portion of the longitudinal housing 652 includes a gripping feature 660*a* configured to provide additional friction to a user rotating the inline rotation shaft 670, which includes a gripping feature 660*b*.

Figure 68:
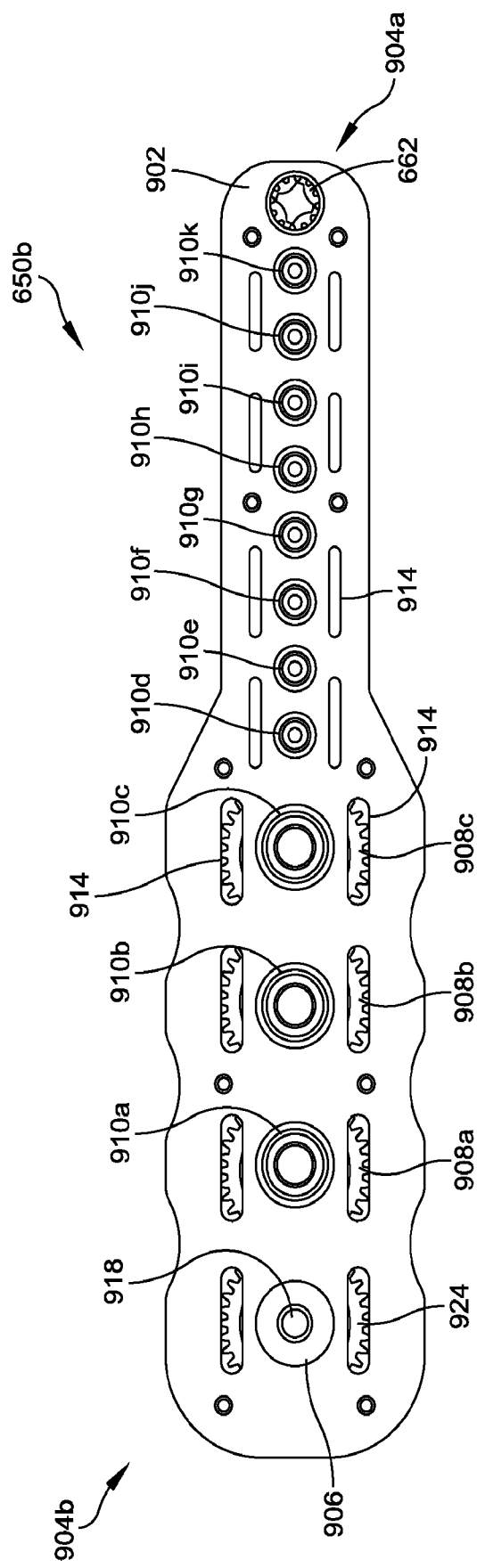
FIG. 68 illustrates a top view of an offset driver, in accordance with some embodiments.
Figure 69:
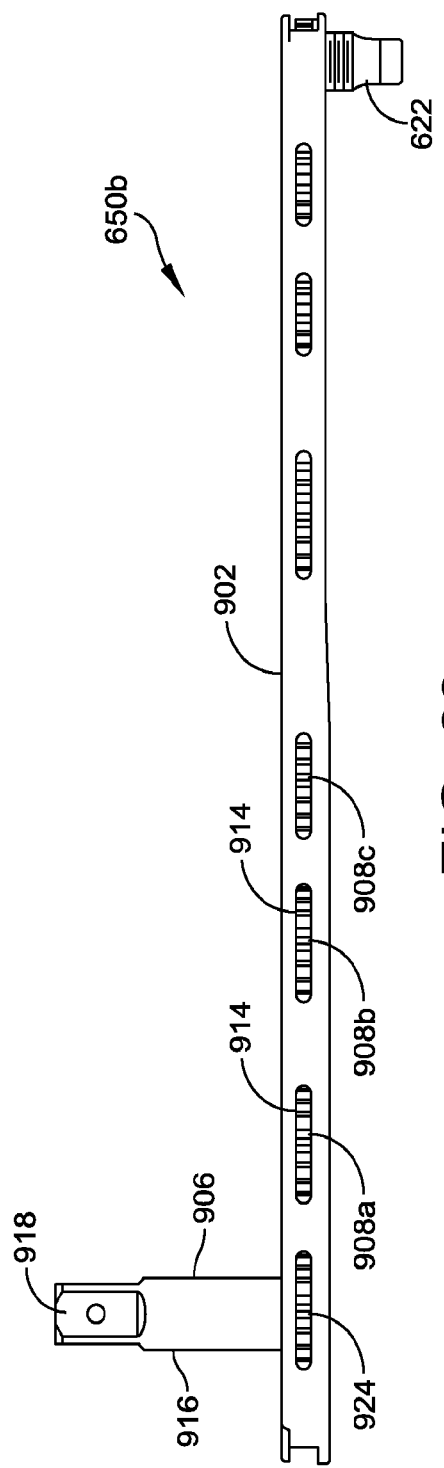
FIG. 69 illustrates a side view of the offset driver of FIG. 68, in accordance with some embodiments.
Figure 70:
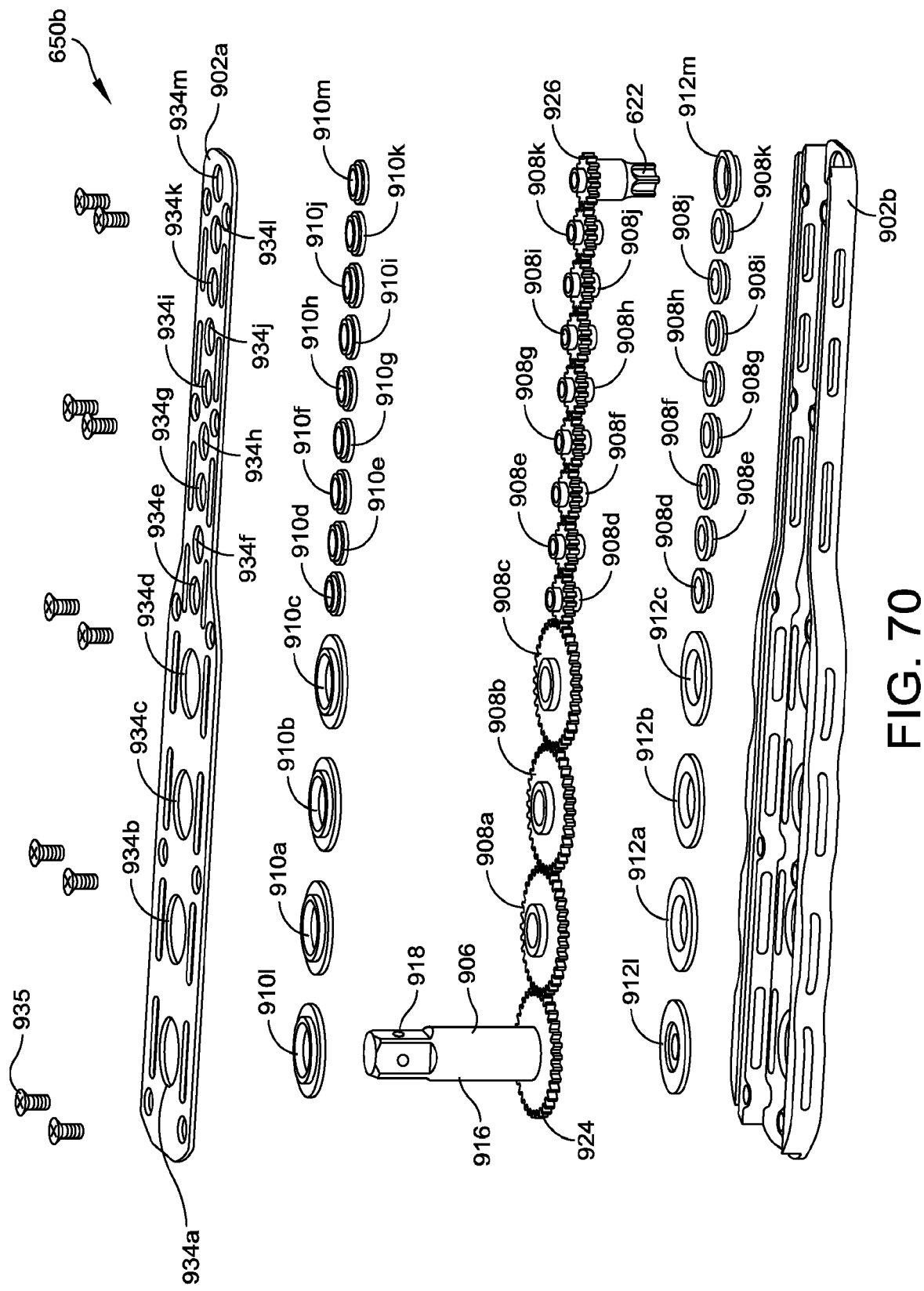
FIG. 70 illustrates an exploded view of the offset driver of FIG. 68, in accordance with some embodiments.

FIGS. 68-70 illustrate an alternative embodiment of an offset driver 650*a*, in accordance with some embodiments. The offset driver 650*b* is similar to the rotational driver 650*a* discussed above, and similar description is not repeated herein. The offset driver 650*b* includes a body 902 defined by a first half 902*a* and a second half 902*b*. An offset drive bit 662 is coupled to the offset driver 650*b* at a proximal end 904*a*. The offset driver 650*b* is configured to transfer a rotational force applied to a drive coupling 906 positioned a distal end 904*b* to the driver bit 662. In some embodiments, the rotation force is transferred by a plurality of gears 908*a*-908*k* (collectively "transfer gears 908"). The transfer gears 908 includes a first set of gears 908*a*-908*c* having a first diameter and a first gear ratio and a second set of gears 908*d*-908*k* having a second diameter and a second gear ratio. Although embodiments are illustrated herein including a first set and a second set of transfer gears 908, it will be appreciated that the driver 650*b* can include any suitable number of gears having any number of diameters and/or gear ratios.

In some embodiments, a drive coupling 906 is configured to receive a rotational force. The rotation force can be applied at a coupling portion 918. The coupling portion 918 is configured to couple to an automatic and/or manual rotation device, such as a drill, wrench, socket, and/or other device. The coupling portion 918 is coupled to a coupling gear 924 by a shaft 916. The coupling gear 924 is positioned in an operational abutting relationship with a first transfer gear 908*a*. Transfer gears 908 are each positioned in a linear abutting relationship with a previous and/or subsequent transfer gear to transfer the rotational force from the distal-most transfer gear 908*a* to a proximal-most (or last) transfer gear 908*k*. The last transfer gear 908*m* is positioned in an operational abutting relationship with a drive gear 926 coupled to the driver bit 662. The drive gear 926 transfers the rotational force to the drive bit 662.

In some embodiments, one or more bushings 910*a*-910*m*, 912*a*-912*m* (collectively "bushings 910, 912") can be positioned above and/or below the transfer gears 908.

The one or more bushings 910, 912 extend partially through bushing openings 934*a*-934*m* formed in the first and/or second body half 902*a*, 902*b*. The bushings 910, 912 provide for rotation of the transfer gears 908 without interference from the body halves 902*a*, 902*b*. In some embodiments, the bushing openings 934*a*-934*m* in the first half 902*a* are vertically aligned with bushing openings in the second half 902*b*.

In some embodiments, each of the body halves 902*a*, 902*b* define a plurality of screw holes 936. A plurality of screws 935 can be inserted through one or more of the plurality of screw holes 936 to couple the first half 902*a* to the second half 902*b*. In some embodiments, one or more of the body halves 902*a*, 902*b* include a one or more openings 914. The openings 914 are configured to provide inlet and/or outlet of a fluid during a sanitizing process. Although embodiments are illustrated with openings 914, it will be appreciated that such openings can be omitted in some embodiments.

Figure 58:
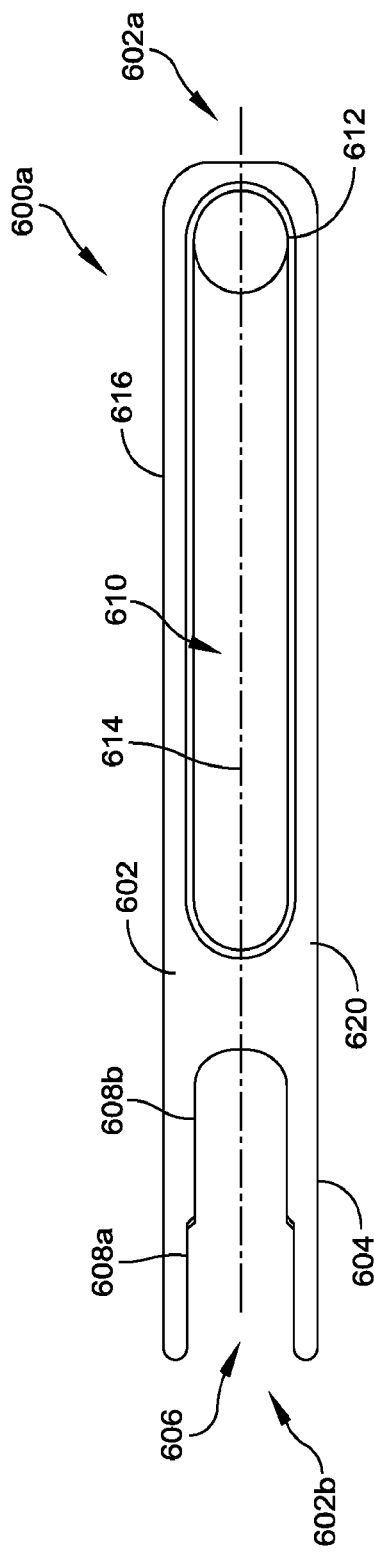
FIG. 58 illustrates a top view of an offset wrench, in accordance with some embodiments.
Figure 59:
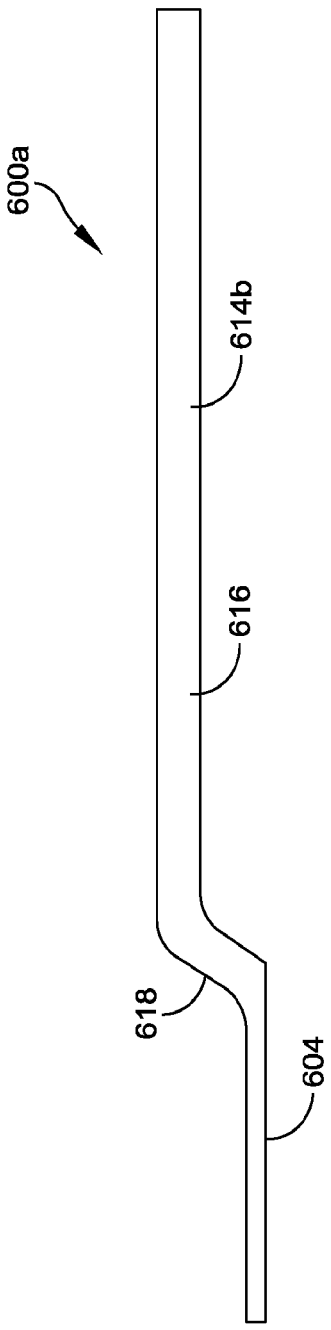
FIG. 59 illustrates a side view of the offset wrench of FIG. 58, in accordance with some embodiments.
Figure 60:
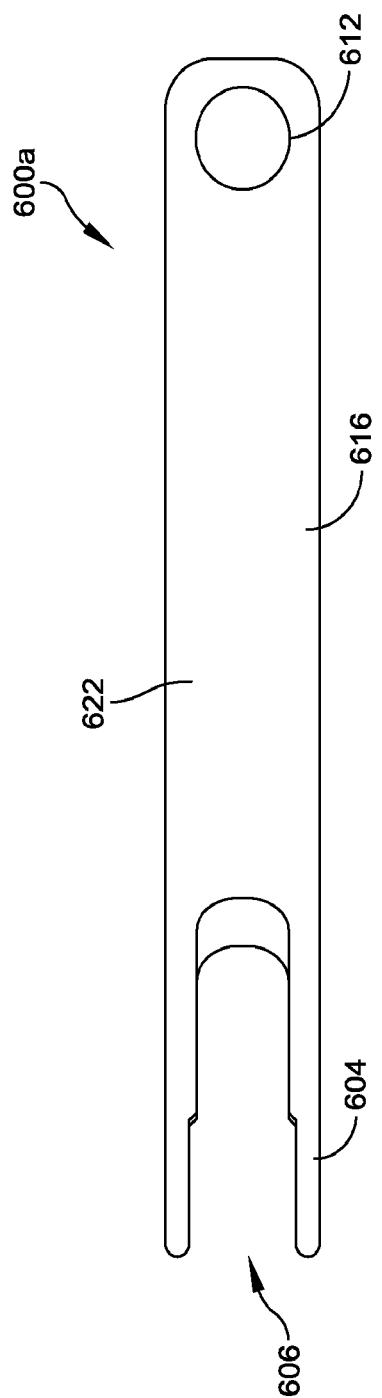
FIG. 60 illustrates a bottom view of the offset wrench of FIG. 58, in accordance with some embodiments.

FIGS. 58-60 illustrate an offset wrench 600*a*, in accordance with some embodiments. The offset wrench 600*a* can be used with an offset driver 650, 650*a*, to couple elements of a tibial stem implant 150. The offset wrench 600*a* includes a longitudinal body 602 extending along a longitudinal axis 614 from a proximal end 602*a* to a distal end 602*b* and between a first surface 620 and a second surface 622. The proximal end 602*a* of the longitudinal body 602 defines a handle portion 616. The handle portion 616 can define a slot 610. The handle portion 616 can further include a finger hole 612 extending through the body 602. In some embodiments, scallops may be disposed on a handle portion 616 to assist a user in gripping the offset wrench 600*a*.

Figure 62:
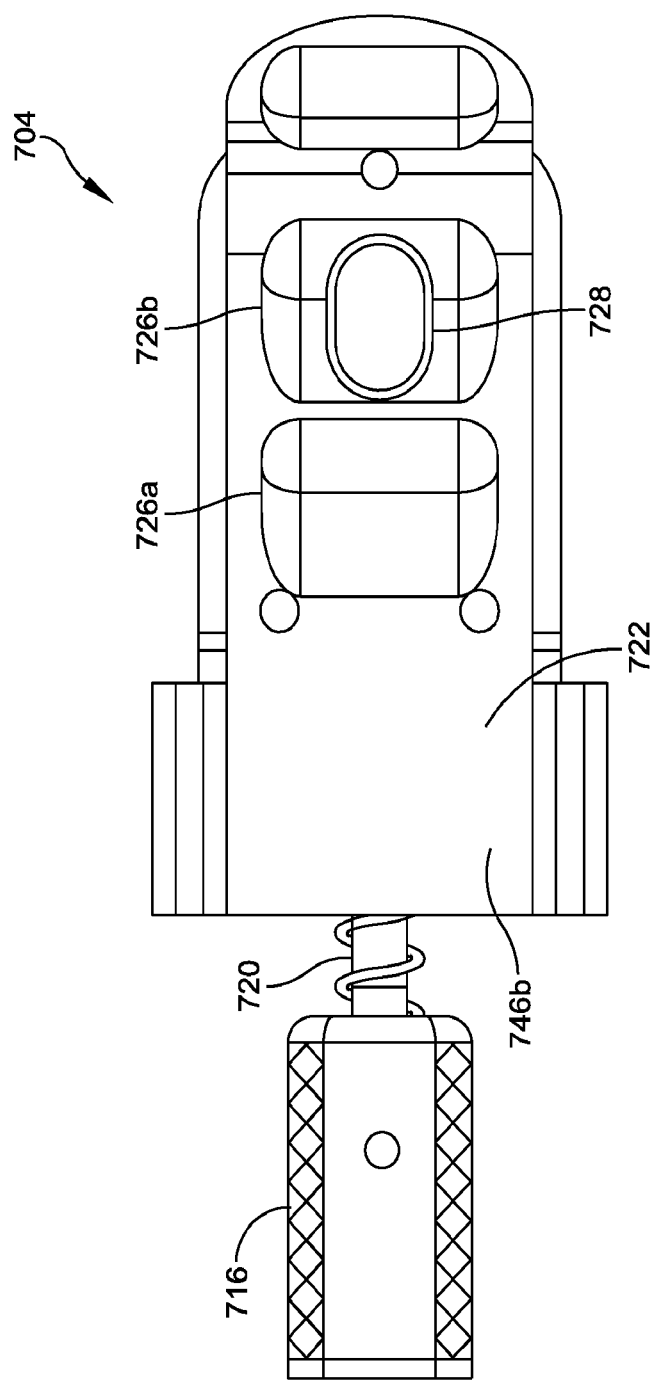
FIG. 62 is a bottom perspective view of an impaction insert of the implant assembly of FIG. 61, in accordance with some embodiments.

In some embodiments, the body 602 includes a coupling portion 604 extending generally along the longitudinal axis 614. The coupling portion 604 defines a slot 606 extending from a distal end 602*b* of the body 602 into the offset wrench 600*a*. In some embodiments, the slot 606 includes a first portion 608*a* sized and configured to receive an outer surface of a stem component 152-156, such as a hexagonal outer wall. In some embodiments, the slot 606 includes a second portion 608*b* sized and configured to provide clearance for one or more additional surgical instruments, such as the impaction insert 704 illustrated in FIGS. 62-64.

In some embodiments, the handle portion 616 is disposed in a first plane and the coupling portion 604 is disposed in a second plane. The handle portion 616 can be coupled to the coupling portion 604 by an offset connector 618. The offset connector 618 extends between the handle portion 616 and the coupling portion at a predetermined angle with respect to the longitudinal axis. The predetermined angle can be in the range of about 30-90°, 45-90°, 45-60°, and/or any other suitable range. In some embodiments, the coupling portion 604 is configured to be positioned against an anterior surface of a tibia 106 to prevent rotation of the tibial stem components 152-156 during tightening and/or loosening of the additional tibial stem components 154-156. Although embodiments are illustrated with an offset wrench 600*a*, it will be appreciated that a flat wrench can be used to couple one or more stem components 152-156.

FIGS. 61-64 illustrate a tray assembly 700, in accordance with some embodiments. The tray assembly 700 includes and implant 702 coupled to an impaction insert 704. The implant 702 is similar to the tibial tray 702 described above, and similar description is not repeated herein. In some embodiments, the implant 702 has an oblong shape including a first side 705 and a second side (not shown) which is curved and disposed on an opposite side of the implant 702. A longitudinal surface 707 extends between the first side 705 and the second side. In some embodiments, the implant 702 can include a single continuous side 705 defining a circle, oval, and/or other continuous shape.

A head or protrusion 710 extends from an upper side 706a and is configured to engage stem component 152-156 of a tibial stem implant 150. For example, in some embodiments, head 710 is tapered such that it is configured to form a Morse taper with a corresponding recess of a stem component 152-156 and/or additional components of an ankle replacement and/or other implant system. In some embodiments, projection 710 is cylindrical, i.e., not tapered, and includes threads, a bayonet coupling, and/or other attachment or coupling means for engaging a complementary feature of a stem component 156 and/or another component of an ankle replacement system. The implant 702 can be coupled to a stem component 152-154 of a multi-component prosthesis using screws, bolts, and/or other suitable fasteners.

In some embodiments, the geometry of the implant 702 can be complementary to other implant components or to the geometry of intramedullary channels or cavities. The bottom surface 706b of the implant 702 includes a contoured surface defining a channel that extends inwardly between the first side 705 and a second side. The implant 702 is sized and configured to receive an articulating surface (not shown) therein. Examples of tibial platforms including similar implants are described in U.S. Pat. No. 8,715,362, issued on May 6, 2014 and entitled "Ankle Replacement System" and U.S. patent application Ser. No. 15/251,830, filed on Aug. 30, 2016 and entitled "Revision Total Ankle Implants," each of which is hereby incorporated by reference in its entirety. The articulating surface is sized and configured to articulate against a talar articulation surface, such as, for example, the upper surface of a talar dome implant.

The implant 702 has a predetermined thickness extending from the upper surface 706a to the lower surface 706b. The implant 702 can have any suitable predetermined thickness, such as, for example, 4 mm, 8 mm, 12 mm, 16 mm, and/or any suitable thickness. In some embodiments, the implant 702 has a first predetermined width near a bottom surface 706b and a second predetermined width near a top surface 706a. The first predetermined width can be greater than, less than, and/or equal to the second predetermined width. In some embodiments, the second predetermined width is less than the first predetermined width such that the thickness of the implant portion 702 tapers from a bottom surface 706b to a top surface 706a. In some embodiments, the predetermined widths are selected to match the width of a primary tibial tray removed during a total ankle revision.

The insertion portion 704 includes a body 722. The 722 body has an oblong shape generally extending between an upper surface 746a and a lower surface 746b. The body 722 is sized and configured to be received within the channel defined between the side walls 705 of the implant.

In some embodiments, the body 722 defines a slot 728 extending from a bottom surface 746b at least partially into the body 722. The slot 728 is sized and configured to interact with an impactor element 770, as shown in FIG. 9. In some embodiments, the impactor element 770 is configured to transfer an impaction force to the impaction insert body 722. The impaction force drives the implant 702 into a fixed engagement with a stem component 156 of a tibial stem implant 150.

In some embodiments, the body 722 defines one or more grooves 726a, 726b extending from a bottom surface 746b at least partially into the body 722. The grooves 726a, 726b are sized and configured to interact with an impactor arm, such as impactor arm 1102a, 1102b, as shown in FIG. 10. In some embodiments, the impactor arm 1102a, 1102b includes an impaction element sized and configured to be received within one of the grooves 726a, 726b and to transfer an impaction force to the impaction insert 704. The impaction force drives the implant 702 into a fixed engagement with a stem component 156 of a tibial stem implant 150.

In some embodiments, the insertion portion 704 includes a spring-loaded insertion element 716. The spring-loaded insertion element 716 includes a head 718 and a spring-loaded shaft 720 extending from a distal end of the head 718. The head 718 is fixedly coupled to the spring-loaded shaft 720 such that longitudinal movement of the head 718 causes complimentary longitudinal movement of the spring-loaded shaft 720. The spring-loaded shaft 720 extends from the head 718 distally to a guide body 730 coupled to the body 722 of the insertion portion 704. The spring loaded shaft 720 is retained within a channel 732 defined by the guide body 730. The channel 732 includes a retention element 736 configured to retain the spring-loaded shaft 720. For example, in some embodiments, the retention element 736 includes a reduced diameter portion of the channel 732 configured to prevent advancement of a spring-loaded shaft 720 in a proximal direction beyond a predetermined length.

In some embodiments, a spring-loaded shaft 720a includes a body 752 generally extending from a proximal end 754a to a distal end 754b along a longitudinal axis 764. The body 752 includes a smooth shaft portion 760 sized and configured for insertion into a channel 766 defined in the head 718 of a spring-loaded coupling element 716. A stop 758 is coupled to the body 752. The stop is sized and configured to interact with retention element 736 to maintain the shaft 720 within a channel 732 defined by the impaction insert 704. An implant driving portion 756 extends from the stop element 758. The implant driving portion 756 is configured to couple the implant 702 to the impaction insert 704.

Figure 66:
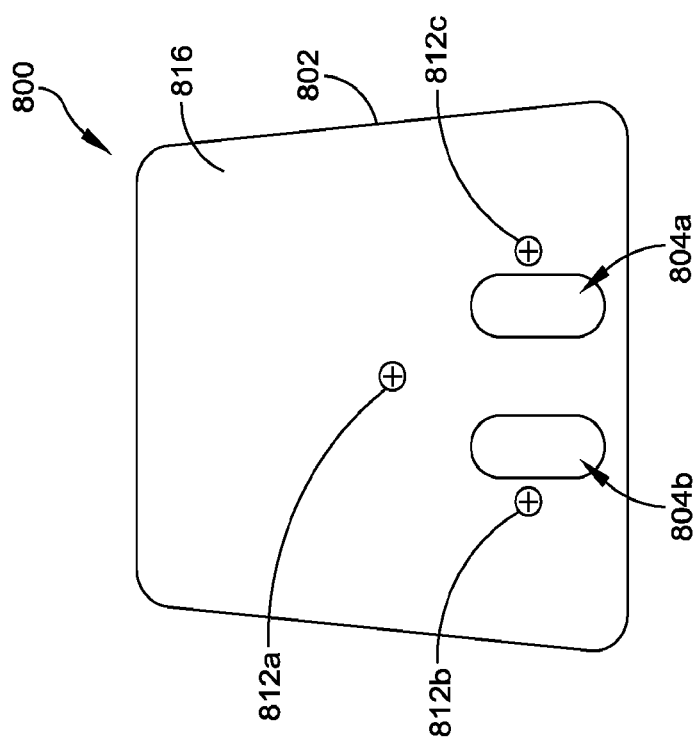
FIG. 66 illustrates a bottom view of the talar protector of FIG. 65, in accordance with some embodiments.
Figure 67:
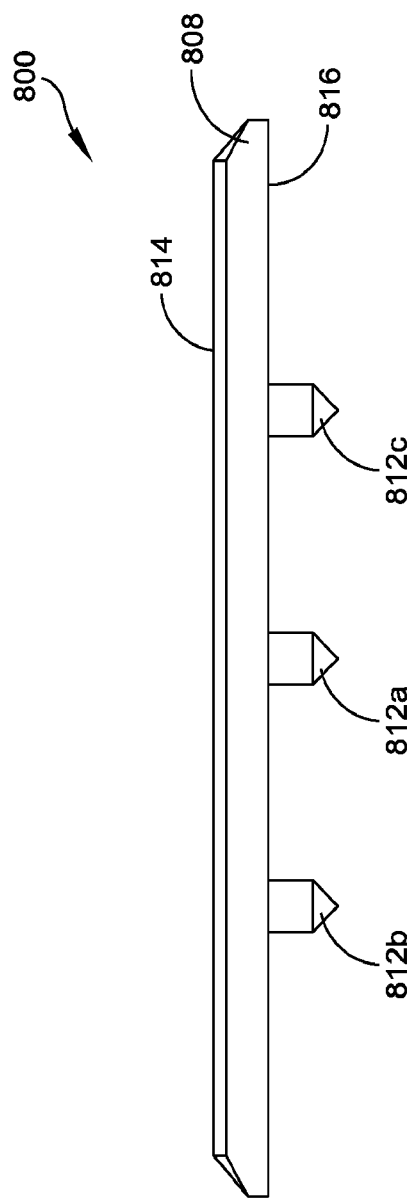
FIG. 67 illustrates a front view of the talar protector of FIG. 65, in accordance with some embodiments.

FIGS. 65-67 illustrate a talar protector 800, in accordance with some embodiments. The talar protector 800 is configured to prevent damage to a talus 104 during the anterior approach method 1000 discussed above. For example, in some embodiments, the talar protector 800 extends over a portion of a talus 104 to protect the talus 104 from accidental damage from the impactor body 406 and/or any other element. The talar protector 800 includes a body 802 including lateral sides 806a, 806b each extending between a proximal side 808 and a distal side 810. The body 802 has a thickness extending between an upper surface 814 and a lower surface 816. The body 802 has a perimeter configured to be complimentary to the perimeter of a resected talus, such as talus 104. In some embodiments, the lateral sides 806a, 806b include non-parallel sides such that the talar protector 800 has a generally trapezoidal shape, although it will be appreciated that the talar protector 800 can have any suitable shape such as a rectangular, circular, trapezoidal, ovoid, etc., and is within the scope of this disclosure.

In some embodiments, the talar protector 800 includes one or more slots 804a defined in the body 802 and extending from the upper surface 814 to a lower surface 816. The slots 804a, 804b each define a longitudinal opening sized and configured to receive a guide element therein to position the talar protector 800 with respect to a resected talus 104. The slots 804a, 804b can be sized and configured to receive an instrument to remove the talar protector 800 from a talus 104. In some embodiments, the slots 804a, 804b are omitted and the body 802 defines a continuous planar surface.

In some embodiments, a plurality of coupling protrusions 812a-812c extend from a lower surface 816 of the talar protector. The coupling protrusions 812a-812c are arranged in a triangular orientation, although it will be appreciated that the coupling protrusions 812a-812c can have any suitable arrangement. The coupling protrusions 812a-812c maintain the talar protector 800 in a fixed position with respect to the talus 104 during the anterior approach method 1000 described in conjunction with FIGS. 2-11.

Although the devices, kits, systems, and methods have been described in terms of exemplary embodiments, they are not limited thereto. Rather, the appended claims should be construed broadly, to include other variants and embodiments of the devices, kits, systems, and methods, which may be made by those skilled in the art without departing from the scope and range of equivalents of the devices, kits, systems, and methods.

What is claimed is:

1. A method of ankle replacement, comprising:
    forming an anterior cut in a bone;
    forming a stem hole in a distal end of the bone using a plurality of broaches positioned against the distal end of the bone through the anterior cut;
    inserting a first portion of a stem into the stem hole through the anterior cut in the bone;
    inserting a second portion of the stem into the stem hole through the anterior cut in the bone;
    coupling the first portion to the second portion using a coupling device inserted through the anterior cut in the bone; and
    impacting the stem implant into the stem hole by applying an impaction force to an offset impactor, wherein the offset impactor comprises a body including a longitudinal section having a first transverse arm coupled to a first end and a second transverse arm coupled to a second end, wherein the first transverse arm and the second transverse arm define a space therebetween;
    an impactor surface configured to be coupled to the first transverse arm, the impactor surface configured to receive the impaction force; and
    an impactor body configured to be coupled to the second transverse arm, wherein the impaction force is transferred from the first transverse arm to the second transverse arm by the longitudinal section, wherein the offset impactor is configured to convert the impaction force to a linear impaction force.

2. The method of ankle replacement of claim 1, wherein forming the stem hole comprises:
    coupling a broach guide to an anterior surface of the bone;
    positioning a first of the plurality of broaches with respect to the broach guide;
    forming a first broach hole in the distal end of the bone;
    positioning a second of the plurality of broaches with respect to the broach guide; and
    forming the stem hole in the distal end of the bone.

3. The method of ankle replacement of claim 2, wherein positioning the first of the plurality of broaches comprises coupling the first of the plurality of broaches to the offset impactor, and wherein positioning the second of the plurality of broaches comprises coupling the second of the plurality of broaches to the offset impactor.

4. The method of ankle replacement of claim 2, comprising coupling the broach guide to the bone using at least one temporary fixation device prior to positioning the first of the plurality of broaches.

5. The method of ankle replacement of claim 1, wherein each of the plurality of broaches comprises a fluted broach.

6. The method of ankle replacement of claim 1, wherein the coupling device comprises an offset driver.

7. The method of ankle replacement of claim 6, wherein the offset driver comprises a 90° drive head.

8. The method of ankle replacement of claim 1, comprising coupling an implant to the second portion of the stem.

9. The method of ankle replacement of claim 6, wherein the offset driver, comprises
    an offset driver body having a first half and a second half, the first half defining a first hole at a proximal end and the second half defining a second hole at a distal end;
    a drive coupling positioned between the first half and the second half of the offset driver body, wherein a portion of the drive coupling extends through the first hole and is configured to be coupled to a driver;
    a drive bit positioned between the first half and the second half of the offset driver body, wherein a portion of the drive bit extends through the second hole; and
    at least one gear positioned between the drive coupling and the drive bit, wherein the at least one gear is configured to transfer rotation of the drive coupling to the drive bit.

10. The method of ankle replacement of claim 9, comprising a first gear having a first gear ratio and a second gear having a second gear ratio, wherein the first gear is positioned adjacent to the drive coupling and the second gear is positioned adjacent to the drive bit.

11. The method of ankle replacement of claim 10, wherein the drive coupling comprises a drive gear coupled to a first end, wherein a drive gear ratio is equal to the first gear ratio.

12. The method of ankle replacement of claim 10, wherein the drive bit comprises a bit gear coupled to a first end, wherein a bit gear ratio is equal to the second gear ratio.

13. The method of ankle replacement of claim 9, wherein at least one of the first half or the second half of the body define a sanitization opening configured to provide inlet and outlet of a fluid during a sanitizing process.

14. The method of ankle replacement of claim 9, wherein the at least one gear is positioned in a linear abutting relationship with the drive coupling and the drive bit.

15. The method of ankle replacement of claim 6, wherein the offset driver comprises:
    a drive coupling configured to receive a rotational force;
    a plurality of gears operatively coupled to the drive coupling; and
    a drive bit operatively coupled to at least one of the plurality of gears, wherein the plurality of gears are configured to transfer the rotational force from the drive coupling to the drive bit.

16. The method of ankle replacement of claim 1, wherein the impactor body comprises a spring-loaded impactor body.

17. The method of ankle replacement of claim 1, wherein the impactor body comprises:
    a first surface defining an opening sized and configured to receive the second transverse arm;
    a locking element positioned at least partially within the body, the locking element configured to maintain the second transverse arm in a fixed engagement with the body when the second transverse arm is positioned within the opening; and
    an extension arm extending substantially along a longitudinal axis from the body.

18. The method of ankle replacement of claim 1, wherein the impactor surface comprises a solid impactor surface.

19. The method of ankle replacement of claim 1, wherein the impactor body is configured to be coupled to each of the plurality of broaches, and wherein the linear impactor force is generated on a longitudinal axis aligned with a longitudinal axis of a broach when the broach is coupled to the impactor body.

20. The method of ankle replacement of claim 19, wherein the plurality of broaches includes a pilot broach and an enlarging broach.

21. The method of ankle replacement of claim 1, wherein the impactor body is further configured to couple to a broach guide, and wherein the broach guide positions the offset impactor with respect to the bone.

22. The method of ankle replacement of claim 1, wherein the impactor body is configured to be coupled to a tray implant impaction insert, wherein the tray implant impaction insert is configured to transfer the linear impaction force to an implant.

23. The method of ankle replacement of claim 22, wherein the tray implant impaction insert comprises:
   a first surface configured to engage a tray implant and a second surface configured to engage the offset impactor, wherein the impaction force applied to the offset impactor is transferred to the tray implant; and
   a locking element configured to couple the tray implant to the body of the tray implant impaction insert.

24. The method of ankle replacement of claim 23, wherein the second surface defines a first groove and a second groove extending from the second surface into the body of the tray implant impaction insert, wherein the first groove and the second groove are each sized and configured to engage the offset impactor.

25. The method of ankle replacement of claim 24, wherein the first groove corresponds to a first size of the tray implant and the second groove corresponds to a second size of the tray implant.

26. The method of ankle replacement of claim 23, wherein the locking element comprises a spring-loaded locking element.

27. The method of ankle replacement of claim 26, wherein the locking element comprises a guide body defining a channel sized and configured to receive the spring-loaded locking element therethrough, wherein the channel defines a retention element at a proximal end.

28. The method of ankle replacement of claim 23, wherein the second surface is configured to engage the second transverse arm of the offset impactor.

29. The method of ankle replacement of claim 1, wherein the plurality of broaches includes a pilot broach and an enlarging broach.

30. A method, comprising:
   forming an anterior cut in a bone;
   coupling a first broach to an offset impactor, the offset impactor including
      a body including a longitudinal section having a first arm coupled to a first end and a second arm coupled to a second end such that a space is defined between the first arm and the second arm;
      an impactor surface coupled to the first arm; and
      an impactor body coupled to the second arm,
   forming a first hole in the bone by applying a first impaction force to the impactor surface;
   replacing the first broach with a second broach;
   forming a stem hole in the bone by applying a second impaction force to the impactor surface;
   inserting a first portion of a stem into the stem hole through the anterior cut in the bone;
   inserting a second portion of the stem into the stem hole through the anterior cut in the bone;
   coupling the first portion to the second portion using a coupling device inserted through the anterior cut in the bone; and
   impacting a stem implant into the stem hole by applying a third impaction force to the impactor surface of the offset impactor.

31. The method of claim 30, further comprising coupling a broach guide to an anterior surface of the bone prior to forming the first hole in the bone.

32. The method of claim 30, further comprising coupling an implant to the second portion of the stem.

33. A method, comprising:
   forming an anterior cut in a first bone;
   forming a stem hole in a distal end of the first bone using a plurality of broaches positioned against the distal end of the first bone through the anterior cut;
   inserting a first portion of a stem into the stem hole through the anterior cut in the first bone;
   inserting a second portion of the stem into the stem hole through the anterior cut in the first bone;
   coupling the first portion to the second portion using an offset driver inserted through the anterior cut in the bone, the offset driver including:
      an elongate body extending from a first end to a second end and defining a longitudinal axis; and
      a driver head disposed at the second end of the elongate body, the driver head including a bit drive configured to be received in a space between the first bone and a second bone and to engage the second portion of the stem, the driver head configured to rotate about an axis that is disposed an angle with respect to the longitudinal axis defined by the elongate body; and
   impacting the stem implant into the stem hole by applying an impaction force to an offset impactor.

34. The method of claim 33, wherein forming the stem hole in the distal end of the first bone includes:
   coupling a first broach to the offset impactor;
   forming a first hole in the first bone by applying a first impaction force to an impactor surface;
   replacing the first broach with a second broach; and
   forming the stem hole in the first bone by applying a second impaction force to the impactor surface.

* * * * *